US005831058A

United States Patent [19]
Fujiwara et al.

[11] Patent Number: 5,831,058
[45] Date of Patent: Nov. 3, 1998

[54] HUMAN GDP DISSOCIATION STIMULATING PROTEIN GENE

[75] Inventors: Tsutomu Fujiwara, Naruto; Takeshi Watanabe, Tokushima-ken; Masato Horie, Tokushima, all of Japan

[73] Assignee: Otsuka Pharmaceutical Co., Ltd., Tokyo, Japan

[21] Appl. No.: 820,170

[22] Filed: Mar. 19, 1997

[30] Foreign Application Priority Data

Mar. 19, 1996 [JP] Japan .................................... 8-063410
Mar. 5, 1997 [JP] Japan .................................... 9-069163

[51] Int. Cl.$^6$ ..................................................... C07H 21/04
[52] U.S. Cl. ............................................................ 536/23.5
[58] Field of Search ................................. 536/23.1, 23.2, 536/23.5; 530/350

[56] References Cited

PUBLICATIONS

Peterson et al. Identification of a Novel RaIGDS–Related as a Candidate Effector for Ras and Rap1. J. Biol. Chem. 271(47): 29903–29908, Nov. 1996.
Abstract of EMBO J., 12, pp. 339–347 (1993).
GeneBank database accession Z4991, L34070, U18530 and X59720.
Abstract of Genomics, 9 (4), pp. 728–736 (1991).
Abstract of Nature, 357 (6380), pp. 700–702 (1992).
GeneBank database accession Z49154.
Abstract of Biochem. J., 297 (Pt2), pp. 389–397 (1994).
Abstract of Mol. Cell. Biol., 15 (10), pp. 5645–5656 (1995).
Abstract of Dev. Dyn., 203 (2), pp. 212–222 (1995).
Abstract of EMBO J., 8 (12), pp. 3807–3814 (1989).
Hum. Genet., 86, pp. 14–16 (1990).
Proc. Natl. Acad. Sci., U.S.A., 87, pp. 6634–6638 (1990).
DNA Research, 2, 107–111 (1995).
Hum Genet., 88, pp. 119–121 (1991).

*Primary Examiner*—George C. Elliott
*Assistant Examiner*—Thomas G. Larson
*Attorney, Agent, or Firm*—Sughrue, Mion, Zinn, Macpeak & Seas, PLLC

[57] ABSTRACT

The present invention provides novel human genes, for example a novel human gene comprising a nucleotide sequence coding for the amino acid sequence shown under SEQ ID NO:1. The use of the genes makes it possible to detect the expression of the same in various tissues, analyze their structures and functions, and produce the human proteins encoded by the genes by the technology of genetic engineering. Through these, it becomes possible to analyze the corresponding expression products, elucidate the pathology of diseases associated with the genes, for example hereditary diseases and cancer, and diagnose and treat such diseases.

3 Claims, 1 Drawing Sheet

F I G. 1
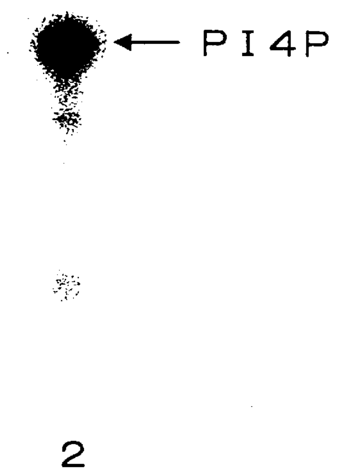
F I G. 2
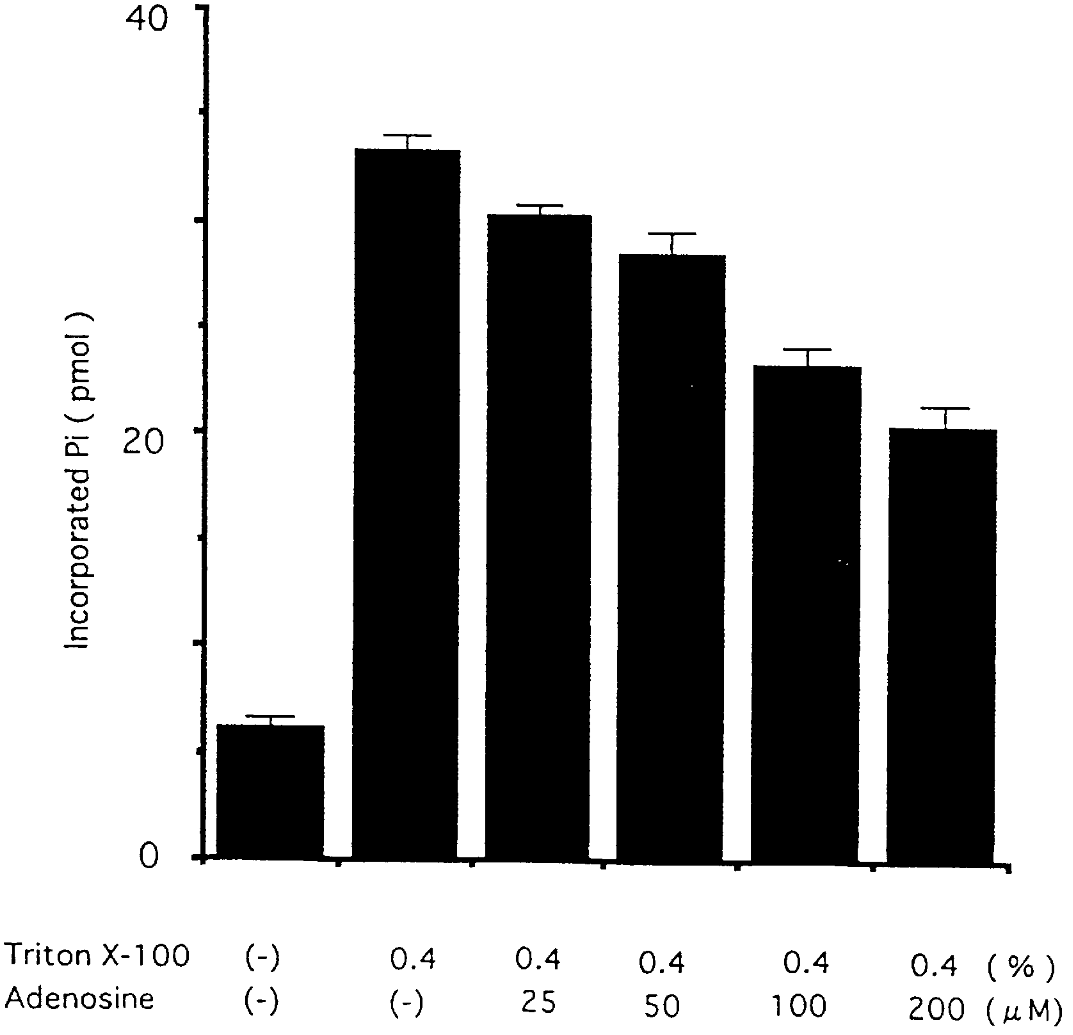

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
( A ) LENGTH: 122 amino acids
( B ) TYPE: amino acid
( D ) TOPOLOGY: linear ( i i ) MOLECULE TYPE: protein ( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Glu | Leu | Gly | Glu | Asp | Gly | Ser | Val | Tyr | Lys | Ser | Ile | Leu | Val | Thr |
| 1 | | | | 5 | | | | | 10 | | | | | 15 | |
| Ser | Gln | Asp | Lys | Ala | Pro | Ser | Val | Ile | Ser | Arg | Val | Leu | Lys | Lys | Asn |
| | | | 20 | | | | | 25 | | | | | 30 | | |
| Asn | Arg | Asp | Ser | Ala | Val | Ala | Ser | Glu | Tyr | Glu | Leu | Val | Gln | Leu | Leu |
| | | 35 | | | | | 40 | | | | | 45 | | | |
| Pro | Gly | Glu | Arg | Glu | Leu | Thr | Ile | Pro | Ala | Ser | Ala | Asn | Val | Phe | Tyr |
| | 50 | | | | | 55 | | | | | 60 | | | | |
| Pro | Met | Asp | Gly | Ala | Ser | His | Asp | Phe | Leu | Leu | Arg | Gln | Arg | Arg | Arg |
| 65 | | | | | 70 | | | | | 75 | | | | | 80 |
| Ser | Ser | Thr | Ala | Thr | Pro | Gly | Val | Thr | Ser | Gly | Pro | Ser | Ala | Ser | Gly |
| | | | | 85 | | | | | 90 | | | | | 95 | |
| Thr | Pro | Pro | Ser | Glu | Gly | Gly | Gly | Gly | Ser | Phe | Pro | Arg | Ile | Lys | Ala |
| | | | 100 | | | | | 105 | | | | | 110 | | |

```
Thr Gly Arg Lys Ile Ala Arg Ala Leu Phe
        115                 120
```

(2) INFORMATION FOR SEQ ID NO:2:

(i) SEQUENCE CHARACTERISTICS:
(A) LENGTH: 366 base pairs
(B) TYPE: nucleic acid
(C) STRANDEDNESS: single
(D) TOPOLOGY: linear (ii) MOLECULE TYPE: DNA(cDNA)

(xi) SEQUENCE DESCRIPTION: SEQ ID NO:2:

```
ATGGAGTTGG GGGAAGATGG CAGTGTCTAT AAGAGCATTT TGGTGACAAG CCAGGACAAG    60

GCTCCAAGTG TCATCAGTCG TGTCCTTAAG AAAAACAATC GTGACTCTGC AGTGGCTTCA   120

GAGTATGAGC TGGTACAGCT GCTACCAGGG GAGCGAGAGC TGACTATCCC AGCCTCGGCT   180

AATGTATTCT ACCCCATGGA TGGAGCTTCA CACGATTTCC TCCTGCGGCA GCGGCGAAGG   240

TCCTCTACTG CTACACCTGG CGTCACCAGT GGCCCGTCTG CCTCAGGAAC TCCTCCGAGT   300

GAGGGAGGAG GGGGCTCCTT TCCCAGGATC AAGGCCACAG GGAGGAAGAT TGCACGGGCA   360

CTGTTC                                                               366
```

(2) INFORMATION FOR SEQ ID NO:3:

(i) SEQUENCE CHARACTERISTICS:
(A) LENGTH: 842 base pairs
(B) TYPE: nucleic acid
(C) STRANDEDNESS: single
(D) TOPOLOGY: linear (ii) MOLECULE TYPE: DNA(genomic)

(iii) HYPOTHETICAL: NO (iv) ANTI-SENSE: NO (vii) IMMEDIATE SOURCE:
(A) LIBRARY: Human fetal brain cDNA library
(B) CLONE: GEN-501D08

(ix) FEATURE:
(A) NAME/KEY: CDS
(B) LOCATION: 28..393

(xi) SEQUENCE DESCRIPTION: SEQ ID NO:3:

```
CCCACGAGCC GTATCATCCG AGTCCAG ATG GAG TTG GGG GAA GAT GGC AGT       51
                              Met Glu Leu Gly Glu Asp Gly Ser
                                1               5

GTC TAT AAG AGC ATT TTG GTG ACA AGC CAG GAC AAG GCT CCA AGT GTC     99
Val Tyr Lys Ser Ile Leu Val Thr Ser Gln Asp Lys Ala Pro Ser Val
     10                  15                  20

ATC AGT CGT GTC CTT AAG AAA AAC AAT CGT GAC TCT GCA GTG GCT TCA    147
Ile Ser Arg Val Leu Lys Lys Asn Asn Arg Asp Ser Ala Val Ala Ser
 25                  30                  35                  40

GAG TAT GAG CTG GTA CAG CTG CTA CCA GGG GAG CGA GAG CTG ACT ATC    195
Glu Tyr Glu Leu Val Gln Leu Leu Pro Gly Glu Arg Glu Leu Thr Ile
                 45                  50                  55

CCA GCC TCG GCT AAT GTA TTC TAC CCC ATG GAT GGA GCT TCA CAC GAT    243
Pro Ala Ser Ala Asn Val Phe Tyr Pro Met Asp Gly Ala Ser His Asp
             60                  65                  70

TTC CTC CTG CGG CAG CGG CGA AGG TCC TCT ACT GCT ACA CCT GGC GTC    291
Phe Leu Leu Arg Gln Arg Arg Arg Ser Ser Thr Ala Thr Pro Gly Val
         75                  80                  85
```

-continued

```
ACC AGT GGC CCG TCT GCC TCA GGA ACT CCT CCG AGT GAG GGA GGA GGG      339
Thr Ser Gly Pro Ser Ala Ser Gly Thr Pro Pro Ser Glu Gly Gly Gly
     90                      95                 100

GGC TCC TTT CCC AGG ATC AAG GCC ACA GGG AGG AAG ATT GCA CGG GCA      387
Gly Ser Phe Pro Arg Ile Lys Ala Thr Gly Arg Lys Ile Ala Arg Ala
105                 110                 115                 120

CTG TTC TGAGGAGGAA GCCCCTTTTT TTACAGAAGT CATGGTGTTC ATACCAGATG       443
Leu Phe

TGGGTAGCCA TCCTGAATGG TGGCAATTAT ATCACATTGA GACAGAAATT CAGAAAGGGA    503

GCCAGCCACC CTGGGGCAGT GAAGTGCCAC TGGTTTACCA GACAGCTGAG AAATCCAGCC    563

CTGTCGGAAC TGGTGTCTTA TAACCAAGTT GGATACCTGT GTATAGCTTG CCACCTTCCA    623

TGAGTGCAGC ACACAGGTAG TGCTGGAAAA ACGCATCAGT TTCTGATTCT TGGCCATATC    683

CTAACATGCA AGGGCCAAGC AAAGGCTTCA AGGCTCTGAG CCCCAGGGCA GAGGGGAATG    743

GCAAAATGTA GGTCCTGGCA GGAGCTCTTC TTCCCACTCT GGGGGTTTCT ATCACTGTGA    803

CAACACTAAG ATAATAAACC AAAACACTAC CTGAATTCT                           842
```

( 2 ) INFORMATION FOR SEQ ID NO:4:

( i ) SEQUENCE CHARACTERISTICS:
( A ) LENGTH: 193 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Glu Leu Glu Leu Tyr Gly Val Asp Asp Lys Phe Tyr Ser Lys Leu
  1               5                  10                  15

Asp Gln Glu Asp Ala Leu Leu Gly Ser Tyr Pro Val Asp Asp Gly Cys
             20                  25                  30

Arg Ile His Val Ile Asp His Ser Gly Ala Arg Leu Gly Glu Tyr Glu
         35                  40                  45

Asp Val Ser Arg Val Glu Lys Tyr Thr Ile Ser Gln Glu Ala Tyr Asp
     50                  55                  60

Gln Arg Gln Asp Thr Val Arg Ser Phe Leu Lys Arg Ser Lys Leu Gly
 65                  70                  75                  80

Arg Tyr Asn Glu Glu Glu Arg Ala Gln Gln Glu Ala Glu Ala Ala Gln
                 85                  90                  95

Arg Leu Ala Glu Glu Lys Ala Gln Ala Ser Ser Ile Pro Val Gly Ser
            100                 105                 110

Arg Cys Glu Val Arg Ala Ala Gly Gln Ser Pro Arg Arg Gly Thr Val
        115                 120                 125

Met Tyr Val Gly Leu Thr Asp Phe Lys Pro Gly Tyr Trp Ile Gly Val
    130                 135                 140

Arg Tyr Asp Glu Pro Leu Gly Lys Asn Asp Gly Ser Val Asn Gly Lys
145                 150                 155                 160

Arg Tyr Phe Glu Cys Gln Ala Lys Tyr Gly Ala Phe Val Lys Pro Ala
                165                 170                 175

Val Val Thr Val Gly Asp Phe Pro Glu Glu Asp Tyr Gly Leu Asp Glu
            180                 185                 190

Ile
```

( 2 ) INFORMATION FOR SEQ ID NO:5:

( i ) SEQUENCE CHARACTERISTICS:
( A ) LENGTH: 579 base pairs ( B ) TYPE: nucleic acid
( C ) STRANDEDNESS: single
( D ) TOPOLOGY: linear ( i i ) MOLECULE TYPE: DNA(cDNA)

( x i ) SEQUENCE DESCRIPTION: SEQ ID NO:5:

```
ATGGAACTGG AGCTGTATGG AGTTGACGAC AAGTTCTACA GCAAGCTGGA TCAAGAGGAT    60
GCGCTCCTGG GCTCCTACCC TGTAGATGAC GGCTGCCGCA TCCACGTCAT TGACCACAGT   120
GGCGCCCGCC TTGGTGAGTA TGAGGACGTG TCCCGGGTGG AGAAGTACAC GATCTCACAA   180
GAAGCCTACG ACCAGAGGCA AGACACGGTC CGCTCTTTCC TGAAGCGCAG CAAGCTCGGC   240
CGGTACAACG AGGAGGAGCG GGCTCAGCAG GAGGCCGAGG CCGCCCAGCG CCTGGCCGAG   300
GAGAAGGCCC AGGCCAGCTC CATCCCCGTG GGCAGCCGCT GTGAGGTGCG GGCGGCGGGA   360
CAATCCCCTC GCCGGGGCAC CGTCATGTAT GTAGGTCTCA CAGATTTCAA GCCTGGCTAC   420
TGGATTGGTG TCCGCTATGA TGAGCCACTG GGGAAAAATG ATGGCAGTGT GAATGGGAAA   480
CGCTACTTCG AATGCCAGGC CAAGTATGGC GCCTTTGTCA AGCCAGCAGT CGTGACGGTG   540
GGGGACTTCC CGGAGGAGGA CTACGGGTTG GACGAGATA                          579
```

( 2 ) INFORMATION FOR SEQ ID NO:6:

( i ) SEQUENCE CHARACTERISTICS:
( A ) LENGTH: 1015 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-080G01

( i x ) FEATURE:
( A ) NAME/KEY: CDS
( B ) LOCATION: 274..852

( x i ) SEQUENCE DESCRIPTION: SEQ ID NO:6:

```
TGATTGGTCA GGCACGGAGC AGGAGGCGGG CTGATAGCCC AGCAGCAGCA GCGGCGGCGG    60
CGGCTGCGGA GCGGGTGTGA GGCGGCTGGA CCGCGCTGCA GGCATCCGCG GGCGCGGCAA   120
GATGGAGGTG ACGGGGGTGT CGGCACCACG GTGACCGTTT TCATCAGCAG CTCCCTCAGC   180
ACCTTCCGCT CCGAGAAGCG ATACAGCCGC AGCCTCACCA TCGCTGAGTT CAAGTGTAAA   240
CTGGAGTTGC TGGTGGGCAG CCCTGCTTCC TGC ATG GAA CTG GAG CTG TAT GGA    294
                                     Met Glu Leu Glu Leu Tyr Gly
                                       1               5

GTT GAC GAC AAG TTC TAC AGC AAG CTG GAT CAA GAG GAT GCG CTC CTG     342
Val Asp Asp Lys Phe Tyr Ser Lys Leu Asp Gln Glu Asp Ala Leu Leu
         10                  15                  20

GGC TCC TAC CCT GTA GAT GAC GGC TGC CGC ATC CAC GTC ATT GAC CAC     390
Gly Ser Tyr Pro Val Asp Asp Gly Cys Arg Ile His Val Ile Asp His
    25                  30                  35

AGT GGC GCC CGC CTT GGT GAG TAT GAG GAC GTG TCC CGG GTG GAG AAG     438
Ser Gly Ala Arg Leu Gly Glu Tyr Glu Asp Val Ser Arg Val Glu Lys
 40                  45                  50                  55

TAC ACG ATC TCA CAA GAA GCC TAC GAC CAG AGG CAA GAC ACG GTC CGC     486
Tyr Thr Ile Ser Gln Glu Ala Tyr Asp Gln Arg Gln Asp Thr Val Arg
                60                  65                  70
```

-continued

```
TCT TTC CTG AAG CGC AGC AAG CTC GGC CGG TAC AAC GAG GAG GAG CGG      534
Ser Phe Leu Lys Arg Ser Lys Leu Gly Arg Tyr Asn Glu Glu Glu Arg
             75                  80                  85

GCT CAG CAG GAG GCC GAG GCC GCC CAG CGC CTG GCC GAG GAG AAG GCC      582
Ala Gln Gln Glu Ala Glu Ala Ala Gln Arg Leu Ala Glu Glu Lys Ala
         90                  95                 100

CAG GCC AGC TCC ATC CCC GTG GGC AGC CGC TGT GAG GTG CGG GCG GCG      630
Gln Ala Ser Ser Ile Pro Val Gly Ser Arg Cys Glu Val Arg Ala Ala
    105                 110                 115

GGA CAA TCC CCT CGC CGG GGC ACC GTC ATG TAT GTA GGT CTC ACA GAT      678
Gly Gln Ser Pro Arg Arg Gly Thr Val Met Tyr Val Gly Leu Thr Asp
120                 125                 130                 135

TTC AAG CCT GGC TAC TGG ATT GGT GTC CGC TAT GAT GAG CCA CTG GGG      726
Phe Lys Pro Gly Tyr Trp Ile Gly Val Arg Tyr Asp Glu Pro Leu Gly
                140                 145                 150

AAA AAT GAT GGC AGT GTG AAT GGG AAA CGC TAC TTC GAA TGC CAG GCC      774
Lys Asn Asp Gly Ser Val Asn Gly Lys Arg Tyr Phe Glu Cys Gln Ala
            155                 160                 165

AAG TAT GGC GCC TTT GTC AAG CCA GCA GTC GTG ACG GTG GGG GAC TTC      822
Lys Tyr Gly Ala Phe Val Lys Pro Ala Val Val Thr Val Gly Asp Phe
        170                 175                 180

CCG GAG GAG GAC TAC GGG TTG GAC GAG ATA TGACACCTAA GGAATTCCCC        872
Pro Glu Glu Asp Tyr Gly Leu Asp Glu Ile
    185                 190

TGCTTCAGCT CCTAGCTCAG CCACTGACTG CCCCTCCTGT GTGTGCCCAT GGCCCTTTTC    932

TCCTGACCCC ATTTTAATTT TATTCATTTT TTCCTTTGCC ATTGATTTTT GAGACTCATG    992

CATTAAATTC ACTAGAAACC CAG                                           1015
```

( 2 ) INFORMATION FOR SEQ ID NO:7:

( i ) SEQUENCE CHARACTERISTICS:
( A ) LENGTH: 128 amino acids
( B ) TYPE: amino acid
( D ) TOPOLOGY: linear ( i i ) MOLECULE TYPE: protein ( x i ) SEQUENCE DESCRIPTION: SEQ ID NO:7:

```
Met Thr Glu Ala Asp Val Asn Pro Lys Ala Tyr Pro Leu Ala Asp Ala
  1               5                  10                  15

His Leu Thr Lys Lys Leu Leu Asp Leu Val Gln Gln Ser Cys Asn Tyr
             20                  25                  30

Lys Gln Leu Arg Lys Gly Ala Asn Glu Ala Thr Lys Thr Leu Asn Arg
         35                  40                  45

Gly Ile Ser Glu Phe Ile Val Met Ala Ala Asp Ala Glu Pro Leu Glu
     50                  55                  60

Ile Ile Leu His Leu Pro Leu Leu Cys Glu Asp Lys Asn Val Pro Tyr
 65                  70                  75                  80

Val Phe Val Arg Ser Lys Gln Ala Leu Gly Arg Ala Cys Gly Val Ser
                 85                  90                  95

Arg Pro Val Ile Ala Cys Ser Val Thr Ile Lys Glu Gly Ser Gln Leu
            100                 105                 110

Lys Gln Gln Ile Gln Ser Ile Gln Gln Ser Ile Glu Arg Leu Leu Val
        115                 120                 125
```

( 2 ) INFORMATION FOR SEQ ID NO:8:

( i ) SEQUENCE CHARACTERISTICS:
( A ) LENGTH: 384 base pairs ( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:8:

```
ATGACTGAGG CTGATGTGAA TCCAAAGGCC TATCCCCTTG CCGATGCCCA CCTCACCAAG    60

AAGCTACTGG ACCTCGTTCA GCAGTCATGT AACTATAAGC AGCTTCGGAA AGGAGCCAAT   120

GAGGCCACCA AAACCCTCAA CAGGGGCATC TCTGAGTTCA TCGTGATGGC TGCAGACGCC   180

GAGCCACTGG AGATCATTCT GCACCTGCCG CTGCTGTGTG AAGACAAGAA TGTGCCCTAC   240

GTGTTTGTGC GCTCCAAGCA GGCCCTGGGG AGAGCCTGTG GGGTCTCCAG GCCTGTCATC   300

GCCTGTTCTG TCACCATCAA AGAAGGCTCG CAGCTGAAAC AGCAGATCCA ATCCATTCAG   360

CAGTCCATTG AAAGGCTCTT AGTC                                          384
```

( 2 ) INFORMATION FOR SEQ ID NO:9:

( i ) SEQUENCE CHARACTERISTICS:
( A ) LENGTH: 1493 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-025F07

( i x ) FEATURE:
( A ) NAME/KEY: CDS
( B ) LOCATION: 95..478

( x i ) SEQUENCE DESCRIPTION: SEQ ID NO:9:

```
ATCCGTGTCC TTGCGGTGCT GGGCAGCAGA CCGTCCAAAC CGACACGCGT GGTATCCTCG    60

CGGTGTCCGG CAAGAGACTA CCAAGACAGA CGCT ATG ACT GAG GCT GAT GTG       112
                                      Met Thr Glu Ala Asp Val
                                        1               5

AAT CCA AAG GCC TAT CCC CTT GCC GAT GCC CAC CTC ACC AAG AAG CTA   160
Asn Pro Lys Ala Tyr Pro Leu Ala Asp Ala His Leu Thr Lys Lys Leu
             10                  15                  20

CTG GAC CTC GTT CAG CAG TCA TGT AAC TAT AAG CAG CTT CGG AAA GGA   208
Leu Asp Leu Val Gln Gln Ser Cys Asn Tyr Lys Gln Leu Arg Lys Gly
         25                  30                  35

GCC AAT GAG GCC ACC AAA ACC CTC AAC AGG GGC ATC TCT GAG TTC ATC   256
Ala Asn Glu Ala Thr Lys Thr Leu Asn Arg Gly Ile Ser Glu Phe Ile
     40                  45                  50

GTG ATG GCT GCA GAC GCC GAG CCA CTG GAG ATC ATT CTG CAC CTG CCG   304
Val Met Ala Ala Asp Ala Glu Pro Leu Glu Ile Ile Leu His Leu Pro
 55                  60                  65                  70

CTG CTG TGT GAA GAC AAG AAT GTG CCC TAC GTG TTT GTG CGC TCC AAG   352
Leu Leu Cys Glu Asp Lys Asn Val Pro Tyr Val Phe Val Arg Ser Lys
                 75                  80                  85

CAG GCC CTG GGG AGA GCC TGT GGG GTC TCC AGG CCT GTC ATC GCC TGT   400
Gln Ala Leu Gly Arg Ala Cys Gly Val Ser Arg Pro Val Ile Ala Cys
             90                  95                 100

TCT GTC ACC ATC AAA GAA GGC TCG CAG CTG AAA CAG CAG ATC CAA TCC   448
Ser Val Thr Ile Lys Glu Gly Ser Gln Leu Lys Gln Gln Ile Gln Ser
        105                 110                 115
```

-continued

```
ATT CAG CAG TCC ATT GAA AGG CTC TTA GTC TAAACCTGTG GCCTCTGCCA      498
Ile Gln Gln Ser Ile Glu Arg Leu Leu Val
    120                 125

CGTGCTCCCT GCCAGCTTCC CCCCTGAGGT TGTGTATCAT ATTATCTGTG TTAGCATGTA  558

GTATTTTCAG CTACTCTCTA TTGTTATAAA ATGTAGTACT AAATCTGGTT TCTGGATTTT  618

TGTGTTGTTT TTGTTCTGTT TTACAGGGTT GCTATCCCCC TTCCTTTCCT CCCTCCCTCT  678

GCCATCCTTC ATCCTTTTAT CCTCCCTTTT TGGAACAAGT GTTCAGAGCA GACAGAAGCA  738

GGGTGGTGGC ACCGTTGAAA GGCAGAAAGA GCCAGGAGAA AGCTGATGGA GCCAGGACAG  798

AGATCTGGTT CCAGCTTTCA GCCACTAGCT TCCTGTTGTG TGCGGGGTGT GGTGGAATTA  858

AACAGCATTC ATTGTGTGTC CCTGTGCCTG GCACACAGAA TCATTCATAC GTGTTCAAGT  918

GATCAAGGGG TTTCATTTGC TCTTGGGGGA TTAGGTATCA TTTGGGGAGG AAGCATGTGT  978

TCTGTGAGGT TGTTCGGCTA TGTCCAAGTG TCGTTTACTA ATGTACCCCT GCTGTTTGCT 1038

TTTGGTAATG TGATGTTGAT GTTCTCCCCC TACCCACAAC CATGCCCTTG AGGGTAGCAG 1098

GGCAGCAGCA TACCAAAGAG ATGTGCTGCA GGACTCCGGA GGCAGCCTGG GTGGGTGAGC 1158

CATGGGGCAG TTGACCTGGG TCTTGAAAGA GTCGGGAGTG ACAAGCTCAG AGAGCATGAA 1218

CTGATGCTGG CATGAAGGAT TCCAGGAAGA TCATGGAGAC CTGGCTGGTA GCTGTAACAG 1278

AGATGGTGGA GTCCAAGGAA ACAGCCTGTC TCTGGTGAAT GGGACTTTCT TTGGTGGACA 1338

CTTGGCACCA GCTCTGAGAG CCCTTCCCCT GTGTCCTGCC ACCATGTGGG TCAGATGTAC 1398

TCTCTGTCAC ATGAGGAGAG TGCTAGTTCA TGTGTTCTCC ATTCTTGTGA GCATCCTAAT 1458

AAATCTGTTC CATTTTGAAA AAAAAAAAAA AAAAA                             1493
```

( 2 ) INFORMATION FOR SEQ ID NO:10:

( i ) SEQUENCE CHARACTERISTICS:
( A ) LENGTH: 711 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Pro Ala Asp Val Asn Leu Ser Gln Lys Pro Gln Val Leu Gly Pro
  1               5                  10                  15

Glu Lys Gln Asp Gly Ser Cys Glu Ala Ser Val Ser Phe Glu Asp Val
             20                  25                  30

Thr Val Asp Phe Ser Arg Glu Glu Trp Gln Gln Leu Asp Pro Ala Gln
         35                  40                  45

Arg Cys Leu Tyr Arg Asp Val Met Leu Glu Leu Tyr Ser His Leu Phe
     50                  55                  60

Ala Val Gly Tyr His Ile Pro Asn Pro Glu Val Ile Phe Arg Met Leu
 65                  70                  75                  80

Lys Glu Lys Glu Pro Arg Val Glu Glu Ala Glu Val Ser His Gln Arg
                 85                  90                  95

Cys Gln Glu Arg Glu Phe Gly Leu Glu Ile Pro Gln Lys Glu Ile Ser
            100                 105                 110

Lys Lys Ala Ser Phe Gln Lys Asp Met Val Gly Glu Phe Thr Arg Asp
        115                 120                 125

Gly Ser Trp Cys Ser Ile Leu Glu Glu Leu Arg Leu Asp Ala Asp Arg
    130                 135                 140

Thr Lys Lys Asp Glu Gln Asn Gln Ile Gln Pro Met Ser His Ser Ala
145                 150                 155                 160
```

```
Phe Phe Asn Lys Lys Thr Leu Asn Thr Glu Ser Asn Cys Glu Tyr Lys
                165                 170                 175

Asp Pro Gly Lys Met Ile Arg Thr Arg Pro His Leu Ala Ser Ser Gln
            180                 185                 190

Lys Gln Pro Gln Lys Cys Cys Leu Phe Thr Glu Ser Leu Lys Leu Asn
        195                 200                 205

Leu Glu Val Asn Gly Gln Asn Glu Ser Asn Asp Thr Glu Gln Leu Asp
    210                 215                 220

Asp Val Val Gly Ser Gly Gln Leu Phe Ser His Ser Ser Ser Asp Ala
225                 230                 235                 240

Cys Ser Lys Asn Ile His Thr Gly Glu Thr Phe Cys Lys Gly Asn Gln
                245                 250                 255

Cys Arg Lys Val Cys Gly His Lys Gln Ser Leu Lys Gln His Gln Ile
            260                 265                 270

His Thr Gln Lys Lys Pro Asp Gly Cys Ser Glu Cys Gly Gly Ser Phe
        275                 280                 285

Thr Gln Lys Ser His Leu Phe Ala Gln Gln Arg Ile His Ser Val Gly
    290                 295                 300

Asn Leu His Glu Cys Gly Lys Cys Gly Lys Ala Phe Met Pro Gln Leu
305                 310                 315                 320

Lys Leu Ser Val Tyr Leu Thr Asp His Thr Gly Asp Ile Pro Cys Ile
                325                 330                 335

Cys Lys Glu Cys Gly Lys Val Phe Ile Gln Arg Ser Glu Leu Leu Thr
            340                 345                 350

His Gln Lys Thr His Thr Arg Lys Lys Pro Tyr Lys Cys His Asp Cys
        355                 360                 365

Gly Lys Ala Phe Phe Gln Met Leu Ser Leu Phe Arg His Gln Arg Thr
    370                 375                 380

His Ser Arg Glu Lys Leu Tyr Glu Cys Ser Glu Cys Gly Lys Gly Phe
385                 390                 395                 400

Ser Gln Asn Ser Thr Leu Ile Ile His Gln Lys Ile His Thr Gly Glu
                405                 410                 415

Arg Gln Tyr Ala Cys Ser Glu Cys Gly Lys Ala Phe Thr Gln Lys Ser
            420                 425                 430

Thr Leu Ser Leu His Gln Arg Ile His Ser Gly Gln Lys Ser Tyr Val
        435                 440                 445

Cys Ile Glu Cys Gly Gln Ala Phe Ile Gln Lys Ala His Leu Ile Val
    450                 455                 460

His Gln Arg Ser His Thr Gly Glu Lys Pro Tyr Gln Cys His Asn Cys
465                 470                 475                 480

Gly Lys Ser Phe Ile Ser Lys Ser Gln Leu Asp Ile His His Arg Ile
                485                 490                 495

His Thr Gly Glu Lys Pro Tyr Glu Cys Ser Asp Cys Gly Lys Thr Phe
            500                 505                 510

Thr Gln Lys Ser His Leu Asn Ile His Gln Lys Ile His Thr Gly Glu
        515                 520                 525

Arg His His Val Cys Ser Glu Cys Gly Lys Ala Phe Asn Gln Lys Ser
    530                 535                 540

Ile Leu Ser Met His Gln Arg Ile His Thr Gly Glu Lys Pro Tyr Lys
545                 550                 555                 560

Cys Ser Glu Cys Gly Lys Ala Phe Thr Ser Lys Ser Gln Phe Lys Glu
                565                 570                 575

His Gln Arg Ile His Thr Gly Glu Lys Pro Tyr Val Cys Thr Glu Cys
```

-continued 580 585 590

Gly Lys Ala Phe Asn Gly Arg Ser Asn Phe His Lys His Gln Ile Thr
595 600 605

His Thr Arg Glu Arg Pro Phe Val Cys Tyr Lys Cys Gly Lys Ala Phe
610 615 620

Val Gln Lys Ser Glu Leu Ile Thr His Gln Arg Thr His Met Gly Glu
625 630 635 640

Lys Pro Tyr Glu Cys Leu Asp Cys Gly Lys Ser Phe Ser Lys Lys Pro
645 650 655

Gln Leu Lys Val His Gln Arg Ile His Thr Gly Glu Arg Pro Tyr Val
660 665 670

Cys Ser Glu Cys Gly Lys Ala Phe Asn Asn Arg Ser Asn Phe Asn Lys
675 680 685

His Gln Thr Thr His Thr Arg Asp Lys Ser Tyr Lys Cys Ser Tyr Ser
690 695 700

Val Lys Gly Phe Thr Lys Gln
705 710

( 2 ) INFORMATION FOR SEQ ID NO:11:

( i ) SEQUENCE CHARACTERISTICS:
( A ) LENGTH: 2133 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:11:

ATGCCTGCTG ATGTGAATTT ATCCCAGAAG CCTCAGGTCC TGGGTCCAGA GAAGCAGGAT 60

GGATCTTGCG AGGCATCAGT GTCATTTGAG GACGTGACCG TGGACTTCAG CAGGGAGGAG 120

TGGCAGCAAC TGGACCCTGC CCAGAGATGC CTGTACCGGG ATGTGATGCT GGAGCTCTAT 180

AGCCATCTCT TCGCAGTGGG GTATCACATT CCCAACCCAG AGGTCATCTT CAGAATGCTA 240

AAAGAAAAGG AGCCGCGTGT GGAGGAGGCT GAAGTCTCAC ATCAGAGGTG TCAAGAAAGG 300

GAGTTTGGGC TTGAAATCCC ACAAAAGGAG ATTTCTAAGA AAGCTTCATT TCAAAAGGAT 360

ATGGTAGGTG AGTTCACAAG AGATGGTTCA TGGTGTTCCA TTTTAGAAGA ACTGAGGCTG 420

GATGCTGACC GCACAAAGAA AGATGAGCAA AATCAAATTC AACCCATGAG TCACAGTGCT 480

TTCTTCAACA AGAAAACATT GAACACAGAA AGCAATTGTG AATATAAGGA CCCTGGGAAA 540

ATGATTCGCA CGAGGCCCCA CCTTGCTTCT TCACAGAAAC AACCTCAGAA ATGTTGCTTA 600

TTTACAGAAA GTTTGAAGCT GAACCTAGAA GTGAACGGTC AGAATGAAAG CAATGACACA 660

GAACAGCTTG ATGACGTTGT TGGGTCTGGT CAGCTATTCA GCCATAGCTC TTCTGATGCC 720

TGCAGCAAGA ATATTCATAC AGGAGAGACA TTTTGCAAAG GTAACCAGTG TAGAAAAGTC 780

TGTGGCCATA AACAGTCACT CAAGCAACAT CAAATTCATA CTCAGAAGAA ACCAGATGGA 840

TGTTCTGAAT GTGGGGGGAG CTTCACCCAG AAGTCACACC TCTTTGCCCA ACAGAGAATT 900

CATAGTGTAG GAAACCTCCA TGAATGTGGC AAATGTGGAA AAGCCTTCAT GCCACAACTA 960

AAACTCAGTG TATATCTGAC AGATCATACA GGTGATATAC CCTGTATATG CAAGGAATGT 1020

GGGAAGGTCT TTATTCAGAG ATCAGAATTG CTTACGCACC AGAAAACACA CACTAGAAAG 1080

AAGCCCTATA AATGCCATGA CTGTGGAAAA GCCTTTTTCC AGATGTTATC TCTCTTCAGA 1140

CATCAGAGAA CTCACAGTAG AGAAAAACTC TATGAATGCA GTGAATGTGG CAAAGGCTTC 1200

TCCCAAAACT CAACCCTCAT TATACATCAG AAAATTCATA CTGGTGAGAG ACAGTATGCA 1260

-continued

```
TGCAGTGAAT GTGGGAAAGC CTTTACCCAG AAGTCAACAC TCAGCTTGCA CCAGAGAATC 1320
CACTCAGGGC AGAAGTCCTA TGTGTGTATC GAATGCGGGC AGGCCTTCAT CCAGAAGGCA 1380
CACCTGATTG TCCATCAAAG AAGCCACACA GGAGAAAAAC CTTATCAGTG CCACAACTGT 1440
GGGAAATCCT TCATTTCCAA GTCACAGCTT GATATACATC ATCGAATTCA TACAGGGGAG 1500
AAACCTTATG AATGCAGTGA CTGTGGAAAA ACCTTCACCC AAAAGTCACA CCTGAATATA 1560
CACCAGAAAA TTCATACTGG AGAAAGACAC CATGTATGCA GTGAATGCGG GAAAGCCTTC 1620
AACCAGAAGT CAATACTCAG CATGCATCAG AGAATTCACA CCGGAGAGAA GCCTTACAAA 1680
TGCAGTGAAT GTGGGAAAGC CTTCACTTCT AAGTCTCAAT TCAAAGAGCA TCAGCGAATT 1740
CACACGGGTG AGAAACCCTA TGTGTGCACT GAATGTGGGA AGGCCTTCAA CGGCAGGTCA 1800
AATTTCCATA AACATCAAAT AACTCACACT AGAGAGAGGC CTTTTGTCTG TTACAAATGT 1860
GGGAAGGCTT TTGTCCAGAA ATCAGAGTTG ATTACCCATC AAAGAACTCA CATGGGAGAG 1920
AAACCCTATG AATGCCTTGA CTGTGGGAAA TCGTTCAGTA AGAAACCACA ACTCAAGGTG 1980
CATCAGCGAA TTCACACGGG AGAAAGACCT TATGTGTGTT CTGAATGTGG AAAGGCCTTC 2040
AACAACAGGT CAAACTTCAA TAAACACCAA ACAACTCATA CCAGAGACAA ATCTTACAAA 2100
TGCAGTTATT CTGTGAAAGG CTTTACCAAG CAA 2133
```

(2) INFORMATION FOR SEQ ID NO:12:

(i) SEQUENCE CHARACTERISTICS:
(A) LENGTH: 3754 base pairs
(B) TYPE: nucleic acid
(C) STRANDEDNESS: single
(D) TOPOLOGY: linear (ii) MOLECULE TYPE: DNA(genomic)

(iii) HYPOTHETICAL: NO (iv) ANTI-SENSE: NO (vii) IMMEDIATE SOURCE:
(A) LIBRARY: Human fetal brain cDNA library
(B) CLONE: GEN-076C09

(ix) FEATURE:
(A) NAME/KEY: CDS
(B) LOCATION: 346..2478

(xi) SEQUENCE DESCRIPTION: SEQ ID NO:12:

```
GCTAAGCCTA TGTCGCTTAC TGGACGCTGA AGTGATTGGG AATATTAGCA GTGGGGGTTC   60
TGTAGGGTCA GGAAGGGGCG GCTGGCTTTG GGGGAGTGAT GAGGGGCTTG TTGGGGGTGG  120
GGGTGCGTGA TAAAGGGATT TCTCGGCTGA AGACGAGGCT GTGAGGCTTC TGCAGAACCC  180
CCAGGTCAGG CCACATCATT GAGGCTGCAG GATCTCTCTT CATAGCCCAG TACGACTCTC  240
CGCCGTGTCC CTGGTTGGAA AATCCAAACA CCTATCCAGC TTCTGGCTCC TGGGAAAAGT  300
GGAGTTGTCA GCAAGAGAGA CCGAGAGTAG AAGCCCAGAG TGGAG ATG CCT GCT    354
                                                  Met Pro Ala
                                                   1

GAT GTG AAT TTA TCC CAG AAG CCT CAG GTC CTG GGT CCA GAG AAG CAG  402
Asp Val Asn Leu Ser Gln Lys Pro Gln Val Leu Gly Pro Glu Lys Gln
     5                  10                  15

GAT GGA TCT TGC GAG GCA TCA GTG TCA TTT GAG GAC GTG ACC GTG GAC  450
Asp Gly Ser Cys Glu Ala Ser Val Ser Phe Glu Asp Val Thr Val Asp
 20                  25                  30                  35

TTC AGC AGG GAG GAG TGG CAG CAA CTG GAC CCT GCC CAG AGA TGC CTG  498
Phe Ser Arg Glu Glu Trp Gln Gln Leu Asp Pro Ala Gln Arg Cys Leu
```

-continued

```
                    40                        45                        50

TAC CGG GAT GTG ATG CTG GAG CTC TAT AGC CAT CTC TTC GCA GTG GGG       546
Tyr Arg Asp Val Met Leu Glu Leu Tyr Ser His Leu Phe Ala Val Gly
             55                      60                      65

TAT CAC ATT CCC AAC CCA GAG GTC ATC TTC AGA ATG CTA AAA GAA AAG       594
Tyr His Ile Pro Asn Pro Glu Val Ile Phe Arg Met Leu Lys Glu Lys
         70                      75                      80

GAG CCG CGT GTG GAG GAG GCT GAA GTC TCA CAT CAG AGG TGT CAA GAA       642
Glu Pro Arg Val Glu Glu Ala Glu Val Ser His Gln Arg Cys Gln Glu
     85                      90                      95

AGG GAG TTT GGG CTT GAA ATC CCA CAA AAG GAG ATT TCT AAG AAA GCT       690
Arg Glu Phe Gly Leu Glu Ile Pro Gln Lys Glu Ile Ser Lys Lys Ala
100                 105                 110                 115

TCA TTT CAA AAG GAT ATG GTA GGT GAG TTC ACA AGA GAT GGT TCA TGG       738
Ser Phe Gln Lys Asp Met Val Gly Glu Phe Thr Arg Asp Gly Ser Trp
                120                 125                 130

TGT TCC ATT TTA GAA GAA CTG AGG CTG GAT GCT GAC CGC ACA AAG AAA       786
Cys Ser Ile Leu Glu Glu Leu Arg Leu Asp Ala Asp Arg Thr Lys Lys
            135                 140                 145

GAT GAG CAA AAT CAA ATT CAA CCC ATG AGT CAC AGT GCT TTC TTC AAC       834
Asp Glu Gln Asn Gln Ile Gln Pro Met Ser His Ser Ala Phe Phe Asn
        150                 155                 160

AAG AAA ACA TTG AAC ACA GAA AGC AAT TGT GAA TAT AAG GAC CCT GGG       882
Lys Lys Thr Leu Asn Thr Glu Ser Asn Cys Glu Tyr Lys Asp Pro Gly
    165                 170                 175

AAA ATG ATT CGC ACG AGG CCC CAC CTT GCT TCT TCA CAG AAA CAA CCT       930
Lys Met Ile Arg Thr Arg Pro His Leu Ala Ser Ser Gln Lys Gln Pro
180                 185                 190                 195

CAG AAA TGT TGC TTA TTT ACA GAA AGT TTG AAG CTG AAC CTA GAA GTG       978
Gln Lys Cys Cys Leu Phe Thr Glu Ser Leu Lys Leu Asn Leu Glu Val
                200                 205                 210

AAC GGT CAG AAT GAA AGC AAT GAC ACA GAA CAG CTT GAT GAC GTT GTT      1026
Asn Gly Gln Asn Glu Ser Asn Asp Thr Glu Gln Leu Asp Asp Val Val
            215                 220                 225

GGG TCT GGT CAG CTA TTC AGC CAT AGC TCT TCT GAT GCC TGC AGC AAG      1074
Gly Ser Gly Gln Leu Phe Ser His Ser Ser Ser Asp Ala Cys Ser Lys
        230                 235                 240

AAT ATT CAT ACA GGA GAG ACA TTT TGC AAA GGT AAC CAG TGT AGA AAA      1122
Asn Ile His Thr Gly Glu Thr Phe Cys Lys Gly Asn Gln Cys Arg Lys
    245                 250                 255

GTC TGT GGC CAT AAA CAG TCA CTC AAG CAA CAT CAA ATT CAT ACT CAG      1170
Val Cys Gly His Lys Gln Ser Leu Lys Gln His Gln Ile His Thr Gln
260                 265                 270                 275

AAG AAA CCA GAT GGA TGT TCT GAA TGT GGG GGG AGC TTC ACC CAG AAG      1218
Lys Lys Pro Asp Gly Cys Ser Glu Cys Gly Gly Ser Phe Thr Gln Lys
                280                 285                 290

TCA CAC CTC TTT GCC CAA CAG AGA ATT CAT AGT GTA GGA AAC CTC CAT      1266
Ser His Leu Phe Ala Gln Gln Arg Ile His Ser Val Gly Asn Leu His
            295                 300                 305

GAA TGT GGC AAA TGT GGA AAA GCC TTC ATG CCA CAA CTA AAA CTC AGT      1314
Glu Cys Gly Lys Cys Gly Lys Ala Phe Met Pro Gln Leu Lys Leu Ser
        310                 315                 320

GTA TAT CTG ACA GAT CAT ACA GGT GAT ATA CCC TGT ATA TGC AAG GAA      1362
Val Tyr Leu Thr Asp His Thr Gly Asp Ile Pro Cys Ile Cys Lys Glu
    325                 330                 335

TGT GGG AAG GTC TTT ATT CAG AGA TCA GAA TTG CTT ACG CAC CAG AAA      1410
Cys Gly Lys Val Phe Ile Gln Arg Ser Glu Leu Leu Thr His Gln Lys
340                 345                 350                 355

ACA CAC ACT AGA AAG AAG CCC TAT AAA TGC CAT GAC TGT GGA AAA GCC      1458
Thr His Thr Arg Lys Lys Pro Tyr Lys Cys His Asp Cys Gly Lys Ala
```

-continued 360 365 370

TTT TTC CAG ATG TTA TCT CTC TTC AGA CAT CAG AGA ACT CAC AGT AGA 1506
Phe Phe Gln Met Leu Ser Leu Phe Arg His Gln Arg Thr His Ser Arg
375 380 385

GAA AAA CTC TAT GAA TGC AGT GAA TGT GGC AAA GGC TTC TCC CAA AAC 1554
Glu Lys Leu Tyr Glu Cys Ser Glu Cys Gly Lys Gly Phe Ser Gln Asn
390 395 400

TCA ACC CTC ATT ATA CAT CAG AAA ATT CAT ACT GGT GAG AGA CAG TAT 1602
Ser Thr Leu Ile Ile His Gln Lys Ile His Thr Gly Glu Arg Gln Tyr
405 410 415

GCA TGC AGT GAA TGT GGG AAA GCC TTT ACC CAG AAG TCA ACA CTC AGC 1650
Ala Cys Ser Glu Cys Gly Lys Ala Phe Thr Gln Lys Ser Thr Leu Ser
420 425 430 435

TTG CAC CAG AGA ATC CAC TCA GGG CAG AAG TCC TAT GTG TGT ATC GAA 1698
Leu His Gln Arg Ile His Ser Gly Gln Lys Ser Tyr Val Cys Ile Glu
440 445 450

TGC GGG CAG GCC TTC ATC CAG AAG GCA CAC CTG ATT GTC CAT CAA AGA 1746
Cys Gly Gln Ala Phe Ile Gln Lys Ala His Leu Ile Val His Gln Arg
455 460 465

AGC CAC ACA GGA GAA AAA CCT TAT CAG TGC CAC AAC TGT GGG AAA TCC 1794
Ser His Thr Gly Glu Lys Pro Tyr Gln Cys His Asn Cys Gly Lys Ser
470 475 480

TTC ATT TCC AAG TCA CAG CTT GAT ATA CAT CAT CGA ATT CAT ACA GGG 1842
Phe Ile Ser Lys Ser Gln Leu Asp Ile His His Arg Ile His Thr Gly
485 490 495

GAG AAA CCT TAT GAA TGC AGT GAC TGT GGA AAA ACC TTC ACC CAA AAG 1890
Glu Lys Pro Tyr Glu Cys Ser Asp Cys Gly Lys Thr Phe Thr Gln Lys
500 505 510 515

TCA CAC CTG AAT ATA CAC CAG AAA ATT CAT ACT GGA GAA AGA CAC CAT 1938
Ser His Leu Asn Ile His Gln Lys Ile His Thr Gly Glu Arg His His
520 525 530

GTA TGC AGT GAA TGC GGG AAA GCC TTC AAC CAG AAG TCA ATA CTC AGC 1986
Val Cys Ser Glu Cys Gly Lys Ala Phe Asn Gln Lys Ser Ile Leu Ser
535 540 545

ATG CAT CAG AGA ATT CAC ACC GGA GAG AAG CCT TAC AAA TGC AGT GAA 2034
Met His Gln Arg Ile His Thr Gly Glu Lys Pro Tyr Lys Cys Ser Glu
550 555 560

TGT GGG AAA GCC TTC ACT TCT AAG TCT CAA TTC AAA GAG CAT CAG CGA 2082
Cys Gly Lys Ala Phe Thr Ser Lys Ser Gln Phe Lys Glu His Gln Arg
565 570 575

ATT CAC ACG GGT GAG AAA CCC TAT GTG TGC ACT GAA TGT GGG AAG GCC 2130
Ile His Thr Gly Glu Lys Pro Tyr Val Cys Thr Glu Cys Gly Lys Ala
580 585 590 595

TTC AAC GGC AGG TCA AAT TTC CAT AAA CAT CAA ATA ACT CAC ACT AGA 2178
Phe Asn Gly Arg Ser Asn Phe His Lys His Gln Ile Thr His Thr Arg
600 605 610

GAG AGG CCT TTT GTC TGT TAC AAA TGT GGG AAG GCT TTT GTC CAG AAA 2226
Glu Arg Pro Phe Val Cys Tyr Lys Cys Gly Lys Ala Phe Val Gln Lys
615 620 625

TCA GAG TTG ATT ACC CAT CAA AGA ACT CAC ATG GGA GAG AAA CCC TAT 2274
Ser Glu Leu Ile Thr His Gln Arg Thr His Met Gly Glu Lys Pro Tyr
630 635 640

GAA TGC CTT GAC TGT GGG AAA TCG TTC AGT AAG AAA CCA CAA CTC AAG 2322
Glu Cys Leu Asp Cys Gly Lys Ser Phe Ser Lys Lys Pro Gln Leu Lys
645 650 655

GTG CAT CAG CGA ATT CAC ACG GGA GAA AGA CCT TAT GTG TGT TCT GAA 2370
Val His Gln Arg Ile His Thr Gly Glu Arg Pro Tyr Val Cys Ser Glu
660 665 670 675

TGT GGA AAG GCC TTC AAC AAC AGG TCA AAC TTC AAT AAA CAC CAA ACA 2418
Cys Gly Lys Ala Phe Asn Asn Arg Ser Asn Phe Asn Lys His Gln Thr

-continued

```
                        680                           685                           690

ACT CAT ACC AGA GAC AAA TCT TAC AAA TGC AGT TAT TCT GTG AAA GGC      2466
Thr His Thr Arg Asp Lys Ser Tyr Lys Cys Ser Tyr Ser Val Lys Gly
            695                     700                     705

TTT ACC AAG CAA TGAATTCCTA GTGCATCAGC ATATTCATAA ATGAAATATA         2518
Phe Thr Lys Gln
        710

CTCCGAGTTT CTTGAAGAAG AGAACATCTT CTCAGAATCA GGTCTAATTA TATGTTATTG   2578

AATTCATGCT TCAGAAAAAC TCTAGGGATG CACTGCATGT GTGAACACAT GATAAAAAAG   2638

TCATGCTTTA TTTTAGTGAG GGCAATTACA GAGAAAAGAG TAAGCAGAAA TGTCCTTCTG   2698

AGTACTGGCC TCATTAAGGA TTATAAATTT TCTCCCCGGG AAGAAACCCT GACTAACGCA   2758

TTGAGAAAAG CCTTTCTGTA AAGAATGGTA CAAGACAGGT TGTTACTCGA TTATTTATAG   2818

TAAAATATGT GGGAAATTAT ATCAATGATA ACCCTGTTTA TTGTGGGATA TCAATATTTT   2878

TAAAGTGCCA ACACAGTCAT GATAGGACAA TATTTTATGT GTGTGTGTGC GCCTTATGTA   2938

TATAAGCATA TATATAATAT ATAAGCATAT TATTATATAC AGGTTGAGTA TCCCTTCTCC   2998

AAAATGCCTG GGATCAGAAG CATTTTGGAT TTCAGATACT TACAGATTTT GGAATATTTG   3058

CATTATATTT ATTGGTTGAG CATCCCTAAT CTGAAAATCC AAGATTAAAT GCTCCAATTA   3118

GCATTTCCTT TGAGCGTCAT GTTAGAGTTC AAAAAGTTTC AGATTTTGGG TTTTCAGATT   3178

AGGAATACCC AACCTGTATG TACGTATATT TCTGTATCTA TGTATGTATA TATATGCATA   3238

TGCAGACATA TGTATATGGT CTGGTCAGCA TATGTGTATG TATGCGTATG TATGTATGTA   3298

TGTATGCCCT CAGTGCAGTG GGGTTTGCTG CAGAATTCAC TGCATAGCAG GAGATGTAAG   3358

CAGATGAGTT ATTTTTTAAG AGAATCTAAT CTAATTGTTT TTATAAAAAT TATTCCCTAT   3418

TGAATATTTA TATAATGAGG TTGTATCAAC AATGATTAAC TCCTTTATTA TACATACACA   3478

TGAATGTGCA TTTTTGGTAA ATGCATAAAT GAGATTCTAT AATGTTTACT GATCTTTATA   3538

TTACAGATTT TCTCTTCTTT TAGGATTAGC TCAGCTTGCC CCCCCTTTCC ATCTCCACCA   3598

TCTATAGTGA GCCTCTCCAT AATTAGTGCC AACCATTAGT CTCGTTCATA TTTTTACACC   3658

AGGAGTCAAC AAACTGTGCC ATTGGCCAAA TATGGCCTCC CAACTGTTTT TTTAAAATAA   3718

AGTTTTATTG GAACACAAAA AAAAAAAAAA AAAAAA                               3754
```

( 2 ) INFORMATION FOR SEQ ID NO:13:

( i ) SEQUENCE CHARACTERISTICS:
( A ) LENGTH: 389 amino acids
( B ) TYPE: amino acid
( D ) TOPOLOGY: linear ( i i ) MOLECULE TYPE: protein ( x i ) SEQUENCE DESCRIPTION: SEQ ID NO:13:

```
Met Ala Asp Pro Arg Asp Lys Ala Leu Gln Asp Tyr Arg Lys Lys Leu
 1               5                  10                  15

Leu Glu His Lys Glu Ile Asp Gly Arg Leu Lys Glu Leu Arg Glu Gln
            20                  25                  30

Leu Lys Glu Leu Thr Lys Gln Tyr Glu Lys Ser Glu Asn Asp Leu Lys
        35                  40                  45

Ala Leu Gln Ser Val Gly Gln Ile Val Gly Glu Val Leu Lys Gln Leu
    50                  55                  60

Thr Glu Glu Lys Phe Ile Val Lys Ala Thr Asn Gly Pro Arg Tyr Val
65                  70                  75                  80

Val Gly Cys Arg Arg Gln Leu Asp Lys Ser Lys Leu Lys Pro Gly Thr
```

-continued 85 90 95

Arg Val Ala Leu Asp Met Thr Thr Leu Thr Ile Met Arg Tyr Leu Pro
100 105 110

Arg Glu Val Asp Pro Leu Val Tyr Asn Met Ser His Glu Asp Pro Gly
115 120 125

Asn Val Ser Tyr Ser Glu Ile Gly Gly Leu Ser Glu Gln Ile Arg Glu
130 135 140

Leu Arg Glu Val Ile Glu Leu Pro Leu Thr Asn Pro Glu Leu Phe Gln
145 150 155 160

Arg Val Gly Ile Ile Pro Pro Lys Gly Cys Leu Leu Tyr Gly Pro Pro
165 170 175

Gly Thr Gly Lys Thr Leu Leu Ala Arg Ala Val Ala Ser Gln Leu Asp
180 185 190

Cys Asn Phe Leu Lys Val Val Ser Ser Ser Ile Val Asp Lys Tyr Ile
195 200 205

Gly Glu Ser Ala Arg Leu Ile Arg Glu Met Phe Asn Tyr Ala Arg Asp
210 215 220

His Gln Pro Cys Ile Ile Phe Met Asp Glu Ile Asp Ala Ile Gly Gly
225 230 235 240

Arg Arg Phe Ser Glu Gly Thr Ser Ala Asp Arg Glu Ile Gln Arg Thr
245 250 255

Leu Met Glu Leu Leu Asn Gln Met Asp Gly Phe Asp Thr Leu His Arg
260 265 270

Val Lys Met Thr Met Ala Thr Asn Arg Pro Asp Thr Leu Asp Pro Ala
275 280 285

Leu Leu Arg Pro Gly Arg Leu Asp Arg Lys Ile His Ile Asp Leu Pro
290 295 300

Asn Glu Gln Ala Arg Leu Asp Ile Leu Lys Ile His Ala Gly Pro Ile
305 310 315 320

Thr Lys His Gly Glu Ile Asp Tyr Glu Ala Ile Val Lys Leu Ser Asp
325 330 335

Gly Phe Asn Gly Ala Asp Leu Arg Asn Val Cys Thr Glu Ala Gly Met
340 345 350

Phe Ala Ile Arg Ala Asp His Asp Phe Val Val Gln Glu Asp Phe Met
355 360 365

Lys Ala Val Arg Lys Val Ala Asp Ser Lys Lys Leu Glu Ser Lys Leu
370 375 380

Asp Tyr Lys Pro Val
385

( 2 ) INFORMATION FOR SEQ ID NO:14:

( i ) SEQUENCE CHARACTERISTICS:
( A ) LENGTH: 1167 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:14:

ATGGCGGACC CTAGAGATAA GGCGCTTCAG GACTACCGCA AGAAGTTGCT TGAACACAAG 60

GAGATCGACG GCCGTCTTAA GGAGTTAAGG GAACAATTAA AAGAACTTAC CAAGCAGTAT 120

GAAAAGTCTG AAAATGATCT GAAGGCCCTA CAGAGTGTTG GGCAGATCGT GGGTGAAGTG 180

CTTAAACAGT TAACTGAAGA AAAATTCATT GTTAAAGCTA CCAATGGACC AAGATATGTT 240

-continued

GTGGGTTGTC GTCGACAGCT TGACAAAAGT AAGCTGAAGC CAGGAACAAG AGTTGCTTTG 300

GATATGACTA CACTAACTAT CATGAGATAT TTGCCGAGAG AGGTGGATCC ACTGGTTTAT 360

AACATGTCTC ATGAGGACCC TGGGAATGTT TCTTATTCTG AGATTGGAGG GCTATCAGAA 420

CAGATCCGGG AATTAAGAGA GGTGATAGAA TTACCTCTTA CAAACCCAGA GTTATTTCAG 480

CGTGTAGGAA TAATACCTCC AAAAGGCTGT TTGTTATATG GACCACCAGG TACGGGAAAA 540

ACACTCTTGG CACGAGCCGT TGCTAGCCAG CTGGACTGCA ATTTCTTAAA GGTTGTATCT 600

AGTTCTATTG TAGACAAGTA CATTGGTGAA AGTGCTCGTT TGATCAGAGA AATGTTTAAT 660

TATGCTAGAG ATCATCAACC ATGCATCATT TTTATGGATG AAATAGATGC TATTGGTGGT 720

CGTCGGTTTT CTGAGGGTAC TTCAGCTGAC AGAGAGATTC AGAGAACGTT AATGGAGTTA 780

CTGAATCAAA TGGATGGATT TGATACTCTG CATAGAGTTA AAATGACCAT GGCTACAAAC 840

AGACCAGATA CACTGGATCC TGCTTTGCTG CGTCCAGGAA GATTAGATAG AAAAATACAT 900

ATTGATTTGC CAAATGAACA AGCAAGATTA GACATACTGA AAATCCATGC AGGTCCCATT 960

ACAAAGCATG GTGAAATAGA TTATGAAGCA ATTGTGAAGC TTTCGGATGG CTTTAATGGA 1020

GCAGATCTGA GAAATGTTTG TACTGAAGCA GGTATGTTCG CAATTCGTGC TGATCATGAT 1080

TTTGTAGTAC AGGAAGACTT CATGAAAGCA GTCAGAAAAG TGGCTGATTC TAAGAAGCTG 1140

GAGTCTAAAT TGGACTACAA ACCTGTG 1167

( 2 ) INFORMATION FOR SEQ ID NO:15:

( i ) SEQUENCE CHARACTERISTICS:
( A ) LENGTH: 1566 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-331G07

( i x ) FEATURE:
( A ) NAME/KEY: CDS
( B ) LOCATION: 17..1183

( x i ) SEQUENCE DESCRIPTION: SEQ ID NO:15:

GAGACGGCTT CTCATC ATG GCG GAC CCT AGA GAT AAG GCG CTT CAG GAC 49
Met Ala Asp Pro Arg Asp Lys Ala Leu Gln Asp
1 5 10

TAC CGC AAG AAG TTG CTT GAA CAC AAG GAG ATC GAC GGC CGT CTT AAG 97
Tyr Arg Lys Lys Leu Leu Glu His Lys Glu Ile Asp Gly Arg Leu Lys
15 20 25

GAG TTA AGG GAA CAA TTA AAA GAA CTT ACC AAG CAG TAT GAA AAG TCT 145
Glu Leu Arg Glu Gln Leu Lys Glu Leu Thr Lys Gln Tyr Glu Lys Ser
30 35 40

GAA AAT GAT CTG AAG GCC CTA CAG AGT GTT GGG CAG ATC GTG GGT GAA 193
Glu Asn Asp Leu Lys Ala Leu Gln Ser Val Gly Gln Ile Val Gly Glu
45 50 55

GTG CTT AAA CAG TTA ACT GAA GAA AAA TTC ATT GTT AAA GCT ACC AAT 241
Val Leu Lys Gln Leu Thr Glu Glu Lys Phe Ile Val Lys Ala Thr Asn
60 65 70 75

GGA CCA AGA TAT GTT GTG GGT TGT CGT CGA CAG CTT GAC AAA AGT AAG 289
Gly Pro Arg Tyr Val Val Gly Cys Arg Arg Gln Leu Asp Lys Ser Lys
80 85 90

-continued

```
CTG AAG CCA GGA ACA AGA GTT GCT TTG GAT ATG ACT ACA CTA ACT ATC      337
Leu Lys Pro Gly Thr Arg Val Ala Leu Asp Met Thr Thr Leu Thr Ile
             95                 100                 105

ATG AGA TAT TTG CCG AGA GAG GTG GAT CCA CTG GTT TAT AAC ATG TCT      385
Met Arg Tyr Leu Pro Arg Glu Val Asp Pro Leu Val Tyr Asn Met Ser
        110                 115                 120

CAT GAG GAC CCT GGG AAT GTT TCT TAT TCT GAG ATT GGA GGG CTA TCA      433
His Glu Asp Pro Gly Asn Val Ser Tyr Ser Glu Ile Gly Gly Leu Ser
    125                 130                 135

GAA CAG ATC CGG GAA TTA AGA GAG GTG ATA GAA TTA CCT CTT ACA AAC      481
Glu Gln Ile Arg Glu Leu Arg Glu Val Ile Glu Leu Pro Leu Thr Asn
140                 145                 150                 155

CCA GAG TTA TTT CAG CGT GTA GGA ATA ATA CCT CCA AAA GGC TGT TTG      529
Pro Glu Leu Phe Gln Arg Val Gly Ile Ile Pro Pro Lys Gly Cys Leu
                160                 165                 170

TTA TAT GGA CCA CCA GGT ACG GGA AAA ACA CTC TTG GCA CGA GCC GTT      577
Leu Tyr Gly Pro Pro Gly Thr Gly Lys Thr Leu Leu Ala Arg Ala Val
            175                 180                 185

GCT AGC CAG CTG GAC TGC AAT TTC TTA AAG GTT GTA TCT AGT TCT ATT      625
Ala Ser Gln Leu Asp Cys Asn Phe Leu Lys Val Val Ser Ser Ser Ile
        190                 195                 200

GTA GAC AAG TAC ATT GGT GAA AGT GCT CGT TTG ATC AGA GAA ATG TTT      673
Val Asp Lys Tyr Ile Gly Glu Ser Ala Arg Leu Ile Arg Glu Met Phe
    205                 210                 215

AAT TAT GCT AGA GAT CAT CAA CCA TGC ATC ATT TTT ATG GAT GAA ATA      721
Asn Tyr Ala Arg Asp His Gln Pro Cys Ile Ile Phe Met Asp Glu Ile
220                 225                 230                 235

GAT GCT ATT GGT GGT CGT CGG TTT TCT GAG GGT ACT TCA GCT GAC AGA      769
Asp Ala Ile Gly Gly Arg Arg Phe Ser Glu Gly Thr Ser Ala Asp Arg
                240                 245                 250

GAG ATT CAG AGA ACG TTA ATG GAG TTA CTG AAT CAA ATG GAT GGA TTT      817
Glu Ile Gln Arg Thr Leu Met Glu Leu Leu Asn Gln Met Asp Gly Phe
            255                 260                 265

GAT ACT CTG CAT AGA GTT AAA ATG ACC ATG GCT ACA AAC AGA CCA GAT      865
Asp Thr Leu His Arg Val Lys Met Thr Met Ala Thr Asn Arg Pro Asp
        270                 275                 280

ACA CTG GAT CCT GCT TTG CTG CGT CCA GGA AGA TTA GAT AGA AAA ATA      913
Thr Leu Asp Pro Ala Leu Leu Arg Pro Gly Arg Leu Asp Arg Lys Ile
    285                 290                 295

CAT ATT GAT TTG CCA AAT GAA CAA GCA AGA TTA GAC ATA CTG AAA ATC      961
His Ile Asp Leu Pro Asn Glu Gln Ala Arg Leu Asp Ile Leu Lys Ile
300                 305                 310                 315

CAT GCA GGT CCC ATT ACA AAG CAT GGT GAA ATA GAT TAT GAA GCA ATT     1009
His Ala Gly Pro Ile Thr Lys His Gly Glu Ile Asp Tyr Glu Ala Ile
                320                 325                 330

GTG AAG CTT TCG GAT GGC TTT AAT GGA GCA GAT CTG AGA AAT GTT TGT     1057
Val Lys Leu Ser Asp Gly Phe Asn Gly Ala Asp Leu Arg Asn Val Cys
            335                 340                 345

ACT GAA GCA GGT ATG TTC GCA ATT CGT GCT GAT CAT GAT TTT GTA GTA     1105
Thr Glu Ala Gly Met Phe Ala Ile Arg Ala Asp His Asp Phe Val Val
        350                 355                 360

CAG GAA GAC TTC ATG AAA GCA GTC AGA AAA GTG GCT GAT TCT AAG AAG     1153
Gln Glu Asp Phe Met Lys Ala Val Arg Lys Val Ala Asp Ser Lys Lys
    365                 370                 375

CTG GAG TCT AAA TTG GAC TAC AAA CCT GTG TAATTTACTG TAAGATTTTT       1203
Leu Glu Ser Lys Leu Asp Tyr Lys Pro Val
380                 385

GATGGCTGCA TGACAGATGT TGGCTTATTG TAAAAATAAA GTTAAAGAAA ATAATGTATG   1263

TATTGGCAAT GATGTCATTA AAAGTATATG AATAAAAATA TGAGTAACAT CATAAAAATT   1323
```

-continued

| | | | | | | |
|---|---|---|---|---|---|---|
| AGTAATTCAA | CTTTTAAGAT | ACAGAAGAAA | TTTGTATGTT | TGTTAAAGTT | GCATTTATTG | 1383 |
| CAGCAAGTTA | CAAAGGGAAA | GTGTTGAAGC | TTTTCATATT | TGCTGCGTGA | GCATTTTGTA | 1443 |
| AAATATTGAA | AGTGGTTTGA | GATAGTGGTA | TAAGAAAGCA | TTTCTTATGA | CTTATTTTGT | 1503 |
| ATCATTTGTT | TTCCTCATCT | AAAAAGTTGA | ATAAAATCTG | TTTGATTCAG | TTCTCCTAAA | 1563 |
| AAA | | | | | | 1566 |

( 2 ) INFORMATION FOR SEQ ID NO:16:

( i ) SEQUENCE CHARACTERISTICS:
( A ) LENGTH: 223 amino acids
( B ) TYPE: amino acid
( D ) TOPOLOGY: linear ( i i ) MOLECULE TYPE: protein ( x i ) SEQUENCE DESCRIPTION: SEQ ID NO:16:

Met Ser Asp Glu Glu Ala Arg Gln Ser Gly Gly Ser Ser Gln Ala Gly
1 5 10 15

Val Val Thr Val Ser Asp Val Gln Glu Leu Met Arg Arg Lys Glu Glu
20 25 30

Ile Glu Ala Gln Ile Lys Ala Asn Tyr Asp Val Leu Glu Ser Gln Lys
35 40 45

Gly Ile Gly Met Asn Glu Pro Leu Val Asp Cys Glu Gly Tyr Pro Arg
50 55 60

Ser Asp Val Asp Leu Tyr Gln Val Arg Thr Ala Arg His Asn Ile Ile
65 70 75 80

Cys Leu Gln Asn Asp His Lys Ala Val Met Lys Gln Val Glu Glu Ala
85 90 95

Leu His Gln Leu His Ala Arg Asp Lys Glu Lys Gln Ala Arg Asp Met
100 105 110

Ala Glu Ala His Lys Glu Ala Met Ser Arg Lys Leu Gly Gln Ser Glu
115 120 125

Ser Gln Gly Pro Pro Arg Ala Phe Ala Lys Val Asn Ser Ile Ser Pro
130 135 140

Gly Ser Pro Ala Ser Ile Ala Gly Leu Gln Val Asp Asp Glu Ile Val
145 150 155 160

Glu Phe Gly Ser Val Asn Thr Gln Asn Phe Gln Ser Leu His Asn Ile
165 170 175

Gly Ser Val Val Gln His Ser Glu Gly Lys Pro Leu Asn Val Thr Val
180 185 190

Ile Arg Arg Gly Glu Lys His Gln Leu Arg Leu Val Pro Thr Arg Trp
195 200 205

Ala Gly Lys Gly Leu Leu Gly Cys Asn Ile Ile Pro Leu Gln Arg
210 215 220

( 2 ) INFORMATION FOR SEQ ID NO:17:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:17:

| | | | | | | |
|---|---|---|---|---|---|---|
| ATGTCCGACG | AGGAAGCGAG | GCAGAGCGGA | GGCTCCTCGC | AGGCCGGCGT | CGTGACTGTC | 60 |

-continued

AGCGACGTCC AGGAGCTGAT GCGGCGCAAG GAGGAGATAG AAGCGCAGAT CAAGGCCAAC 120

TATGACGTGC TGGAAAGCCA AAAAGGCATT GGGATGAACG AGCCGCTGGT GGACTGTGAG 180

GGCTACCCCC GGTCAGACGT GGACCTGTAC CAAGTCCGCA CCGCCAGGCA CAACATCATA 240

TGCCTGCAGA ATGATCACAA GGCAGTGATG AAGCAGGTGG AGGAGGCCCT GCACCAGCTG 300

CACGCTCGCG ACAAGGAGAA GCAGGCCCGG GACATGGCTG AGGCCCACAA AGAGGCCATG 360

AGCCGCAAAC TGGGTCAGAG TGAGAGCCAG GGCCCTCCAC GGGCCTTCGC CAAAGTGAAC 420

AGCATCAGCC CCGGCTCCCC AGCCAGCATC GCGGGTCTGC AAGTGGATGA TGAGATTGTG 480

GAGTTCGGCT CTGTGAACAC CCAGAACTTC CAGTCACTGC ATAACATTGG CAGTGTGGTG 540

CAGCACAGTG AGGGGAAGCC CCTGAATGTG ACAGTGATCC GCAGGGGGGA AAAACACCAG 600

CTTAGACTTG TTCCAACACG CTGGGCAGGA AAAGGACTGC TGGGCTGCAA CATTATTCCT 660

CTGCAAAGA 669

( 2 ) INFORMATION FOR SEQ ID NO:18:

( i ) SEQUENCE CHARACTERISTICS:
( A ) LENGTH: 1128 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-163D09

( i x ) FEATURE:
( A ) NAME/KEY: CDS
( B ) LOCATION: 125..793

( x i ) SEQUENCE DESCRIPTION: SEQ ID NO:18:

ACTGTTCTCG CGTTCGCGGA CGGCTGTGGT GTTTTGGCGC ATGGGCGGAG CGTAGTTACG 60

GTCGACTGGG GCGTCGTCCC TAGCCCGGGA GCCGGGTCTC TGGAGTCGCG GCCCGGGGTT 120

CACG ATG TCC GAC GAG GAA GCG AGG CAG AGC GGA GGC TCC TCG CAG GCC 169
Met Ser Asp Glu Glu Ala Arg Gln Ser Gly Gly Ser Ser Gln Ala
1 5 10 15

GGC GTC GTG ACT GTC AGC GAC GTC CAG GAG CTG ATG CGG CGC AAG GAG 217
Gly Val Val Thr Val Ser Asp Val Gln Glu Leu Met Arg Arg Lys Glu
20 25 30

GAG ATA GAA GCG CAG ATC AAG GCC AAC TAT GAC GTG CTG GAA AGC CAA 265
Glu Ile Glu Ala Gln Ile Lys Ala Asn Tyr Asp Val Leu Glu Ser Gln
35 40 45

AAA GGC ATT GGG ATG AAC GAG CCG CTG GTG GAC TGT GAG GGC TAC CCC 313
Lys Gly Ile Gly Met Asn Glu Pro Leu Val Asp Cys Glu Gly Tyr Pro
50 55 60

CGG TCA GAC GTG GAC CTG TAC CAA GTC CGC ACC GCC AGG CAC AAC ATC 361
Arg Ser Asp Val Asp Leu Tyr Gln Val Arg Thr Ala Arg His Asn Ile
65 70 75

ATA TGC CTG CAG AAT GAT CAC AAG GCA GTG ATG AAG CAG GTG GAG GAG 409
Ile Cys Leu Gln Asn Asp His Lys Ala Val Met Lys Gln Val Glu Glu
80 85 90 95

GCC CTG CAC CAG CTG CAC GCT CGC GAC AAG GAG AAG CAG GCC CGG GAC 457
Ala Leu His Gln Leu His Ala Arg Asp Lys Glu Lys Gln Ala Arg Asp
100 105 110

ATG GCT GAG GCC CAC AAA GAG GCC ATG AGC CGC AAA CTG GGT CAG AGT 505

-continued

```
Met Ala Glu Ala His Lys Glu Ala Met Ser Arg Lys Leu Gly Gln Ser
            115                 120                 125

GAG AGC CAG GGC CCT CCA CGG GCC TTC GCC AAA GTG AAC AGC ATC AGC     553
Glu Ser Gln Gly Pro Pro Arg Ala Phe Ala Lys Val Asn Ser Ile Ser
        130                 135                 140

CCC GGC TCC CCA GCC AGC ATC GCG GGT CTG CAA GTG GAT GAT GAG ATT     601
Pro Gly Ser Pro Ala Ser Ile Ala Gly Leu Gln Val Asp Asp Glu Ile
    145                 150                 155

GTG GAG TTC GGC TCT GTG AAC ACC CAG AAC TTC CAG TCA CTG CAT AAC     649
Val Glu Phe Gly Ser Val Asn Thr Gln Asn Phe Gln Ser Leu His Asn
160                 165                 170                 175

ATT GGC AGT GTG GTG CAG CAC AGT GAG GGG AAG CCC CTG AAT GTG ACA     697
Ile Gly Ser Val Val Gln His Ser Glu Gly Lys Pro Leu Asn Val Thr
                180                 185                 190

GTG ATC CGC AGG GGG GAA AAA CAC CAG CTT AGA CTT GTT CCA ACA CGC     745
Val Ile Arg Arg Gly Glu Lys His Gln Leu Arg Leu Val Pro Thr Arg
            195                 200                 205

TGG GCA GGA AAA GGA CTG CTG GGC TGC AAC ATT ATT CCT CTG CAA AGA     793
Trp Ala Gly Lys Gly Leu Leu Gly Cys Asn Ile Ile Pro Leu Gln Arg
        210                 215                 220

TGATTGTCCC TGGGGAACAG TAACAGGAAA GCATCTTCCC TTGCCCTGGA CTTGGGTCTA    853

GGGATTTCCA ACTTGTCTTC TCTCCCTGAA GCATAAGGAT CTGGAAGAGG CTTGTAACCT    913

GAACTTCTGT GTGGTGGCAG TACTGTGGCC CACCAGTGTA ATCTCCCTGG ATTAAGGCAT    973

TCTTAAAAAC TTAGGCTTGG CCTCTTTCAC AAATTAGGCC ACGGCCCTAA ATAGGAATTC   1033

CCTGGATTGT GGGCAAGTGG GCGGAAGTTA TTCTGGCAGG TACTGGTGTG ATTATTATTA   1093

TTATTTTTAA TAAAGAGTTT TACAGTGCTG ATATG                              1128
```

( 2 ) INFORMATION FOR SEQ ID NO:19:

( i ) SEQUENCE CHARACTERISTICS:
( A ) LENGTH: 506 amino acids
( B ) TYPE: amino acid
( D ) TOPOLOGY: linear ( i i ) MOLECULE TYPE: protein ( x i ) SEQUENCE DESCRIPTION: SEQ ID NO:19:

```
Met Ala Glu Ala Asp Phe Lys Met Val Ser Glu Pro Val Ala His Gly
  1               5                  10                  15

Val Ala Glu Glu Glu Met Ala Ser Ser Thr Ser Asp Ser Gly Glu Glu
             20                  25                  30

Ser Asp Ser Ser Ser Ser Ser Ser Ser Thr Ser Asp Ser Ser Ser Ser
         35                  40                  45

Ser Ser Thr Ser Gly Ser Ser Ser Gly Ser Gly Ser Ser Ser Ser Ser
     50                  55                  60

Ser Gly Ser Thr Ser Ser Arg Ser Arg Leu Tyr Arg Lys Lys Arg Val
 65                  70                  75                  80

Pro Glu Pro Ser Arg Arg Ala Arg Arg Ala Pro Leu Gly Thr Asn Phe
                 85                  90                  95

Val Asp Arg Leu Pro Gln Ala Val Arg Asn Arg Val Gln Ala Leu Arg
            100                 105                 110

Asn Ile Gln Asp Glu Cys Asp Lys Val Asp Thr Leu Phe Leu Lys Ala
        115                 120                 125

Ile His Asp Leu Glu Arg Lys Tyr Ala Glu Leu Asn Lys Pro Leu Tyr
    130                 135                 140

Asp Arg Arg Phe Gln Ile Ile Asn Ala Glu Tyr Glu Pro Thr Glu Glu
145                 150                 155                 160
```

```
Glu Cys Glu Trp Asn Ser Glu Asp Glu Glu Phe Ser Ser Asp Glu Glu
                165                 170                 175

Val Gln Asp Asn Thr Pro Ser Glu Met Pro Pro Leu Glu Gly Glu Glu
            180                 185                 190

Glu Glu Asn Pro Lys Glu Asn Pro Glu Val Lys Ala Glu Glu Lys Glu
        195                 200                 205

Val Pro Lys Glu Ile Pro Glu Val Lys Asp Glu Glu Lys Glu Val Ala
    210                 215                 220

Lys Glu Ile Pro Glu Val Lys Ala Glu Glu Lys Ala Asp Ser Lys Asp
225                 230                 235                 240

Cys Met Glu Ala Thr Pro Glu Val Lys Glu Asp Pro Lys Glu Val Pro
                245                 250                 255

Gln Val Lys Ala Asp Asp Lys Glu Gln Pro Lys Ala Thr Glu Ala Lys
            260                 265                 270

Ala Arg Ala Ala Val Arg Glu Thr His Lys Arg Val Pro Glu Glu Arg
        275                 280                 285

Leu Arg Asp Ser Val Asp Leu Lys Arg Ala Arg Lys Gly Lys Pro Lys
    290                 295                 300

Arg Glu Asp Pro Lys Gly Ile Pro Asp Tyr Trp Leu Ile Val Leu Lys
305                 310                 315                 320

Asn Val Asp Lys Leu Gly Pro Met Ile Gln Lys Tyr Asp Glu Pro Ile
                325                 330                 335

Leu Lys Phe Leu Ser Asp Val Ser Leu Lys Phe Ser Lys Pro Gly Gln
            340                 345                 350

Pro Val Ser Tyr Thr Phe Glu Phe His Phe Leu Pro Asn Pro Tyr Phe
        355                 360                 365

Arg Asn Glu Val Leu Val Lys Thr Tyr Ile Ile Lys Ala Lys Pro Asp
    370                 375                 380

His Asn Asp Pro Phe Phe Ser Trp Gly Trp Glu Ile Glu Asp Cys Lys
385                 390                 395                 400

Gly Cys Lys Ile Asp Arg Arg Arg Gly Lys Asp Val Thr Val Thr Thr
                405                 410                 415

Thr Gln Ser Arg Thr Thr Ala Thr Gly Glu Ile Glu Ile Gln Pro Arg
            420                 425                 430

Val Val Pro Asn Ala Ser Phe Phe Asn Phe Phe Ser Pro Pro Glu Ile
        435                 440                 445

Pro Met Ile Gly Lys Leu Glu Pro Arg Glu Asp Ala Ile Leu Asp Glu
    450                 455                 460

Asp Phe Glu Ile Gly Gln Ile Leu His Asp Asn Val Ile Leu Lys Ser
465                 470                 475                 480

Ile Tyr Tyr Tyr Thr Gly Glu Val Asn Gly Thr Tyr Tyr Gln Phe Gly
                485                 490                 495

Lys His Tyr Gly Asn Lys Lys Tyr Arg Lys
            500                 505
```

( 2 ) INFORMATION FOR SEQ ID NO:20:

( i ) SEQUENCE CHARACTERISTICS:

( A ) LENGTH: 1518 base pairs ( B ) TYPE: nucleic acid ( C ) STRANDEDNESS: single ( D ) TOPOLOGY: linear ( i i ) MOLECULE TYPE: DNA(genomic)

( x i ) SEQUENCE DESCRIPTION: SEQ ID NO:20:

-continued

```
ATGGCAGAAG CAGATTTTAA AATGGTCTCG GAACCTGTCG CCCATGGGGT TGCCGAAGAG   60
GAGATGGCTA GCTCGACTAG TGATTCTGGG GAAGAATCTG ACAGCAGTAG CTCTAGCAGC  120
AGCACTAGTG ACAGCAGCAG CAGCAGCAGC ACTAGTGGCA GCAGCAGCGG CAGCGGCAGC  180
AGCAGCAGCA GCAGCGGCAG CACTAGCAGC CGCAGCCGCT TGTATAGAAA GAAGAGGGTA  240
CCTGAGCCTT CCAGAAGGGC GCGGCGGGCC CCGTTGGGAA CAAATTTCGT GGATAGGCTG  300
CCTCAGGCAG TTAGAAATCG TGTGCAAGCG CTTAGAAACA TTCAAGATGA ATGTGACAAG  360
GTAGATACCC TGTTCTTAAA AGCAATTCAT GATCTTGAAA GAAAATATGC TGAACTCAAC  420
AAGCCTCTGT ATGATAGGCG GTTTCAAATC ATCAATGCAG AATACGAGCC TACAGAAGAA  480
GAATGTGAAT GGAATTCAGA GGATGAGGAG TTCAGCAGTG ATGAGGAGGT GCAGGATAAC  540
ACCCCTAGTG AAATGCCTCC CTTAGAGGGT GAGGAAGAAG AAAACCCTAA AGAAAACCCA  600
GAGGTGAAAG CTGAAGAGAA GGAAGTTCCT AAAGAAATTC CTGAGGTGAA GGATGAAGAA  660
AAGGAAGTTG CTAAAGAAAT TCCTGAGGTA AAGGCTGAAG AAAAAGCAGA TTCTAAAGAC  720
TGTATGGAGG CAACCCCTGA AGTAAAAGAA GATCCTAAAG AAGTCCCCCA GGTAAAGGCA  780
GATGATAAAG AACAGCCTAA AGCAACAGAG GCTAAGGCAA GGGCTGCAGT AAGAGAGACT  840
CATAAAAGAG TTCCTGAGGA AAGGCTTCGG GACAGTGTAG ATCTTAAAAG AGCTAGGAAG  900
GGAAAGCCTA AAAGAGAAGA CCCTAAAGGC ATTCCTGACT ATTGGCTGAT TGTTTTAAAG  960
AATGTTGACA AGCTCGGGCC TATGATTCAG AAGTATGATG AGCCCATTCT GAAGTTCTTG 1020
TCGGATGTTA GCCTGAAGTT CTCAAAACCT GGCCAGCCTG TAAGTTACAC CTTTGAATTT 1080
CATTTTCTAC CCAACCCATA CTTCAGAAAT GAGGTGCTGG TGAAGACATA TATAATAAAG 1140
GCAAAACCAG ATCACAATGA TCCCTTCTTT TCTTGGGGAT GGGAAATTGA AGATTGCAAA 1200
GGCTGCAAGA TAGACCGGAG AAGAGGAAAA GATGTTACTG TGACAACTAC CCAGAGTCGC 1260
ACAACTGCTA CTGGAGAAAT TGAAATCCAG CCAAGAGTGG TTCCTAATGC ATCATTCTTC 1320
AACTTCTTTA GTCCTCCTGA GATTCCTATG ATTGGGAAGC TGGAACCACG AGAAGATGCT 1380
ATCCTGGATG AGGACTTTGA AATTGGGCAG ATTTTACATG ATAATGTCAT CCTGAAATCA 1440
ATCTATTACT ATACTGGAGA AGTCAATGGT ACCTACTATC AATTTGGCAA ACATTATGGA 1500
AACAAGAAAT ACAGAAAA                                               1518
```

( 2 ) INFORMATION FOR SEQ ID NO:21:

( i ) SEQUENCE CHARACTERISTICS:
( A ) LENGTH: 2636 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-078D05

( i x ) FEATURE:
( A ) NAME/KEY: CDS
( B ) LOCATION: 266..1783

( x i ) SEQUENCE DESCRIPTION: SEQ ID NO:21:

```
GATTCGGCTG CGGTACATCT CGGCACTCTA GCTGCAGCCG GGAGAGGCCT TGCCGCCACC   60
GCTGTCGCCC AAGCCTCCAC TGCCGCTGCC ACCTCAGCGC CGGCCTCTGC ATCCCCAGCT  120
```

-continued

```
CCAGCTCCGC TCTGCGCCGC TGCTGCCATC GCCGCTGCCA CCTCCGCAGC CCGGGCCTCC     180

GCCGCCGCCA CCCAAGCATC CGTGAGTCAT TTTCTGCCCA TCTCTGGTCG CGCGGTCTCC     240

CTGGTAGAGT TTGTAGGCTT GCAAG ATG GCA GAA GCA GAT TTT AAA ATG GTC       292
                            Met Ala Glu Ala Asp Phe Lys Met Val
                              1               5

TCG GAA CCT GTC GCC CAT GGG GTT GCC GAA GAG GAG ATG GCT AGC TCG       340
Ser Glu Pro Val Ala His Gly Val Ala Glu Glu Glu Met Ala Ser Ser
 10                  15                  20                  25

ACT AGT GAT TCT GGG GAA GAA TCT GAC AGC AGT AGC TCT AGC AGC AGC       388
Thr Ser Asp Ser Gly Glu Glu Ser Asp Ser Ser Ser Ser Ser Ser Ser
                 30                  35                  40

ACT AGT GAC AGC AGC AGC AGC AGC AGC ACT AGT GGC AGC AGC AGC GGC       436
Thr Ser Asp Ser Ser Ser Ser Ser Ser Thr Ser Gly Ser Ser Ser Gly
             45                  50                  55

AGC GGC AGC AGC AGC AGC AGC AGC GGC AGC ACT AGC AGC CGC AGC CGC       484
Ser Gly Ser Ser Ser Ser Ser Ser Gly Ser Thr Ser Ser Arg Ser Arg
         60                  65                  70

TTG TAT AGA AAG AAG AGG GTA CCT GAG CCT TCC AGA AGG GCG CGG CGG       532
Leu Tyr Arg Lys Lys Arg Val Pro Glu Pro Ser Arg Arg Ala Arg Arg
     75                  80                  85

GCC CCG TTG GGA ACA AAT TTC GTG GAT AGG CTG CCT CAG GCA GTT AGA       580
Ala Pro Leu Gly Thr Asn Phe Val Asp Arg Leu Pro Gln Ala Val Arg
 90                  95                 100                 105

AAT CGT GTG CAA GCG CTT AGA AAC ATT CAA GAT GAA TGT GAC AAG GTA       628
Asn Arg Val Gln Ala Leu Arg Asn Ile Gln Asp Glu Cys Asp Lys Val
                110                 115                 120

GAT ACC CTG TTC TTA AAA GCA ATT CAT GAT CTT GAA AGA AAA TAT GCT       676
Asp Thr Leu Phe Leu Lys Ala Ile His Asp Leu Glu Arg Lys Tyr Ala
            125                 130                 135

GAA CTC AAC AAG CCT CTG TAT GAT AGG CGG TTT CAA ATC ATC AAT GCA       724
Glu Leu Asn Lys Pro Leu Tyr Asp Arg Arg Phe Gln Ile Ile Asn Ala
        140                 145                 150

GAA TAC GAG CCT ACA GAA GAA GAA TGT GAA TGG AAT TCA GAG GAT GAG       772
Glu Tyr Glu Pro Thr Glu Glu Glu Cys Glu Trp Asn Ser Glu Asp Glu
    155                 160                 165

GAG TTC AGC AGT GAT GAG GAG GTG CAG GAT AAC ACC CCT AGT GAA ATG       820
Glu Phe Ser Ser Asp Glu Glu Val Gln Asp Asn Thr Pro Ser Glu Met
170                 175                 180                 185

CCT CCC TTA GAG GGT GAG GAA GAA GAA AAC CCT AAA GAA AAC CCA GAG       868
Pro Pro Leu Glu Gly Glu Glu Glu Glu Asn Pro Lys Glu Asn Pro Glu
                190                 195                 200

GTG AAA GCT GAA GAG AAG GAA GTT CCT AAA GAA ATT CCT GAG GTG AAG       916
Val Lys Ala Glu Glu Lys Glu Val Pro Lys Glu Ile Pro Glu Val Lys
            205                 210                 215

GAT GAA GAA AAG GAA GTT GCT AAA GAA ATT CCT GAG GTA AAG GCT GAA       964
Asp Glu Glu Lys Glu Val Ala Lys Glu Ile Pro Glu Val Lys Ala Glu
        220                 225                 230

GAA AAA GCA GAT TCT AAA GAC TGT ATG GAG GCA ACC CCT GAA GTA AAA      1012
Glu Lys Ala Asp Ser Lys Asp Cys Met Glu Ala Thr Pro Glu Val Lys
    235                 240                 245

GAA GAT CCT AAA GAA GTC CCC CAG GTA AAG GCA GAT GAT AAA GAA CAG      1060
Glu Asp Pro Lys Glu Val Pro Gln Val Lys Ala Asp Asp Lys Glu Gln
250                 255                 260                 265

CCT AAA GCA ACA GAG GCT AAG GCA AGG GCT GCA GTA AGA GAG ACT CAT      1108
Pro Lys Ala Thr Glu Ala Lys Ala Arg Ala Ala Val Arg Glu Thr His
                270                 275                 280

AAA AGA GTT CCT GAG GAA AGG CTT CGG GAC AGT GTA GAT CTT AAA AGA      1156
Lys Arg Val Pro Glu Glu Arg Leu Arg Asp Ser Val Asp Leu Lys Arg
            285                 290                 295
```

-continued

GCT AGG AAG GGA AAG CCT AAA AGA GAA GAC CCT AAA GGC ATT CCT GAC 1204
Ala Arg Lys Gly Lys Pro Lys Arg Glu Asp Pro Lys Gly Ile Pro Asp
        300                 305                 310

TAT TGG CTG ATT GTT TTA AAG AAT GTT GAC AAG CTC GGG CCT ATG ATT 1252
Tyr Trp Leu Ile Val Leu Lys Asn Val Asp Lys Leu Gly Pro Met Ile
    315                 320                 325

CAG AAG TAT GAT GAG CCC ATT CTG AAG TTC TTG TCG GAT GTT AGC CTG 1300
Gln Lys Tyr Asp Glu Pro Ile Leu Lys Phe Leu Ser Asp Val Ser Leu
330                 335                 340                 345

AAG TTC TCA AAA CCT GGC CAG CCT GTA AGT TAC ACC TTT GAA TTT CAT 1348
Lys Phe Ser Lys Pro Gly Gln Pro Val Ser Tyr Thr Phe Glu Phe His
                350                 355                 360

TTT CTA CCC AAC CCA TAC TTC AGA AAT GAG GTG CTG GTG AAG ACA TAT 1396
Phe Leu Pro Asn Pro Tyr Phe Arg Asn Glu Val Leu Val Lys Thr Tyr
            365                 370                 375

ATA ATA AAG GCA AAA CCA GAT CAC AAT GAT CCC TTC TTT TCT TGG GGA 1444
Ile Ile Lys Ala Lys Pro Asp His Asn Asp Pro Phe Phe Ser Trp Gly
        380                 385                 390

TGG GAA ATT GAA GAT TGC AAA GGC TGC AAG ATA GAC CGG AGA AGA GGA 1492
Trp Glu Ile Glu Asp Cys Lys Gly Cys Lys Ile Asp Arg Arg Arg Gly
    395                 400                 405

AAA GAT GTT ACT GTG ACA ACT ACC CAG AGT CGC ACA ACT GCT ACT GGA 1540
Lys Asp Val Thr Val Thr Thr Thr Gln Ser Arg Thr Thr Ala Thr Gly
410                 415                 420                 425

GAA ATT GAA ATC CAG CCA AGA GTG GTT CCT AAT GCA TCA TTC TTC AAC 1588
Glu Ile Glu Ile Gln Pro Arg Val Val Pro Asn Ala Ser Phe Phe Asn
                430                 435                 440

TTC TTT AGT CCT CCT GAG ATT CCT ATG ATT GGG AAG CTG GAA CCA CGA 1636
Phe Phe Ser Pro Pro Glu Ile Pro Met Ile Gly Lys Leu Glu Pro Arg
            445                 450                 455

GAA GAT GCT ATC CTG GAT GAG GAC TTT GAA ATT GGG CAG ATT TTA CAT 1684
Glu Asp Ala Ile Leu Asp Glu Asp Phe Glu Ile Gly Gln Ile Leu His
        460                 465                 470

GAT AAT GTC ATC CTG AAA TCA ATC TAT TAC TAT ACT GGA GAA GTC AAT 1732
Asp Asn Val Ile Leu Lys Ser Ile Tyr Tyr Tyr Thr Gly Glu Val Asn
    475                 480                 485

GGT ACC TAC TAT CAA TTT GGC AAA CAT TAT GGA AAC AAG AAA TAC AGA 1780
Gly Thr Tyr Tyr Gln Phe Gly Lys His Tyr Gly Asn Lys Lys Tyr Arg
490                 495                 500                 505

AAA TAAGTCAATC TGAAAGATTT TTCAAGAATC TTAAAATCTC AAGAAGTGAA 1833
Lys

GCAGATTCAT ACAGCCTTGA AAAAAGTAAA ACCCTGACCT GTAACCTGAA CACTATTATT 1893

CCTTATAGTC AAGTTTTTGT GGTTTCTTGG TAGTCTATAT TTTAAAAATA GTCCTAAAAA 1953

GTGTCTAAGT GCCAGTTTAT TCTATCTAGG CTGTTGTAGT ATAATATTCT TCAAAATATG 2013

TAAGCTGTTG TCAATTATCT AAAGCATGTT AGTTTGGTGC TACACAGTGT TGATTTTTGT 2073

GATGTCCTTT GGTCATGTTT CTGTTAGACT GTAGCTGTGA AACTGTCAGA ATTGTTAACT 2133

GAAACAAATA TTTGCTTGAA AAAAAAAGTT CATGAAGTAC CAATGCAAGT GTTTTATTTT 2193

TTTTCTTTTT TCCAGCCCAT AAGACTAAGG GTTTAAATCT GCTTGCACTA GCTGTGCCTT 2253

CATTAGTTTG CTATAGAAAT CCAGTACTTA TAGTAAATAA AACAGTGTAT TTTGAAGTTT 2313

GACTGCTTGA AAAAGATTAG CATACATCTA ATGTGAAAAG ACCACATTTG ATTCAACTGA 2373

GACCTTGTGT ATGTGACATA TAGTGGCCTA TAAATTTAAT CATAATGATG TTATTGTTTA 2433

CCACTGAGGT GTTAATATAA CATAGTATTT TTGAAAAAGT TTCTTCATCT TATATTGTGT 2493

AATTGTAAAC TAAAGATACC GTGTTTTCTT TGTATTGTGT TCTACCTTCC CTTTCACTGA 2553

-continued

```
AAATGATCAC TTCATTTGAT ACTGTTTTTC ATGTTCTTGT ATTGCAACCT AAAATAAATA     2613

AATATTAAAG TGTGTTATAC TAT                                            2636
```

( 2 ) INFORMATION FOR SEQ ID NO:22:

( i ) SEQUENCE CHARACTERISTICS:
( A ) LENGTH: 170 amino acids
( B ) TYPE: amino acid
( D ) TOPOLOGY: linear ( i i ) MOLECULE TYPE: protein ( x i ) SEQUENCE DESCRIPTION: SEQ ID NO:22:

```
Met Thr Glu Leu Gln Ser Ala Leu Leu Leu Arg Arg Gln Leu Ala Glu
 1               5                  10                  15

Leu Asn Lys Asn Pro Val Glu Gly Phe Ser Ala Gly Leu Ile Asp Asp
            20                  25                  30

Asn Asp Leu Tyr Arg Trp Glu Val Leu Ile Ile Gly Pro Pro Asp Thr
        35                  40                  45

Leu Tyr Glu Gly Gly Val Phe Lys Ala His Leu Thr Phe Pro Lys Asp
    50                  55                  60

Tyr Pro Leu Arg Pro Pro Lys Met Lys Phe Ile Thr Glu Ile Trp His
65                  70                  75                  80

Pro Asn Val Asp Lys Asn Gly Asp Val Cys Ile Ser Ile Leu His Glu
                85                  90                  95

Pro Gly Glu Asp Lys Tyr Gly Tyr Glu Lys Pro Glu Glu Arg Trp Leu
            100                 105                 110

Pro Ile His Thr Val Glu Thr Ile Met Ile Ser Val Ile Ser Met Leu
        115                 120                 125

Ala Asp Pro Asn Gly Asp Ser Pro Ala Asn Val Asp Ala Ala Lys Glu
    130                 135                 140

Trp Arg Glu Asp Arg Asn Gly Glu Phe Lys Arg Lys Val Ala Arg Cys
145                 150                 155                 160

Val Arg Lys Ser Gln Glu Thr Ala Phe Glu
                165                 170
```

( 2 ) INFORMATION FOR SEQ ID NO:23:

( i ) SEQUENCE CHARACTERISTICS:
( A ) LENGTH: 510 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:23:

```
ATGACGGAGC TGCAGTCGGC ACTGCTACTG CGAAGACAGC TGGCAGAACT CAACAAAAAT     60

CCAGTGGAAG GCTTTTCTGC AGGTTTAATA GATGACAATG ATCTCTACCG ATGGGAAGTC    120

CTTATTATTG GCCCTCCAGA TACACTTTAT GAAGGTGGTG TTTTTAAGGC TCATCTTACT    180

TTCCCAAAAG ATTATCCCCT CCGACCTCCT AAAATGAAAT TCATTACAGA AATCTGGCAC    240

CCAAATGTTG ATAAAAATGG TGATGTGTGC ATTTCTATTC TTCATGAGCC TGGGGAAGAT    300

AAGTATGGTT ATGAAAAGCC AGAGGAACGC TGGCTCCCTA TCCACACTGT GGAAACCATC    360

ATGATTAGTG TCATTTCTAT GCTGGCAGAC CCTAATGGAG ACTCACCTGC TAATGTTGAT    420

GCTGCGAAAG AATGGAGGGA AGATAGAAAT GGAGAATTTA AAAGAAAAGT TGCCCGCTGT    480

GTAAGAAAAA GCCAAGAGAC TGCTTTTGAG                                     510
```

-continued ( 2 ) INFORMATION FOR SEQ ID NO:24:

( i ) SEQUENCE CHARACTERISTICS:
( A ) LENGTH: 617 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-423A12

( i x ) FEATURE:
( A ) NAME/KEY: CDS
( B ) LOCATION: 19..528

( x i ) SEQUENCE DESCRIPTION: SEQ ID NO:24:

GGGCCCTCGG CAGGGAGG ATG ACG GAG CTG CAG TCG GCA CTG CTA CTG CGA 51
Met Thr Glu Leu Gln Ser Ala Leu Leu Leu Arg
1 5 10

AGA CAG CTG GCA GAA CTC AAC AAA AAT CCA GTG GAA GGC TTT TCT GCA 99
Arg Gln Leu Ala Glu Leu Asn Lys Asn Pro Val Glu Gly Phe Ser Ala
15 20 25

GGT TTA ATA GAT GAC AAT GAT CTC TAC CGA TGG GAA GTC CTT ATT ATT 147
Gly Leu Ile Asp Asp Asn Asp Leu Tyr Arg Trp Glu Val Leu Ile Ile
30 35 40

GGC CCT CCA GAT ACA CTT TAT GAA GGT GGT GTT TTT AAG GCT CAT CTT 195
Gly Pro Pro Asp Thr Leu Tyr Glu Gly Gly Val Phe Lys Ala His Leu
45 50 55

ACT TTC CCA AAA GAT TAT CCC CTC CGA CCT CCT AAA ATG AAA TTC ATT 243
Thr Phe Pro Lys Asp Tyr Pro Leu Arg Pro Pro Lys Met Lys Phe Ile
60 65 70 75

ACA GAA ATC TGG CAC CCA AAT GTT GAT AAA AAT GGT GAT GTG TGC ATT 291
Thr Glu Ile Trp His Pro Asn Val Asp Lys Asn Gly Asp Val Cys Ile
80 85 90

TCT ATT CTT CAT GAG CCT GGG GAA GAT AAG TAT GGT TAT GAA AAG CCA 339
Ser Ile Leu His Glu Pro Gly Glu Asp Lys Tyr Gly Tyr Glu Lys Pro
95 100 105

GAG GAA CGC TGG CTC CCT ATC CAC ACT GTG GAA ACC ATC ATG ATT AGT 387
Glu Glu Arg Trp Leu Pro Ile His Thr Val Glu Thr Ile Met Ile Ser
110 115 120

GTC ATT TCT ATG CTG GCA GAC CCT AAT GGA GAC TCA CCT GCT AAT GTT 435
Val Ile Ser Met Leu Ala Asp Pro Asn Gly Asp Ser Pro Ala Asn Val
125 130 135

GAT GCT GCG AAA GAA TGG AGG GAA GAT AGA AAT GGA GAA TTT AAA AGA 483
Asp Ala Ala Lys Glu Trp Arg Glu Asp Arg Asn Gly Glu Phe Lys Arg
140 145 150 155

AAA GTT GCC CGC TGT GTA AGA AAA AGC CAA GAG ACT GCT TTT GAG 528
Lys Val Ala Arg Cys Val Arg Lys Ser Gln Glu Thr Ala Phe Glu
160 165 170

TGACATTTAT TTAGCAGCTA GTAACTTCAC TTATTTCAGG GTCTCCAATT GAGAAACATG 588

GCACTGTTTT TCCTGCACTC TACCCACCG 617

( 2 ) INFORMATION FOR SEQ ID NO:25:

( i ) SEQUENCE CHARACTERISTICS:
( A ) LENGTH: 374 amino acids
( B ) TYPE: amino acid
( D ) TOPOLOGY: linear -continued ( i i ) MOLECULE TYPE: protein ( x i ) SEQUENCE DESCRIPTION: SEQ ID NO:25:

Met Val Leu Trp Glu Ser Pro Arg Gln Cys Ser Ser Trp Thr Leu Cys
1 5 10 15

Glu Gly Phe Cys Trp Leu Leu Leu Leu Pro Val Met Leu Leu Ile Val
20 25 30

Ala Arg Pro Val Lys Leu Ala Ala Phe Pro Thr Ser Leu Ser Asp Cys
35 40 45

Gln Thr Pro Thr Gly Trp Asn Cys Ser Gly Tyr Asp Asp Arg Glu Asn
50 55 60

Asp Leu Phe Leu Cys Asp Thr Asn Thr Cys Lys Phe Asp Gly Glu Cys
65 70 75 80

Leu Arg Ile Gly Asp Thr Val Thr Cys Val Cys Gln Phe Lys Cys Asn
85 90 95

Asn Asp Tyr Val Pro Val Cys Gly Ser Asn Gly Glu Ser Tyr Gln Asn
100 105 110

Glu Cys Tyr Leu Arg Gln Ala Ala Cys Lys Gln Gln Ser Glu Ile Leu
115 120 125

Val Val Ser Glu Gly Ser Cys Ala Thr Asp Ala Gly Ser Gly Ser Gly
130 135 140

Asp Gly Val His Glu Gly Ser Gly Glu Thr Ser Gln Lys Glu Thr Ser
145 150 155 160

Thr Cys Asp Ile Cys Gln Phe Gly Ala Glu Cys Asp Glu Asp Ala Glu
165 170 175

Asp Val Trp Cys Val Cys Asn Ile Asp Cys Ser Gln Thr Asn Phe Asn
180 185 190

Pro Leu Cys Ala Ser Asp Gly Lys Ser Tyr Asp Asn Ala Cys Gln Ile
195 200 205

Lys Glu Ala Ser Cys Gln Lys Gln Glu Lys Ile Glu Val Met Ser Leu
210 215 220

Gly Arg Cys Gln Asp Asn Thr Thr Thr Thr Thr Lys Ser Glu Asp Gly
225 230 235 240

His Tyr Ala Arg Thr Asp Tyr Ala Glu Asn Ala Asn Lys Leu Glu Glu
245 250 255

Ser Ala Arg Glu His His Ile Pro Cys Pro Glu His Tyr Asn Gly Phe
260 265 270

Cys Met His Gly Lys Cys Glu His Ser Ile Asn Met Gln Glu Pro Ser
275 280 285

Cys Arg Cys Asp Ala Gly Tyr Thr Gly Gln His Cys Glu Lys Lys Asp
290 295 300

Tyr Ser Val Leu Tyr Val Val Pro Gly Pro Val Arg Phe Gln Tyr Val
305 310 315 320

Leu Ile Ala Ala Val Ile Gly Thr Ile Gln Ile Ala Val Ile Cys Val
325 330 335

Val Val Leu Cys Ile Thr Arg Lys Cys Pro Arg Ser Asn Arg Ile His
340 345 350

Arg Gln Lys Gln Asn Thr Gly His Tyr Ser Ser Asp Asn Thr Thr Arg
355 360 365

Ala Ser Thr Arg Leu Ile
370

( 2 ) INFORMATION FOR SEQ ID NO:26:

( i ) SEQUENCE CHARACTERISTICS:
( A ) LENGTH: 1122 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:26:

```
ATGGTGCTGT GGGAGTCCCC GCGGCAGTGC AGCAGCTGGA CACTTTGCGA GGGCTTTTGC   60
TGGCTGCTGC TGCTGCCCGT CATGCTACTC ATCGTAGCCC GCCCGGTGAA GCTCGCTGCT  120
TTCCCTACCT CCTTAAGTGA CTGCCAAACG CCCACCGGCT GGAATTGCTC TGGTTATGAT  180
GACAGAGAAA ATGATCTCTT CCTCTGTGAC ACCAACACCT GTAAATTTGA TGGGGAATGT  240
TTAAGAATTG GAGACACTGT GACTTGCGTC TGTCAGTTCA AGTGCAACAA TGACTATGTG  300
CCTGTGTGTG GCTCCAATGG GGAGAGCTAC CAGAATGAGT GTTACCTGCG ACAGGCTGCA  360
TGCAAACAGC AGAGTGAGAT ACTTGTGGTG TCAGAAGGAT CATGTGCCAC AGATGCAGGA  420
TCAGGATCTG GAGATGGAGT CCATGAAGGC TCTGGAGAAA CTAGTCAAAA GGAGACATCC  480
ACCTGTGATA TTTGCCAGTT TGGTGCAGAA TGTGACGAAG ATGCCGAGGA TGTCTGGTGT  540
GTGTGTAATA TTGACTGTTC TCAAACCAAC TTCAATCCCC TCTGCGCTTC TGATGGGAAA  600
TCTTATGATA ATGCATGCCA AATCAAAGAA GCATCGTGTC AGAAACAGGA GAAAATTGAA  660
GTCATGTCTT TGGGTCGATG TCAAGATAAC ACAACTACAA CTACTAAGTC TGAAGATGGG  720
CATTATGCAA GAACAGATTA TGCAGAGAAT GCTAACAAAT TAGAAGAAAG TGCCAGAGAA  780
CACCACATAC CTTGTCCGGA ACATTACAAT GGCTTCTGCA TGCATGGGAA GTGTGAGCAT  840
TCTATCAATA TGCAGGAGCC ATCTTGCAGG TGTGATGCTG GTTATACTGG ACAACACTGT  900
GAAAAAAAGG ACTACAGTGT TCTATACGTT GTTCCCGGTC CTGTACGATT TCAGTATGTC  960
TTAATCGCAG CTGTGATTGG AACAATTCAG ATTGCTGTCA TCTGTGTGGT GGTCCTCTGC 1020
ATCACAAGGA AATGCCCCAG AAGCAACAGA ATTCACAGAC AGAAGCAAAA TACAGGGCAC 1080
TACAGTTCAG ACAATACAAC AAGAGCGTCC ACGAGGTTAA TC                    1122
```

( 2 ) INFORMATION FOR SEQ ID NO:27:

( i ) SEQUENCE CHARACTERISTICS:
( A ) LENGTH: 1721 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-092E10

( i x ) FEATURE:
( A ) NAME/KEY: CDS
( B ) LOCATION: 368..1489

( x i ) SEQUENCE DESCRIPTION: SEQ ID NO:27:

```
CTGCGGGGCG CCTTGACTCT CCCTCCACCC TGCCTCCTCG GGCTCCACTC GTCTGCCCCT   60
GGACTCCCGT CTCCTCCTGT CCTCCGGCTT CCCAGAGCTC CCTCCTTATG GCAGCAGCTT  120
CCCGCGTCTC CGGCGCAGCT TCTCAGCGGA CGACCCTCTC GCTCCGGGGC TGAGCCAGTC  180
CCTGGATGTT GCTGAAACTC TCGAGATCAT GCGCGGGTTT GGCTGCTGCT TCCCCGCCGG  240
```

-continued

```
GTGCCACTGC CACCGCCGCC GCCTCTGCTG CCGCCGTCCG CGGGATGCTC AGTAGCCCGC      300

TGCCCGGCCC CCGCGATCCT GTGTTCCTCG GAAGCCGTTT GCTGCTGCAG AGTTGCACGA      360

ACTAGTC   ATG  GTG  CTG  TGG  GAG  TCC  CCG  CGG  CAG  TGC  AGC  AGC  TGG  ACA      409
          Met  Val  Leu  Trp  Glu  Ser  Pro  Arg  Gln  Cys  Ser  Ser  Trp  Thr
          1                   5                        10

CTT  TGC  GAG  GGC  TTT  TGC  TGG  CTG  CTG  CTG  CTG  CCC  GTC  ATG  CTA  CTC      457
Leu  Cys  Glu  Gly  Phe  Cys  Trp  Leu  Leu  Leu  Leu  Pro  Val  Met  Leu  Leu
15                       20                       25                       30

ATC  GTA  GCC  CGC  CCG  GTG  AAG  CTC  GCT  GCT  TTC  CCT  ACC  TCC  TTA  AGT      505
Ile  Val  Ala  Arg  Pro  Val  Lys  Leu  Ala  Ala  Phe  Pro  Thr  Ser  Leu  Ser
                    35                       40                       45

GAC  TGC  CAA  ACG  CCC  ACC  GGC  TGG  AAT  TGC  TCT  GGT  TAT  GAT  GAC  AGA      553
Asp  Cys  Gln  Thr  Pro  Thr  Gly  Trp  Asn  Cys  Ser  Gly  Tyr  Asp  Asp  Arg
               50                       55                       60

GAA  AAT  GAT  CTC  TTC  CTC  TGT  GAC  ACC  AAC  ACC  TGT  AAA  TTT  GAT  GGG      601
Glu  Asn  Asp  Leu  Phe  Leu  Cys  Asp  Thr  Asn  Thr  Cys  Lys  Phe  Asp  Gly
          65                       70                       75

GAA  TGT  TTA  AGA  ATT  GGA  GAC  ACT  GTG  ACT  TGC  GTC  TGT  CAG  TTC  AAG      649
Glu  Cys  Leu  Arg  Ile  Gly  Asp  Thr  Val  Thr  Cys  Val  Cys  Gln  Phe  Lys
     80                       85                       90

TGC  AAC  AAT  GAC  TAT  GTG  CCT  GTG  TGT  GGC  TCC  AAT  GGG  GAG  AGC  TAC      697
Cys  Asn  Asn  Asp  Tyr  Val  Pro  Val  Cys  Gly  Ser  Asn  Gly  Glu  Ser  Tyr
95                       100                      105                      110

CAG  AAT  GAG  TGT  TAC  CTG  CGA  CAG  GCT  GCA  TGC  AAA  CAG  CAG  AGT  GAG      745
Gln  Asn  Glu  Cys  Tyr  Leu  Arg  Gln  Ala  Ala  Cys  Lys  Gln  Gln  Ser  Glu
                    115                      120                      125

ATA  CTT  GTG  GTG  TCA  GAA  GGA  TCA  TGT  GCC  ACA  GAT  GCA  GGA  TCA  GGA      793
Ile  Leu  Val  Val  Ser  Glu  Gly  Ser  Cys  Ala  Thr  Asp  Ala  Gly  Ser  Gly
               130                      135                      140

TCT  GGA  GAT  GGA  GTC  CAT  GAA  GGC  TCT  GGA  GAA  ACT  AGT  CAA  AAG  GAG      841
Ser  Gly  Asp  Gly  Val  His  Glu  Gly  Ser  Gly  Glu  Thr  Ser  Gln  Lys  Glu
          145                      150                      155

ACA  TCC  ACC  TGT  GAT  ATT  TGC  CAG  TTT  GGT  GCA  GAA  TGT  GAC  GAA  GAT      889
Thr  Ser  Thr  Cys  Asp  Ile  Cys  Gln  Phe  Gly  Ala  Glu  Cys  Asp  Glu  Asp
     160                      165                      170

GCC  GAG  GAT  GTC  TGG  TGT  GTG  TGT  AAT  ATT  GAC  TGT  TCT  CAA  ACC  AAC      937
Ala  Glu  Asp  Val  Trp  Cys  Val  Cys  Asn  Ile  Asp  Cys  Ser  Gln  Thr  Asn
175                      180                      185                      190

TTC  AAT  CCC  CTC  TGC  GCT  TCT  GAT  GGG  AAA  TCT  TAT  GAT  AAT  GCA  TGC      985
Phe  Asn  Pro  Leu  Cys  Ala  Ser  Asp  Gly  Lys  Ser  Tyr  Asp  Asn  Ala  Cys
                    195                      200                      205

CAA  ATC  AAA  GAA  GCA  TCG  TGT  CAG  AAA  CAG  GAG  AAA  ATT  GAA  GTC  ATG     1033
Gln  Ile  Lys  Glu  Ala  Ser  Cys  Gln  Lys  Gln  Glu  Lys  Ile  Glu  Val  Met
               210                      215                      220

TCT  TTG  GGT  CGA  TGT  CAA  GAT  AAC  ACA  ACT  ACA  ACT  ACT  AAG  TCT  GAA     1081
Ser  Leu  Gly  Arg  Cys  Gln  Asp  Asn  Thr  Thr  Thr  Thr  Thr  Lys  Ser  Glu
          225                      230                      235

GAT  GGG  CAT  TAT  GCA  AGA  ACA  GAT  TAT  GCA  GAG  AAT  GCT  AAC  AAA  TTA     1129
Asp  Gly  His  Tyr  Ala  Arg  Thr  Asp  Tyr  Ala  Glu  Asn  Ala  Asn  Lys  Leu
     240                      245                      250

GAA  GAA  AGT  GCC  AGA  GAA  CAC  CAC  ATA  CCT  TGT  CCG  GAA  CAT  TAC  AAT     1177
Glu  Glu  Ser  Ala  Arg  Glu  His  His  Ile  Pro  Cys  Pro  Glu  His  Tyr  Asn
255                      260                      265                      270

GGC  TTC  TGC  ATG  CAT  GGG  AAG  TGT  GAG  CAT  TCT  ATC  AAT  ATG  CAG  GAG     1225
Gly  Phe  Cys  Met  His  Gly  Lys  Cys  Glu  His  Ser  Ile  Asn  Met  Gln  Glu
                    275                      280                      285

CCA  TCT  TGC  AGG  TGT  GAT  GCT  GGT  TAT  ACT  GGA  CAA  CAC  TGT  GAA  AAA     1273
Pro  Ser  Cys  Arg  Cys  Asp  Ala  Gly  Tyr  Thr  Gly  Gln  His  Cys  Glu  Lys
               290                      295                      300
```

-continued

```
AAG GAC TAC AGT GTT CTA TAC GTT GTT CCC GGT CCT GTA CGA TTT CAG      1321
Lys Asp Tyr Ser Val Leu Tyr Val Val Pro Gly Pro Val Arg Phe Gln
        305                 310                 315

TAT GTC TTA ATC GCA GCT GTG ATT GGA ACA ATT CAG ATT GCT GTC ATC      1369
Tyr Val Leu Ile Ala Ala Val Ile Gly Thr Ile Gln Ile Ala Val Ile
    320                 325                 330

TGT GTG GTG GTC CTC TGC ATC ACA AGG AAA TGC CCC AGA AGC AAC AGA      1417
Cys Val Val Val Leu Cys Ile Thr Arg Lys Cys Pro Arg Ser Asn Arg
335                 340                 345                 350

ATT CAC AGA CAG AAG CAA AAT ACA GGG CAC TAC AGT TCA GAC AAT ACA      1465
Ile His Arg Gln Lys Gln Asn Thr Gly His Tyr Ser Ser Asp Asn Thr
                355                 360                 365

ACA AGA GCG TCC ACG AGG TTA ATC TAA AGGGAGCATG TTTCACAGTG            1512
Thr Arg Ala Ser Thr Arg Leu Ile
            370

GCTGGACTAC CGAGAGCTTG GACTACACAA TACAGTATTA TAGACAAAAG AATAAGACAA    1572

GAGATCTACA CATGTTGCCT TGCATTTGTG GTAATCTACA CCAATGAAAA CATGTACTAC    1632

AGCTATATTT GATTATGTAT GGATATATTT GAAATAGTAT ACATTGTCTT GATGTTTTTT    1692

CTGTAATGTA AATAAACTAT TTATATCAC                                      1721
```

( 2 ) INFORMATION FOR SEQ ID NO:28:

( i ) SEQUENCE CHARACTERISTICS:
( A ) LENGTH: 817 amino acids
( B ) TYPE: amino acid
( D ) TOPOLOGY: linear ( i i ) MOLECULE TYPE: protein ( x i ) SEQUENCE DESCRIPTION: SEQ ID NO:28:

```
Met Gly Asp Thr Val Val Glu Pro Ala Pro Leu Lys Pro Thr Ser Glu
 1               5                  10                  15

Pro Thr Ser Gly Pro Pro Gly Asn Asn Gly Gly Ser Leu Leu Ser Val
            20                  25                  30

Ile Thr Glu Gly Val Gly Glu Leu Ser Val Ile Asp Pro Glu Val Ala
        35                  40                  45

Gln Lys Ala Cys Gln Glu Val Leu Glu Lys Val Lys Leu Leu His Gly
    50                  55                  60

Gly Val Ala Val Ser Ser Arg Gly Thr Pro Leu Glu Leu Val Asn Gly
65                  70                  75                  80

Asp Gly Val Asp Ser Glu Ile Arg Cys Leu Asp Asp Pro Pro Ala Gln
                85                  90                  95

Ile Arg Glu Glu Glu Asp Glu Met Gly Ala Ala Val Ala Ser Gly Thr
            100                 105                 110

Ala Lys Gly Ala Arg Arg Arg Arg Gln Asn Asn Ser Ala Lys Gln Ser
        115                 120                 125

Trp Leu Leu Arg Leu Phe Glu Ser Lys Leu Phe Asp Ile Ser Met Ala
    130                 135                 140

Ile Ser Tyr Leu Tyr Asn Ser Lys Glu Pro Gly Val Gln Ala Tyr Ile
145                 150                 155                 160

Gly Asn Arg Leu Phe Cys Phe Arg Asn Glu Asp Val Asp Phe Tyr Leu
                165                 170                 175

Pro Gln Leu Leu Asn Met Tyr Ile His Met Asp Glu Asp Val Gly Asp
            180                 185                 190

Ala Ile Lys Pro Tyr Ile Val His Arg Cys Arg Gln Ser Ile Asn Phe
        195                 200                 205
```

-continued

```
Ser Leu Gln Cys Ala Leu Leu Leu Gly Ala Tyr Ser Ser Asp Met His
    210                 215                 220

Ile Ser Thr Gln Arg His Ser Arg Gly Thr Lys Leu Arg Lys Leu Ile
225                 230                 235                 240

Leu Ser Asp Glu Leu Lys Pro Ala His Arg Lys Arg Glu Leu Pro Ser
                245                 250                 255

Leu Ser Pro Ala Pro Asp Thr Gly Leu Ser Pro Ser Lys Arg Thr His
            260                 265                 270

Gln Arg Ser Lys Ser Asp Ala Thr Ala Ser Ile Ser Leu Ser Ser Asn
        275                 280                 285

Leu Lys Arg Thr Ala Ser Asn Pro Lys Val Glu Asn Glu Asp Glu Glu
    290                 295                 300

Leu Ser Ser Ser Thr Glu Ser Ile Asp Asn Ser Phe Ser Ser Pro Val
305                 310                 315                 320

Arg Leu Ala Pro Glu Arg Glu Phe Ile Lys Ser Leu Met Ala Ile Gly
                325                 330                 335

Lys Arg Leu Ala Thr Leu Pro Thr Lys Glu Gln Lys Thr Gln Arg Leu
            340                 345                 350

Ile Ser Glu Leu Ser Leu Leu Asn His Lys Leu Pro Ala Arg Val Trp
        355                 360                 365

Leu Pro Thr Ala Gly Phe Asp His His Val Val Arg Val Pro His Thr
    370                 375                 380

Gln Ala Val Val Leu Asn Ser Lys Asp Lys Ala Pro Tyr Leu Ile Tyr
385                 390                 395                 400

Val Glu Val Leu Glu Cys Glu Asn Phe Asp Thr Thr Ser Val Pro Ala
                405                 410                 415

Arg Ile Pro Glu Asn Arg Ile Arg Ser Thr Arg Ser Val Glu Asn Leu
            420                 425                 430

Pro Glu Cys Gly Ile Thr His Glu Gln Arg Ala Gly Ser Phe Ser Thr
        435                 440                 445

Val Pro Asn Tyr Asp Asn Asp Asp Glu Ala Trp Ser Val Asp Asp Ile
    450                 455                 460

Gly Glu Leu Gln Val Glu Leu Pro Glu Val His Thr Asn Ser Cys Asp
465                 470                 475                 480

Asn Ile Ser Gln Phe Ser Val Asp Ser Ile Thr Ser Gln Glu Ser Lys
                485                 490                 495

Glu Pro Val Phe Ile Ala Ala Gly Asp Ile Arg Arg Arg Leu Ser Glu
            500                 505                 510

Gln Leu Ala His Thr Pro Thr Ala Phe Lys Arg Asp Pro Glu Asp Pro
        515                 520                 525

Ser Ala Val Ala Leu Lys Glu Pro Trp Gln Glu Lys Val Arg Arg Ile
    530                 535                 540

Arg Glu Gly Ser Pro Tyr Gly His Leu Pro Asn Trp Arg Leu Leu Ser
545                 550                 555                 560

Val Ile Val Lys Cys Gly Asp Asp Leu Arg Gln Glu Leu Leu Ala Phe
                565                 570                 575

Gln Val Leu Lys Gln Leu Gln Ser Ile Trp Glu Gln Glu Arg Val Pro
            580                 585                 590

Leu Trp Ile Lys Pro Ile Gln Asp Ser Cys Glu Ile Thr Thr Asp Ser
        595                 600                 605

Gly Met Ile Glu Pro Val Val Asn Ala Val Ser Ile His Gln Val Lys
    610                 615                 620

Lys Gln Ser Gln Leu Ser Leu Leu Asp Tyr Phe Leu Gln Glu His Gly
625                 630                 635                 640
```

-continued

```
Ser Tyr Thr Thr Glu Ala Phe Leu Ser Ala Gln Arg Asn Phe Val Gln
                645                 650                 655

Ser Cys Ala Gly Tyr Cys Leu Val Cys Tyr Leu Leu Gln Val Lys Asp
            660                 665                 670

Arg His Asn Gly Asn Ile Leu Leu Asp Ala Glu Gly His Ile Ile His
        675                 680                 685

Ile Asp Phe Gly Phe Ile Leu Ser Ser Ser Pro Arg Asn Leu Gly Phe
    690                 695                 700

Glu Thr Ser Ala Phe Lys Leu Thr Thr Glu Phe Val Asp Val Met Gly
705                 710                 715                 720

Gly Leu Asp Gly Asp Met Phe Asn Tyr Tyr Lys Met Leu Met Leu Gln
                725                 730                 735

Gly Leu Ile Ala Ala Arg Lys His Met Asp Lys Val Val Gln Ile Val
            740                 745                 750

Glu Ile Met Gln Gln Gly Ser Gln Leu Pro Cys Phe His Gly Ser Ser
        755                 760                 765

Thr Ile Arg Asn Leu Lys Glu Arg Phe His Met Ser Met Thr Glu Glu
    770                 775                 780

Gln Leu Gln Leu Leu Val Glu Gln Met Val Asp Gly Ser Met Arg Ser
785                 790                 795                 800

Ile Thr Thr Lys Leu Tyr Asp Gly Phe Gln Tyr Leu Thr Asn Gly Ile
                805                 810                 815

Met
```

( 2 ) INFORMATION FOR SEQ ID NO:29:

( i ) SEQUENCE CHARACTERISTICS:
( A ) LENGTH: 2451 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:29:

```
ATGGGAGATA CAGTAGTGGA GCCTGCCCCC TTGAAGCCAA CTTCTGAGCC CACTTCTGGC    60
CCACCAGGGA ATAATGGGGG GTCCCTGCTA AGTGTCATCA CGGAGGGGGT CGGGGAACTA   120
TCAGTGATTG ACCCTGAGGT GGCCCAGAAG GCCTGCCAGG AGGTGTTGGA GAAAGTCAAG   180
CTTTTGCATG GAGGCGTGGC AGTCTCTAGC AGAGGCACCC CACTGGAGTT GGTCAATGGG   240
GATGGTGTGG ACAGTGAGAT CCGTTGCCTA GATGATCCAC CTGCCCAGAT CAGGGAGGAG   300
GAAGATGAGA TGGGGGCCGC TGTGGCCTCA GGCACAGCCA AAGGAGCAAG AAGACGGCGG   360
CAGAACAACT CAGCTAAACA GTCTTGGCTG CTGAGGCTGT TTGAGTCAAA ACTGTTTGAC   420
ATCTCCATGG CCATTTCATA CCTGTATAAC TCCAAGGAGC CTGGAGTACA AGCCTACATT   480
GGCAACCGGC TCTTCTGCTT TCGCAACGAG GACGTGGACT TCTATCTGCC CCAGTTGCTT   540
AACATGTACA TCCACATGGA TGAGGACGTG GGTGATGCCA TTAAGCCCTA CATAGTCCAC   600
CGTTGCCGCC AGAGCATTAA CTTTTCCCTC CAGTGTGCCC TGTTGCTTGG GGCCTATTCT   660
TCAGACATGC ACATTTCCAC TCAACGACAC TCCCGTGGGA CCAAGCTACG GAAGCTGATC   720
CTCTCAGATG AGCTAAAGCC AGCTCACAGG AAGAGGGAGC TGCCCTCCTT GAGCCCGGCC   780
CCTGATACAG GGCTGTCTCC CTCCAAAAGG ACTCACCAGC GCTCTAAGTC AGATGCCACT   840
GCCAGCATAA GTCTCAGCAG CAACCTGAAA CGAACAGCCA GCAACCCTAA AGTGGAGAAT   900
GAGGATGAGG AGCTCTCCTC CAGCACCGAG AGTATTGATA ATTCATTCAG TTCCCCTGTT   960
```

-continued

CGACTGGCTC CTGAGAGAGA ATTCATCAAG TCCCTGATGG CGATCGGCAA GCGGCTGGCC 1020

ACGCTCCCCA CCAAAGAGCA GAAAACACAG AGGCTGATCT CAGAGCTCTC CCTGCTCAAC 1080

CATAAGCTCC CTGCCCGAGT CTGGCTGCCC ACTGCTGGCT TTGACCACCA CGTGGTCCGT 1140

GTACCCCACA CACAGGCTGT TGTCCTCAAC TCCAAGGACA AGGCTCCCTA CCTGATTTAT 1200

GTGGAAGTCC TTGAATGTGA AAACTTTGAC ACCACCAGTG TCCCTGCCCG GATCCCCGAG 1260

AACCGAATTC GGAGTACGAG GTCCGTAGAA AACTTGCCCG AATGTGGTAT TACCCATGAG 1320

CAGCGAGCTG GCAGCTTCAG CACTGTGCCC AACTATGACA ACGATGATGA GGCCTGGTCG 1380

GTGGATGACA TAGGCGAGCT GCAAGTGGAG CTCCCCGAAG TGCATACCAA CAGCTGTGAC 1440

AACATCTCCC AGTTCTCTGT GGACAGCATC ACCAGCCAGG AGAGCAAGGA GCCTGTGTTC 1500

ATTGCAGCAG GGGACATCCG CCGGCGCCTT TCGGAACAGC TGGCTCATAC CCCGACAGCC 1560

TTCAAACGAG ACCCAGAAGA TCCTTCTGCA GTTGCTCTCA AAGAGCCCTG GCAGGAGAAA 1620

GTACGGCGGA TCAGAGAGGG CTCCCCCTAC GGCCATCTCC CCAATTGGCG GCTCCTGTCA 1680

GTCATTGTCA AGTGTGGGGA TGACCTTCGG CAAGAGCTTC TGGCCTTTCA GGTGTTGAAG 1740

CAACTGCAGT CCATTTGGGA ACAGGAGCGA GTGCCCCTTT GGATCAAGCC AATACAAGAT 1800

TCTTGTGAAA TTACGACTGA TAGTGGCATG ATTGAACCAG TGGTCAATGC TGTGTCCATC 1860

CATCAGGTGA AGAAACAGTC ACAGCTCTCC TTGCTCGATT ACTTCCTACA GGAGCACGGC 1920

AGTTACACCA CTGAGGCATT CCTCAGTGCA CAGCGCAATT TTGTGCAAAG TTGTGCTGGG 1980

TACTGCTTGG TCTGCTACCT GCTGCAAGTC AAGGACAGAC ACAATGGGAA TATCCTTTTG 2040

GACGCAGAAG GCCACATCAT CCACATCGAC TTTGGCTTCA TCCTCTCCAG CTCACCCCGA 2100

AATCTGGGCT TTGAGACGTC AGCCTTTAAG CTGACCACAG AGTTTGTGGA TGTGATGGGC 2160

GGCCTGGATG GCGACATGTT CAACTACTAT AAGATGCTGA TGCTGCAAGG GCTGATTGCC 2220

GCTCGGAAAC ACATGGACAA GGTGGTGCAG ATCGTGGAGA TCATGCAGCA AGGTTCTCAG 2280

CTTCCTTGCT TCCATGGCTC CAGCACCATT CGAAACCTCA AAGAGAGGTT CCACATGAGC 2340

ATGACTGAGG AGCAGCTGCA GCTGCTGGTG GAGCAGATGG TGGATGGCAG TATGCGGTCT 2400

ATCACCACCA AACTCTATGA CGGCTTCCAG TACCTCACCA ACGGCATCAT G 2451

( 2 ) INFORMATION FOR SEQ ID NO:30:

( i ) SEQUENCE CHARACTERISTICS:
( A ) LENGTH: 3602 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-428B12c2

( i x ) FEATURE:
( A ) NAME/KEY: CDS
( B ) LOCATION: 429..2879

( x i ) SEQUENCE DESCRIPTION: SEQ ID NO:30:

GGTGGCTCAC GCCTGTAATC CCAGCACTTT GGGAGGACAA GGCAGATCCC TTGAGCCCAG 60

GAGGTAGAGG CTGCAGTGAG CTGTGATGGT GCCACTGCAC TCCAGCCTGG GCAATGAAGC 120

-continued

AAGACCCTAT CTGAAAAAAA AAATTTTTAA AAAAGGCAAA GATGGGCCTG GGGCACCAAA 180

TATTCCAGAG GAAAGGGAAC GTGTGTACTC CTTGAGGTGG GGAACATGAC CCACTTGAGG 240

TGCAGAAAGA AGACTTGTAT GGGGCTGGTG CAGCCTCCGC GGCCGCTGTC AGGGAAGCGC 300

AGGCGGCCAA TGGAACCCGG GAGCGGTCGC TGCTGCTGAG GCGGCAGTGT CGGCAGTCCA 360

ACCGCGACTG CCCGCACCCC CTCCGCGGGG TCCCCCAGAG CTTGGAAGCT CGAAGTCTGG 420

CTGTGGCC ATG GGA GAT ACA GTA GTG GAG CCT GCC CCC TTG AAG CCA ACT 470
Met Gly Asp Thr Val Val Glu Pro Ala Pro Leu Lys Pro Thr
1 5 10

TCT GAG CCC ACT TCT GGC CCA CCA GGG AAT AAT GGG GGG TCC CTG CTA 518
Ser Glu Pro Thr Ser Gly Pro Pro Gly Asn Asn Gly Gly Ser Leu Leu
15 20 25 30

AGT GTC ATC ACG GAG GGG GTC GGG GAA CTA TCA GTG ATT GAC CCT GAG 566
Ser Val Ile Thr Glu Gly Val Gly Glu Leu Ser Val Ile Asp Pro Glu
35 40 45

GTG GCC CAG AAG GCC TGC CAG GAG GTG TTG GAG AAA GTC AAG CTT TTG 614
Val Ala Gln Lys Ala Cys Gln Glu Val Leu Glu Lys Val Lys Leu Leu
50 55 60

CAT GGA GGC GTG GCA GTC TCT AGC AGA GGC ACC CCA CTG GAG TTG GTC 662
His Gly Gly Val Ala Val Ser Ser Arg Gly Thr Pro Leu Glu Leu Val
65 70 75

AAT GGG GAT GGT GTG GAC AGT GAG ATC CGT TGC CTA GAT GAT CCA CCT 710
Asn Gly Asp Gly Val Asp Ser Glu Ile Arg Cys Leu Asp Asp Pro Pro
80 85 90

GCC CAG ATC AGG GAG GAG GAA GAT GAG ATG GGG GCC GCT GTG GCC TCA 758
Ala Gln Ile Arg Glu Glu Glu Asp Glu Met Gly Ala Ala Val Ala Ser
95 100 105 110

GGC ACA GCC AAA GGA GCA AGA AGA CGG CGG CAG AAC AAC TCA GCT AAA 806
Gly Thr Ala Lys Gly Ala Arg Arg Arg Arg Gln Asn Asn Ser Ala Lys
115 120 125

CAG TCT TGG CTG CTG AGG CTG TTT GAG TCA AAA CTG TTT GAC ATC TCC 854
Gln Ser Trp Leu Leu Arg Leu Phe Glu Ser Lys Leu Phe Asp Ile Ser
130 135 140

ATG GCC ATT TCA TAC CTG TAT AAC TCC AAG GAG CCT GGA GTA CAA GCC 902
Met Ala Ile Ser Tyr Leu Tyr Asn Ser Lys Glu Pro Gly Val Gln Ala
145 150 155

TAC ATT GGC AAC CGG CTC TTC TGC TTT CGC AAC GAG GAC GTG GAC TTC 950
Tyr Ile Gly Asn Arg Leu Phe Cys Phe Arg Asn Glu Asp Val Asp Phe
160 165 170

TAT CTG CCC CAG TTG CTT AAC ATG TAC ATC CAC ATG GAT GAG GAC GTG 998
Tyr Leu Pro Gln Leu Leu Asn Met Tyr Ile His Met Asp Glu Asp Val
175 180 185 190

GGT GAT GCC ATT AAG CCC TAC ATA GTC CAC CGT TGC CGC CAG AGC ATT 1046
Gly Asp Ala Ile Lys Pro Tyr Ile Val His Arg Cys Arg Gln Ser Ile
195 200 205

AAC TTT TCC CTC CAG TGT GCC CTG TTG CTT GGG GCC TAT TCT TCA GAC 1094
Asn Phe Ser Leu Gln Cys Ala Leu Leu Leu Gly Ala Tyr Ser Ser Asp
210 215 220

ATG CAC ATT TCC ACT CAA CGA CAC TCC CGT GGG ACC AAG CTA CGG AAG 1142
Met His Ile Ser Thr Gln Arg His Ser Arg Gly Thr Lys Leu Arg Lys
225 230 235

CTG ATC CTC TCA GAT GAG CTA AAG CCA GCT CAC AGG AAG AGG GAG CTG 1190
Leu Ile Leu Ser Asp Glu Leu Lys Pro Ala His Arg Lys Arg Glu Leu
240 245 250

CCC TCC TTG AGC CCG GCC CCT GAT ACA GGG CTG TCT CCC TCC AAA AGG 1238
Pro Ser Leu Ser Pro Ala Pro Asp Thr Gly Leu Ser Pro Ser Lys Arg
255 260 265 270

ACT CAC CAG CGC TCT AAG TCA GAT GCC ACT GCC AGC ATA AGT CTC AGC 1286
Thr His Gln Arg Ser Lys Ser Asp Ala Thr Ala Ser Ile Ser Leu Ser

-continued

```
                    275                        280                        285

AGC AAC CTG AAA CGA ACA GCC AGC AAC CCT AAA GTG GAG AAT GAG GAT      1334
Ser Asn Leu Lys Arg Thr Ala Ser Asn Pro Lys Val Glu Asn Glu Asp
            290                 295                 300

GAG GAG CTC TCC TCC AGC ACC GAG AGT ATT GAT AAT TCA TTC AGT TCC      1382
Glu Glu Leu Ser Ser Ser Thr Glu Ser Ile Asp Asn Ser Phe Ser Ser
        305                 310                 315

CCT GTT CGA CTG GCT CCT GAG AGA GAA TTC ATC AAG TCC CTG ATG GCG      1430
Pro Val Arg Leu Ala Pro Glu Arg Glu Phe Ile Lys Ser Leu Met Ala
    320                 325                 330

ATC GGC AAG CGG CTG GCC ACG CTC CCC ACC AAA GAG CAG AAA ACA CAG      1478
Ile Gly Lys Arg Leu Ala Thr Leu Pro Thr Lys Glu Gln Lys Thr Gln
335                 340                 345                 350

AGG CTG ATC TCA GAG CTC TCC CTG CTC AAC CAT AAG CTC CCT GCC CGA      1526
Arg Leu Ile Ser Glu Leu Ser Leu Leu Asn His Lys Leu Pro Ala Arg
                355                 360                 365

GTC TGG CTG CCC ACT GCT GGC TTT GAC CAC CAC GTG GTC CGT GTA CCC      1574
Val Trp Leu Pro Thr Ala Gly Phe Asp His His Val Val Arg Val Pro
            370                 375                 380

CAC ACA CAG GCT GTT GTC CTC AAC TCC AAG GAC AAG GCT CCC TAC CTG      1622
His Thr Gln Ala Val Val Leu Asn Ser Lys Asp Lys Ala Pro Tyr Leu
        385                 390                 395

ATT TAT GTG GAA GTC CTT GAA TGT GAA AAC TTT GAC ACC ACC AGT GTC      1670
Ile Tyr Val Glu Val Leu Glu Cys Glu Asn Phe Asp Thr Thr Ser Val
    400                 405                 410

CCT GCC CGG ATC CCC GAG AAC CGA ATT CGG AGT ACG AGG TCC GTA GAA      1718
Pro Ala Arg Ile Pro Glu Asn Arg Ile Arg Ser Thr Arg Ser Val Glu
415                 420                 425                 430

AAC TTG CCC GAA TGT GGT ATT ACC CAT GAG CAG CGA GCT GGC AGC TTC      1766
Asn Leu Pro Glu Cys Gly Ile Thr His Glu Gln Arg Ala Gly Ser Phe
                435                 440                 445

AGC ACT GTG CCC AAC TAT GAC AAC GAT GAT GAG GCC TGG TCG GTG GAT      1814
Ser Thr Val Pro Asn Tyr Asp Asn Asp Asp Glu Ala Trp Ser Val Asp
            450                 455                 460

GAC ATA GGC GAG CTG CAA GTG GAG CTC CCC GAA GTG CAT ACC AAC AGC      1862
Asp Ile Gly Glu Leu Gln Val Glu Leu Pro Glu Val His Thr Asn Ser
        465                 470                 475

TGT GAC AAC ATC TCC CAG TTC TCT GTG GAC AGC ATC ACC AGC CAG GAG      1910
Cys Asp Asn Ile Ser Gln Phe Ser Val Asp Ser Ile Thr Ser Gln Glu
    480                 485                 490

AGC AAG GAG CCT GTG TTC ATT GCA GCA GGG GAC ATC CGC CGG CGC CTT      1958
Ser Lys Glu Pro Val Phe Ile Ala Ala Gly Asp Ile Arg Arg Arg Leu
495                 500                 505                 510

TCG GAA CAG CTG GCT CAT ACC CCG ACA GCC TTC AAA CGA GAC CCA GAA      2006
Ser Glu Gln Leu Ala His Thr Pro Thr Ala Phe Lys Arg Asp Pro Glu
                515                 520                 525

GAT CCT TCT GCA GTT GCT CTC AAA GAG CCC TGG CAG GAG AAA GTA CGG      2054
Asp Pro Ser Ala Val Ala Leu Lys Glu Pro Trp Gln Glu Lys Val Arg
            530                 535                 540

CGG ATC AGA GAG GGC TCC CCC TAC GGC CAT CTC CCC AAT TGG CGG CTC      2102
Arg Ile Arg Glu Gly Ser Pro Tyr Gly His Leu Pro Asn Trp Arg Leu
        545                 550                 555

CTG TCA GTC ATT GTC AAG TGT GGG GAT GAC CTT CGG CAA GAG CTT CTG      2150
Leu Ser Val Ile Val Lys Cys Gly Asp Asp Leu Arg Gln Glu Leu Leu
    560                 565                 570

GCC TTT CAG GTG TTG AAG CAA CTG CAG TCC ATT TGG GAA CAG GAG CGA      2198
Ala Phe Gln Val Leu Lys Gln Leu Gln Ser Ile Trp Glu Gln Glu Arg
575                 580                 585                 590

GTG CCC CTT TGG ATC AAG CCA ATA CAA GAT TCT TGT GAA ATT ACG ACT      2246
Val Pro Leu Trp Ile Lys Pro Ile Gln Asp Ser Cys Glu Ile Thr Thr
```

-continued

```
                595                     600                     605

GAT AGT GGC ATG ATT GAA CCA GTG GTC AAT GCT GTG TCC ATC CAT CAG      2294
Asp Ser Gly Met Ile Glu Pro Val Val Asn Ala Val Ser Ile His Gln
            610                 615                 620

GTG AAG AAA CAG TCA CAG CTC TCC TTG CTC GAT TAC TTC CTA CAG GAG      2342
Val Lys Lys Gln Ser Gln Leu Ser Leu Leu Asp Tyr Phe Leu Gln Glu
        625                 630                 635

CAC GGC AGT TAC ACC ACT GAG GCA TTC CTC AGT GCA CAG CGC AAT TTT      2390
His Gly Ser Tyr Thr Thr Glu Ala Phe Leu Ser Ala Gln Arg Asn Phe
    640                 645                 650

GTG CAA AGT TGT GCT GGG TAC TGC TTG GTC TGC TAC CTG CTG CAA GTC      2438
Val Gln Ser Cys Ala Gly Tyr Cys Leu Val Cys Tyr Leu Leu Gln Val
655                 660                 665                 670

AAG GAC AGA CAC AAT GGG AAT ATC CTT TTG GAC GCA GAA GGC CAC ATC      2486
Lys Asp Arg His Asn Gly Asn Ile Leu Leu Asp Ala Glu Gly His Ile
                675                 680                 685

ATC CAC ATC GAC TTT GGC TTC ATC CTC TCC AGC TCA CCC CGA AAT CTG      2534
Ile His Ile Asp Phe Gly Phe Ile Leu Ser Ser Ser Pro Arg Asn Leu
            690                 695                 700

GGC TTT GAG ACG TCA GCC TTT AAG CTG ACC ACA GAG TTT GTG GAT GTG      2582
Gly Phe Glu Thr Ser Ala Phe Lys Leu Thr Thr Glu Phe Val Asp Val
        705                 710                 715

ATG GGC GGC CTG GAT GGC GAC ATG TTC AAC TAC TAT AAG ATG CTG ATG      2630
Met Gly Gly Leu Asp Gly Asp Met Phe Asn Tyr Tyr Lys Met Leu Met
    720                 725                 730

CTG CAA GGG CTG ATT GCC GCT CGG AAA CAC ATG GAC AAG GTG GTG CAG      2678
Leu Gln Gly Leu Ile Ala Ala Arg Lys His Met Asp Lys Val Val Gln
735                 740                 745                 750

ATC GTG GAG ATC ATG CAG CAA GGT TCT CAG CTT CCT TGC TTC CAT GGC      2726
Ile Val Glu Ile Met Gln Gln Gly Ser Gln Leu Pro Cys Phe His Gly
                755                 760                 765

TCC AGC ACC ATT CGA AAC CTC AAA GAG AGG TTC CAC ATG AGC ATG ACT      2774
Ser Ser Thr Ile Arg Asn Leu Lys Glu Arg Phe His Met Ser Met Thr
            770                 775                 780

GAG GAG CAG CTG CAG CTG CTG GTG GAG CAG ATG GTG GAT GGC AGT ATG      2822
Glu Glu Gln Leu Gln Leu Leu Val Glu Gln Met Val Asp Gly Ser Met
        785                 790                 795

CGG TCT ATC ACC ACC AAA CTC TAT GAC GGC TTC CAG TAC CTC ACC AAC      2870
Arg Ser Ile Thr Thr Lys Leu Tyr Asp Gly Phe Gln Tyr Leu Thr Asn
    800                 805                 810

GGC ATC ATG TGA CACGCTCCTC AGCCCAGGAG TGGTGGGGGG TCCAGGGCAC          2922
Gly Ile Met  *
815

CCTCCCTAGA GGGCCCTTGT CTGAGAAACC CCAAACCAGG AAACCCCACC TACCCAACCA    2982

TCCACCCAAG GGAAATGGAA GGCAAGAAAC ACGAAGGATC ATGTGGTAAC TGCGAGAGCT    3042

TGCTGAGGGG TGGGAGAGCC AGCTGTGGGG TCCAGACTTG TTGGGGCTTC CCTGCCCCTC    3102

CTGGTCTGTG TCAGTATTAC CACCAGACTG ACTCCAGGAC TCACTGCCCT CCAGAAAACA    3162

GAGGTGACAA ATGTGAGGGA CACTGGGGCC TTTCTTCTCC TTGTAGGGGT CTCTCAGAGG    3222

TTCTTTCCAC AGGCCATCCT CTTATTCCGT TCTGGGGCCC AGGAAGTGGG GAAGAGTAGG    3282

TTCTCGGTAC TTAGGACTTG ATCCTGTGGT TGCCACTGGC CATGCTGCTG CCCAGCTCTA    3342

CCCCTCCCAG GGACCTACCC CTCCCAGGGA CCGACCCCTG GCCCAAGCTC CCCTTGCTGG    3402

CGGGCGCTGC GTGGGCCCTG CACTTGCTGA GGTTCCCCAT CATGGGCAAG GCAAGGGAAT    3462

TCCCACAGCC CTCCAGTGTA CTGAGGGTAC TGGCCTAGCC ATGTGGAATT CCCTACCCTG    3522

ACTCCTTCCC CAAACCCAGG GAAAAGAGCT CTCAATTTTT TATTTTTAAT TTTTGTTTGA    3582
```

AATAAAGTCC TTAGTTAGCC 3602

( 2 ) INFORMATION FOR SEQ ID NO:31:

( i ) SEQUENCE CHARACTERISTICS:
( A ) LENGTH: 829 amino acids
( B ) TYPE: amino acid
( D ) TOPOLOGY: linear ( i i ) MOLECULE TYPE: protein ( x i ) SEQUENCE DESCRIPTION: SEQ ID NO:31:

Met Arg Phe Leu Glu Ala Arg Ser Leu Ala Val Ala Met Gly Asp Thr
1 5 10 15

Val Val Glu Pro Ala Pro Leu Lys Pro Thr Ser Glu Pro Thr Ser Gly
20 25 30

Pro Pro Gly Asn Asn Gly Gly Ser Leu Leu Ser Val Ile Thr Glu Gly
35 40 45

Val Gly Glu Leu Ser Val Ile Asp Pro Glu Val Ala Gln Lys Ala Cys
50 55 60

Gln Glu Val Leu Glu Lys Val Lys Leu Leu His Gly Gly Val Ala Val
65 70 75 80

Ser Ser Arg Gly Thr Pro Leu Glu Leu Val Asn Gly Asp Gly Val Asp
85 90 95

Ser Glu Ile Arg Cys Leu Asp Asp Pro Pro Ala Gln Ile Arg Glu Glu
100 105 110

Glu Asp Glu Met Gly Ala Ala Val Ala Ser Gly Thr Ala Lys Gly Ala
115 120 125

Arg Arg Arg Arg Gln Asn Asn Ser Ala Lys Gln Ser Trp Leu Leu Arg
130 135 140

Leu Phe Glu Ser Lys Leu Phe Asp Ile Ser Met Ala Ile Ser Tyr Leu
145 150 155 160

Tyr Asn Ser Lys Glu Pro Gly Val Gln Ala Tyr Ile Gly Asn Arg Leu
165 170 175

Phe Cys Phe Arg Asn Glu Asp Val Asp Phe Tyr Leu Pro Gln Leu Leu
180 185 190

Asn Met Tyr Ile His Met Asp Glu Asp Val Gly Asp Ala Ile Lys Pro
195 200 205

Tyr Ile Val His Arg Cys Arg Gln Ser Ile Asn Phe Ser Leu Gln Cys
210 215 220

Ala Leu Leu Leu Gly Ala Tyr Ser Ser Asp Met His Ile Ser Thr Gln
225 230 235 240

Arg His Ser Arg Gly Thr Lys Leu Arg Lys Leu Ile Leu Ser Asp Glu
245 250 255

Leu Lys Pro Ala His Arg Lys Arg Glu Leu Pro Ser Leu Ser Pro Ala
260 265 270

Pro Asp Thr Gly Leu Ser Pro Ser Lys Arg Thr His Gln Arg Ser Lys
275 280 285

Ser Asp Ala Thr Ala Ser Ile Ser Leu Ser Ser Asn Leu Lys Arg Thr
290 295 300

Ala Ser Asn Pro Lys Val Glu Asn Glu Asp Glu Glu Leu Ser Ser Ser
305 310 315 320

Thr Glu Ser Ile Asp Asn Ser Phe Ser Ser Pro Val Arg Leu Ala Pro
325 330 335

Glu Arg Glu Phe Ile Lys Ser Leu Met Ala Ile Gly Lys Arg Leu Ala
340 345 350

-continued

Thr Leu Pro Thr Lys Glu Gln Lys Thr Gln Arg Leu Ile Ser Glu Leu
355 360 365

Ser Leu Leu Asn His Lys Leu Pro Ala Arg Val Trp Leu Pro Thr Ala
370 375 380

Gly Phe Asp His His Val Val Arg Val Pro His Thr Gln Ala Val Val
385 390 395 400

Leu Asn Ser Lys Asp Lys Ala Pro Tyr Leu Ile Tyr Val Glu Val Leu
405 410 415

Glu Cys Glu Asn Phe Asp Thr Thr Ser Val Pro Ala Arg Ile Pro Glu
420 425 430

Asn Arg Ile Arg Ser Thr Arg Ser Val Glu Asn Leu Pro Glu Cys Gly
435 440 445

Ile Thr His Glu Gln Arg Ala Gly Ser Phe Ser Thr Val Pro Asn Tyr
450 455 460

Asp Asn Asp Asp Glu Ala Trp Ser Val Asp Asp Ile Gly Glu Leu Gln
465 470 475 480

Val Glu Leu Pro Glu Val His Thr Asn Ser Cys Asp Asn Ile Ser Gln
485 490 495

Phe Ser Val Asp Ser Ile Thr Ser Gln Glu Ser Lys Glu Pro Val Phe
500 505 510

Ile Ala Ala Gly Asp Ile Arg Arg Arg Leu Ser Glu Gln Leu Ala His
515 520 525

Thr Pro Thr Ala Phe Lys Arg Asp Pro Glu Asp Pro Ser Ala Val Ala
530 535 540

Leu Lys Glu Pro Trp Gln Glu Lys Val Arg Arg Ile Arg Glu Gly Ser
545 550 555 560

Pro Tyr Gly His Leu Pro Asn Trp Arg Leu Leu Ser Val Ile Val Lys
565 570 575

Cys Gly Asp Asp Leu Arg Gln Glu Leu Leu Ala Phe Gln Val Leu Lys
580 585 590

Gln Leu Gln Ser Ile Trp Glu Gln Glu Arg Val Pro Leu Trp Ile Lys
595 600 605

Pro Ile Gln Asp Ser Cys Glu Ile Thr Thr Asp Ser Gly Met Ile Glu
610 615 620

Pro Val Val Asn Ala Val Ser Ile His Gln Val Lys Lys Gln Ser Gln
625 630 635 640

Leu Ser Leu Leu Asp Tyr Phe Leu Gln Glu His Gly Ser Tyr Thr Thr
645 650 655

Glu Ala Phe Leu Ser Ala Gln Arg Asn Phe Val Gln Ser Cys Ala Gly
660 665 670

Tyr Cys Leu Val Cys Tyr Leu Leu Gln Val Lys Asp Arg His Asn Gly
675 680 685

Asn Ile Leu Leu Asp Ala Glu Gly His Ile Ile His Ile Asp Phe Gly
690 695 700

Phe Ile Leu Ser Ser Ser Pro Arg Asn Leu Gly Phe Glu Thr Ser Ala
705 710 715 720

Phe Lys Leu Thr Thr Glu Phe Val Asp Val Met Gly Gly Leu Asp Gly
725 730 735

Asp Met Phe Asn Tyr Tyr Lys Met Leu Met Leu Gln Gly Leu Ile Ala
740 745 750

Ala Arg Lys His Met Asp Lys Val Val Gln Ile Val Glu Ile Met Gln
755 760 765

Gln Gly Ser Gln Leu Pro Cys Phe His Gly Ser Ser Thr Ile Arg Asn
770 775 780

-continued

Leu Lys Glu Arg Phe His Met Ser Met Thr Glu Glu Gln Leu Gln Leu
785 790 795 800

Leu Val Glu Gln Met Val Asp Gly Ser Met Arg Ser Ile Thr Thr Lys
805 810 815

Leu Tyr Asp Gly Phe Gln Tyr Leu Thr Asn Gly Ile Met
820 825

( 2 ) INFORMATION FOR SEQ ID NO:32:

( i ) SEQUENCE CHARACTERISTICS:
( A ) LENGTH: 2487 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:32:

ATGAGATTCT TGGAAGCTCG AAGTCTGGCT GTGGCCATGG GAGATACAGT AGTGGAGCCT 60

GCCCCCTTGA AGCCAACTTC TGAGCCCACT TCTGGCCCAC CAGGGAATAA TGGGGGGTCC 120

CTGCTAAGTG TCATCACGGA GGGGGTCGGG GAACTATCAG TGATTGACCC TGAGGTGGCC 180

CAGAAGGCCT GCCAGGAGGT GTTGGAGAAA GTCAAGCTTT TGCATGGAGG CGTGGCAGTC 240

TCTAGCAGAG GCACCCCACT GGAGTTGGTC AATGGGGATG GTGTGGACAG TGAGATCCGT 300

TGCCTAGATG ATCCACCTGC CCAGATCAGG GAGGAGGAAG ATGAGATGGG GGCCGCTGTG 360

GCCTCAGGCA CAGCCAAAGG AGCAAGAAGA CGGCGGCAGA ACAACTCAGC TAAACAGTCT 420

TGGCTGCTGA GGCTGTTTGA GTCAAAACTG TTTGACATCT CCATGGCCAT TTCATACCTG 480

TATAACTCCA AGGAGCCTGG AGTACAAGCC TACATTGGCA ACCGGCTCTT CTGCTTTCGC 540

AACGAGGACG TGGACTTCTA TCTGCCCCAG TTGCTTAACA TGTACATCCA CATGGATGAG 600

GACGTGGGTG ATGCCATTAA GCCCTACATA GTCCACCGTT GCCGCCAGAG CATTAACTTT 660

TCCCTCCAGT GTGCCCTGTT GCTTGGGGCC TATTCTTCAG ACATGCACAT TTCCACTCAA 720

CGACACTCCC GTGGGACCAA GCTACGGAAG CTGATCCTCT CAGATGAGCT AAAGCCAGCT 780

CACAGGAAGA GGGAGCTGCC CTCCTTGAGC CCGGCCCCTG ATACAGGGCT GTCTCCCTCC 840

AAAAGGACTC ACCAGCGCTC TAAGTCAGAT GCCACTGCCA GCATAAGTCT CAGCAGCAAC 900

CTGAAACGAA CAGCCAGCAA CCCTAAAGTG GAGAATGAGG ATGAGGAGCT CTCCTCCAGC 960

ACCGAGAGTA TTGATAATTC ATTCAGTTCC CCTGTTCGAC TGGCTCCTGA GAGAGAATTC 1020

ATCAAGTCCC TGATGGCGAT CGGCAAGCGG CTGGCCACGC TCCCCACCAA AGAGCAGAAA 1080

ACACAGAGGC TGATCTCAGA GCTCTCCCTG CTCAACCATA AGCTCCCTGC CCGAGTCTGG 1140

CTGCCCACTG CTGGCTTTGA CCACCACGTG GTCCGTGTAC CCCACACACA GGCTGTTGTC 1200

CTCAACTCCA AGGACAAGGC TCCCTACCTG ATTTATGTGG AAGTCCTTGA ATGTGAAAAC 1260

TTTGACACCA CCAGTGTCCC TGCCCGGATC CCCGAGAACC GAATTCGGAG TACGAGGTCC 1320

GTAGAAAACT TGCCCGAATG TGGTATTACC CATGAGCAGC GAGCTGGCAG CTTCAGCACT 1380

GTGCCCAACT ATGACAACGA TGATGAGGCC TGGTCGGTGG ATGACATAGG CGAGCTGCAA 1440

GTGGAGCTCC CCGAAGTGCA TACCAACAGC TGTGACAACA TCTCCCAGTT CTCTGTGGAC 1500

AGCATCACCA GCCAGGAGAG CAAGGAGCCT GTGTTCATTG CAGCAGGGGA CATCCGCCGG 1560

CGCCTTTCGG AACAGCTGGC TCATACCCCG ACAGCCTTCA AACGAGACCC AGAAGATCCT 1620

TCTGCAGTTG CTCTCAAAGA GCCCTGGCAG GAGAAAGTAC GGCGGATCAG AGAGGGCTCC 1680

CCCTACGGCC ATCTCCCCAA TTGGCGGCTC CTGTCAGTCA TTGTCAAGTG TGGGGATGAC 1740

CTTCGGCAAG AGCTTCTGGC CTTTCAGGTG TTGAAGCAAC TGCAGTCCAT TTGGGAACAG 1800

GAGCGAGTGC CCCTTTGGAT CAAGCCAATA CAAGATTCTT GTGAAATTAC GACTGATAGT 1860

GGCATGATTG AACCAGTGGT CAATGCTGTG TCCATCCATC AGGTGAAGAA ACAGTCACAG 1920

CTCTCCTTGC TCGATTACTT CCTACAGGAG CACGGCAGTT ACACCACTGA GGCATTCCTC 1980

AGTGCACAGC GCAATTTTGT GCAAAGTTGT GCTGGGTACT GCTTGGTCTG CTACCTGCTG 2040

CAAGTCAAGG ACAGACACAA TGGGAATATC CTTTTGGACG CAGAAGGCCA CATCATCCAC 2100

ATCGACTTTG GCTTCATCCT CTCCAGCTCA CCCCGAAATC TGGGCTTTGA GACGTCAGCC 2160

TTTAAGCTGA CCACAGAGTT TGTGGATGTG ATGGGCGGCC TGGATGGCGA CATGTTCAAC 2220

TACTATAAGA TGCTGATGCT GCAAGGGCTG ATTGCCGCTC GGAAACACAT GGACAAGGTG 2280

GTGCAGATCG TGGAGATCAT GCAGCAAGGT TCTCAGCTTC CTTGCTTCCA TGGCTCCAGC 2340

ACCATTCGAA ACCTCAAAGA GAGGTTCCAC ATGAGCATGA CTGAGGAGCA GCTGCAGCTG 2400

CTGGTGGAGC AGATGGTGGA TGGCAGTATG CGGTCTATCA CCACCAAACT CTATGACGGC 2460

TTCCAGTACC TCACCAACGG CATCATG 2487

( 2 ) INFORMATION FOR SEQ ID NO:33:

( i ) SEQUENCE CHARACTERISTICS:
( A ) LENGTH: 3324 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-428B12c1

( i x ) FEATURE:
( A ) NAME/KEY: CDS
( B ) LOCATION: 115..2601

( x i ) SEQUENCE DESCRIPTION: SEQ ID NO:33:

CCGGAATTCC GGGAAGGCCG GAGCAAGTTT TGAAGAAGTC CCTATCAGAT TACACTTGGT 60

TGACTACTCC GGAGCAGCCA CTAAGAGGGA TGAACAGGCC TGCGTGGAAA TTGA ATG 117
Met
1

AGA TTC TTG GAA GCT CGA AGT CTG GCT GTG GCC ATG GGA GAT ACA GTA 165
Arg Phe Leu Glu Ala Arg Ser Leu Ala Val Ala Met Gly Asp Thr Val
5 10 15

GTG GAG CCT GCC CCC TTG AAG CCA ACT TCT GAG CCC ACT TCT GGC CCA 213
Val Glu Pro Ala Pro Leu Lys Pro Thr Ser Glu Pro Thr Ser Gly Pro
20 25 30

CCA GGG AAT AAT GGG GGG TCC CTG CTA AGT GTC ATC ACG GAG GGG GTC 261
Pro Gly Asn Asn Gly Gly Ser Leu Leu Ser Val Ile Thr Glu Gly Val
35 40 45

GGG GAA CTA TCA GTG ATT GAC CCT GAG GTG GCC CAG AAG GCC TGC CAG 309
Gly Glu Leu Ser Val Ile Asp Pro Glu Val Ala Gln Lys Ala Cys Gln
50 55 60 65

GAG GTG TTG GAG AAA GTC AAG CTT TTG CAT GGA GGC GTG GCA GTC TCT 357
Glu Val Leu Glu Lys Val Lys Leu Leu His Gly Gly Val Ala Val Ser
70 75 80

AGC AGA GGC ACC CCA CTG GAG TTG GTC AAT GGG GAT GGT GTG GAC AGT 405
Ser Arg Gly Thr Pro Leu Glu Leu Val Asn Gly Asp Gly Val Asp Ser

-continued

```
            85                  90                  95

GAG ATC CGT TGC CTA GAT GAT CCA CCT GCC CAG ATC AGG GAG GAG GAA         453
Glu Ile Arg Cys Leu Asp Asp Pro Pro Ala Gln Ile Arg Glu Glu Glu
        100                 105                 110

GAT GAG ATG GGG GCC GCT GTG GCC TCA GGC ACA GCC AAA GGA GCA AGA         501
Asp Glu Met Gly Ala Ala Val Ala Ser Gly Thr Ala Lys Gly Ala Arg
    115                 120                 125

AGA CGG CGG CAG AAC AAC TCA GCT AAA CAG TCT TGG CTG CTG AGG CTG         549
Arg Arg Arg Gln Asn Asn Ser Ala Lys Gln Ser Trp Leu Leu Arg Leu
130                 135                 140                 145

TTT GAG TCA AAA CTG TTT GAC ATC TCC ATG GCC ATT TCA TAC CTG TAT         597
Phe Glu Ser Lys Leu Phe Asp Ile Ser Met Ala Ile Ser Tyr Leu Tyr
                150                 155                 160

AAC TCC AAG GAG CCT GGA GTA CAA GCC TAC ATT GGC AAC CGG CTC TTC         645
Asn Ser Lys Glu Pro Gly Val Gln Ala Tyr Ile Gly Asn Arg Leu Phe
            165                 170                 175

TGC TTT CGC AAC GAG GAC GTG GAC TTC TAT CTG CCC CAG TTG CTT AAC         693
Cys Phe Arg Asn Glu Asp Val Asp Phe Tyr Leu Pro Gln Leu Leu Asn
        180                 185                 190

ATG TAC ATC CAC ATG GAT GAG GAC GTG GGT GAT GCC ATT AAG CCC TAC         741
Met Tyr Ile His Met Asp Glu Asp Val Gly Asp Ala Ile Lys Pro Tyr
    195                 200                 205

ATA GTC CAC CGT TGC CGC CAG AGC ATT AAC TTT TCC CTC CAG TGT GCC         789
Ile Val His Arg Cys Arg Gln Ser Ile Asn Phe Ser Leu Gln Cys Ala
210                 215                 220                 225

CTG TTG CTT GGG GCC TAT TCT TCA GAC ATG CAC ATT TCC ACT CAA CGA         837
Leu Leu Leu Gly Ala Tyr Ser Ser Asp Met His Ile Ser Thr Gln Arg
                230                 235                 240

CAC TCC CGT GGG ACC AAG CTA CGG AAG CTG ATC CTC TCA GAT GAG CTA         885
His Ser Arg Gly Thr Lys Leu Arg Lys Leu Ile Leu Ser Asp Glu Leu
            245                 250                 255

AAG CCA GCT CAC AGG AAG AGG GAG CTG CCC TCC TTG AGC CCG GCC CCT         933
Lys Pro Ala His Arg Lys Arg Glu Leu Pro Ser Leu Ser Pro Ala Pro
        260                 265                 270

GAT ACA GGG CTG TCT CCC TCC AAA AGG ACT CAC CAG CGC TCT AAG TCA         981
Asp Thr Gly Leu Ser Pro Ser Lys Arg Thr His Gln Arg Ser Lys Ser
    275                 280                 285

GAT GCC ACT GCC AGC ATA AGT CTC AGC AGC AAC CTG AAA CGA ACA GCC        1029
Asp Ala Thr Ala Ser Ile Ser Leu Ser Ser Asn Leu Lys Arg Thr Ala
290                 295                 300                 305

AGC AAC CCT AAA GTG GAG AAT GAG GAT GAG GAG CTC TCC TCC AGC ACC        1077
Ser Asn Pro Lys Val Glu Asn Glu Asp Glu Glu Leu Ser Ser Ser Thr
                310                 315                 320

GAG AGT ATT GAT AAT TCA TTC AGT TCC CCT GTT CGA CTG GCT CCT GAG        1125
Glu Ser Ile Asp Asn Ser Phe Ser Ser Pro Val Arg Leu Ala Pro Glu
            325                 330                 335

AGA GAA TTC ATC AAG TCC CTG ATG GCG ATC GGC AAG CGG CTG GCC ACG        1173
Arg Glu Phe Ile Lys Ser Leu Met Ala Ile Gly Lys Arg Leu Ala Thr
        340                 345                 350

CTC CCC ACC AAA GAG CAG AAA ACA CAG AGG CTG ATC TCA GAG CTC TCC        1221
Leu Pro Thr Lys Glu Gln Lys Thr Gln Arg Leu Ile Ser Glu Leu Ser
    355                 360                 365

CTG CTC AAC CAT AAG CTC CCT GCC CGA GTC TGG CTG CCC ACT GCT GGC        1269
Leu Leu Asn His Lys Leu Pro Ala Arg Val Trp Leu Pro Thr Ala Gly
370                 375                 380                 385

TTT GAC CAC CAC GTG GTC CGT GTA CCC CAC ACA CAG GCT GTT GTC CTC        1317
Phe Asp His His Val Val Arg Val Pro His Thr Gln Ala Val Val Leu
                390                 395                 400

AAC TCC AAG GAC AAG GCT CCC TAC CTG ATT TAT GTG GAA GTC CTT GAA        1365
Asn Ser Lys Asp Lys Ala Pro Tyr Leu Ile Tyr Val Glu Val Leu Glu
```

-continued

```
            405                 410                 415

TGT GAA AAC TTT GAC ACC ACC AGT GTC CCT GCC CGG ATC CCC GAG AAC   1413
Cys Glu Asn Phe Asp Thr Thr Ser Val Pro Ala Arg Ile Pro Glu Asn
        420                 425                 430

CGA ATT CGG AGT ACG AGG TCC GTA GAA AAC TTG CCC GAA TGT GGT ATT   1461
Arg Ile Arg Ser Thr Arg Ser Val Glu Asn Leu Pro Glu Cys Gly Ile
    435                 440                 445

ACC CAT GAG CAG CGA GCT GGC AGC TTC AGC ACT GTG CCC AAC TAT GAC   1509
Thr His Glu Gln Arg Ala Gly Ser Phe Ser Thr Val Pro Asn Tyr Asp
450                 455                 460                 465

AAC GAT GAT GAG GCC TGG TCG GTG GAT GAC ATA GGC GAG CTG CAA GTG   1557
Asn Asp Asp Glu Ala Trp Ser Val Asp Asp Ile Gly Glu Leu Gln Val
                470                 475                 480

GAG CTC CCC GAA GTG CAT ACC AAC AGC TGT GAC AAC ATC TCC CAG TTC   1605
Glu Leu Pro Glu Val His Thr Asn Ser Cys Asp Asn Ile Ser Gln Phe
            485                 490                 495

TCT GTG GAC AGC ATC ACC AGC CAG GAG AGC AAG GAG CCT GTG TTC ATT   1653
Ser Val Asp Ser Ile Thr Ser Gln Glu Ser Lys Glu Pro Val Phe Ile
        500                 505                 510

GCA GCA GGG GAC ATC CGC CGG CGC CTT TCG GAA CAG CTG GCT CAT ACC   1701
Ala Ala Gly Asp Ile Arg Arg Arg Leu Ser Glu Gln Leu Ala His Thr
    515                 520                 525

CCG ACA GCC TTC AAA CGA GAC CCA GAA GAT CCT TCT GCA GTT GCT CTC   1749
Pro Thr Ala Phe Lys Arg Asp Pro Glu Asp Pro Ser Ala Val Ala Leu
530                 535                 540                 545

AAA GAG CCC TGG CAG GAG AAA GTA CGG CGG ATC AGA GAG GGC TCC CCC   1797
Lys Glu Pro Trp Gln Glu Lys Val Arg Arg Ile Arg Glu Gly Ser Pro
                550                 555                 560

TAC GGC CAT CTC CCC AAT TGG CGG CTC CTG TCA GTC ATT GTC AAG TGT   1845
Tyr Gly His Leu Pro Asn Trp Arg Leu Leu Ser Val Ile Val Lys Cys
            565                 570                 575

GGG GAT GAC CTT CGG CAA GAG CTT CTG GCC TTT CAG GTG TTG AAG CAA   1893
Gly Asp Asp Leu Arg Gln Glu Leu Leu Ala Phe Gln Val Leu Lys Gln
        580                 585                 590

CTG CAG TCC ATT TGG GAA CAG GAG CGA GTG CCC CTT TGG ATC AAG CCA   1941
Leu Gln Ser Ile Trp Glu Gln Glu Arg Val Pro Leu Trp Ile Lys Pro
    595                 600                 605

ATA CAA GAT TCT TGT GAA ATT ACG ACT GAT AGT GGC ATG ATT GAA CCA   1989
Ile Gln Asp Ser Cys Glu Ile Thr Thr Asp Ser Gly Met Ile Glu Pro
610                 615                 620                 625

GTG GTC AAT GCT GTG TCC ATC CAT CAG GTG AAG AAA CAG TCA CAG CTC   2037
Val Val Asn Ala Val Ser Ile His Gln Val Lys Lys Gln Ser Gln Leu
                630                 635                 640

TCC TTG CTC GAT TAC TTC CTA CAG GAG CAC GGC AGT TAC ACC ACT GAG   2085
Ser Leu Leu Asp Tyr Phe Leu Gln Glu His Gly Ser Tyr Thr Thr Glu
            645                 650                 655

GCA TTC CTC AGT GCA CAG CGC AAT TTT GTG CAA AGT TGT GCT GGG TAC   2133
Ala Phe Leu Ser Ala Gln Arg Asn Phe Val Gln Ser Cys Ala Gly Tyr
        660                 665                 670

TGC TTG GTC TGC TAC CTG CTG CAA GTC AAG GAC AGA CAC AAT GGG AAT   2181
Cys Leu Val Cys Tyr Leu Leu Gln Val Lys Asp Arg His Asn Gly Asn
    675                 680                 685

ATC CTT TTG GAC GCA GAA GGC CAC ATC ATC CAC ATC GAC TTT GGC TTC   2229
Ile Leu Leu Asp Ala Glu Gly His Ile Ile His Ile Asp Phe Gly Phe
690                 695                 700                 705

ATC CTC TCC AGC TCA CCC CGA AAT CTG GGC TTT GAG ACG TCA GCC TTT   2277
Ile Leu Ser Ser Ser Pro Arg Asn Leu Gly Phe Glu Thr Ser Ala Phe
                710                 715                 720

AAG CTG ACC ACA GAG TTT GTG GAT GTG ATG GGC GGC CTG GAT GGC GAC   2325
Lys Leu Thr Thr Glu Phe Val Asp Val Met Gly Gly Leu Asp Gly Asp
```

-continued

```
                    725                           730                           735

ATG TTC AAC TAC TAT AAG ATG CTG ATG CTG CAA GGG CTG ATT GCC GCT    2373
Met Phe Asn Tyr Tyr Lys Met Leu Met Leu Gln Gly Leu Ile Ala Ala
            740                     745                     750

CGG AAA CAC ATG GAC AAG GTG GTG CAG ATC GTG GAG ATC ATG CAG CAA    2421
Arg Lys His Met Asp Lys Val Val Gln Ile Val Glu Ile Met Gln Gln
        755                     760                     765

GGT TCT CAG CTT CCT TGC TTC CAT GGC TCC AGC ACC ATT CGA AAC CTC    2469
Gly Ser Gln Leu Pro Cys Phe His Gly Ser Ser Thr Ile Arg Asn Leu
770                     775                     780                     785

AAA GAG AGG TTC CAC ATG AGC ATG ACT GAG GAG CAG CTG CAG CTG CTG    2517
Lys Glu Arg Phe His Met Ser Met Thr Glu Glu Gln Leu Gln Leu Leu
                790                     795                     800

GTG GAG CAG ATG GTG GAT GGC AGT ATG CGG TCT ATC ACC ACC AAA CTC    2565
Val Glu Gln Met Val Asp Gly Ser Met Arg Ser Ile Thr Thr Lys Leu
            805                     810                     815

TAT GAC GGC TTC CAG TAC CTC ACC AAC GGC ATC ATG TGA CACGCTCCTC    2614
Tyr Asp Gly Phe Gln Tyr Leu Thr Asn Gly Ile Met  *
        820                     825                     830

AGCCCAGGAG TGGTGGGGGG TCCAGGGCAC CCTCCCTAGA GGGCCCTTGT CTGAGAAACC    2674

CCAAACCAGG AAACCCCACC TACCCAACCA TCCACCCAAG GGAAATGGAA GGCAAGAAAC    2734

ACGAAGGATC ATGTGGTAAC TGCGAGAGCT TGCTGAGGGG TGGGAGAGCC AGCTGTGGGG    2794

TCCAGACTTG TTGGGGCTTC CCTGCCCCTC CTGGTCTGTG TCAGTATTAC CACCAGACTG    2854

ACTCCAGGAC TCACTGCCCT CCAGAAAACA GAGGTGACAA ATGTGAGGGA CACTGGGGCC    2914

TTTCTTCTCC TTGTAGGGGT CTCTCAGAGG TTCTTTCCAC AGGCCATCCT CTTATTCCGT    2974

TCTGGGGCCC AGGAAGTGGG GAAGAGTAGG TTCTCGGTAC TTAGGACTTG ATCCTGTGGT    3034

TGCCACTGGC CATGCTGCTG CCCAGCTCTA CCCCTCCCAG GGACCTACCC CTCCCAGGGA    3094

CCGACCCCTG GCCCAAGCTC CCCTTGCTGG CGGGCGCTGC GTGGGCCCTG CACTTGCTGA    3154

GGTTCCCCAT CATGGGCAAG GCAAGGGAAT TCCCACAGCC CTCCAGTGTA CTGAGGGTAC    3214

TGGCCTAGCC ATGTGGAATT CCCTACCCTG ACTCCTTCCC CAAACCCAGG GAAAAGAGCT    3274

CTCAATTTTT TATTTTTAAT TTTTGTTTGA AATAAAGTCC TTAGTTAGCC              3324
```

(2) INFORMATION FOR SEQ ID NO:34:

(i) SEQUENCE CHARACTERISTICS:
(A) LENGTH: 810 amino acids
(B) TYPE: amino acid
(D) TOPOLOGY: linear (ii) MOLECULE TYPE: protein (xi) SEQUENCE DESCRIPTION: SEQ ID NO:34:

```
Met Pro Met Asp Leu Ile Leu Val Val Trp Phe Cys Val Cys Thr Ala
  1               5                  10                  15

Arg Thr Val Val Gly Phe Gly Met Asp Pro Asp Leu Gln Met Asp Ile
             20                  25                  30

Val Thr Glu Leu Asp Leu Val Asn Thr Thr Leu Gly Val Ala Gln Val
         35                  40                  45

Ser Gly Met His Asn Ala Ser Lys Ala Phe Leu Phe Gln Asp Ile Glu
     50                  55                  60

Arg Glu Ile His Ala Ala Pro His Val Ser Glu Lys Leu Ile Gln Leu
 65                  70                  75                  80

Phe Gln Asn Lys Ser Glu Phe Thr Ile Leu Ala Thr Val Gln Gln Lys
                 85                  90                  95
```

-continued

| | | | | | | | | | | | | | | | |
|---|---|---|---|---|---|---|---|---|---|---|---|---|---|---|---|
| Pro | Ser | Thr | Ser | Gly | Val | Ile | Leu | Ser | Ile | Arg | Glu | Leu | Glu | His | Ser |
| | | | 100 | | | | | 105 | | | | | 110 | | |
| Tyr | Phe | Glu | Leu | Glu | Ser | Ser | Gly | Leu | Arg | Asp | Glu | Ile | Arg | Tyr | His |
| | | 115 | | | | | 120 | | | | | 125 | | | |
| Tyr | Ile | His | Asn | Gly | Lys | Pro | Arg | Thr | Glu | Ala | Leu | Pro | Tyr | Arg | Met |
| | 130 | | | | | 135 | | | | | 140 | | | | |
| Ala | Asp | Gly | Gln | Trp | His | Lys | Val | Ala | Leu | Ser | Val | Ser | Ala | Ser | His |
| 145 | | | | | 150 | | | | | 155 | | | | | 160 |
| Leu | Leu | Leu | His | Val | Asp | Cys | Asn | Arg | Ile | Tyr | Glu | Arg | Val | Ile | Asp |
| | | | | 165 | | | | | 170 | | | | | 175 | |
| Pro | Pro | Asp | Thr | Asn | Leu | Pro | Pro | Gly | Ile | Asn | Leu | Trp | Leu | Gly | Gln |
| | | | 180 | | | | | 185 | | | | | 190 | | |
| Arg | Asn | Gln | Lys | His | Gly | Leu | Phe | Lys | Gly | Ile | Ile | Gln | Asp | Gly | Lys |
| | | 195 | | | | | 200 | | | | | 205 | | | |
| Ile | Ile | Phe | Met | Pro | Asn | Gly | Tyr | Ile | Thr | Gln | Cys | Pro | Asn | Leu | Asn |
| | 210 | | | | | 215 | | | | | 220 | | | | |
| His | Thr | Cys | Pro | Thr | Cys | Ser | Asp | Phe | Leu | Ser | Leu | Val | Gln | Gly | Ile |
| 225 | | | | | 230 | | | | | 235 | | | | | 240 |
| Met | Asp | Leu | Gln | Glu | Leu | Leu | Ala | Lys | Met | Thr | Ala | Lys | Leu | Asn | Tyr |
| | | | | 245 | | | | | 250 | | | | | 255 | |
| Ala | Glu | Thr | Arg | Leu | Ser | Gln | Leu | Glu | Asn | Cys | His | Cys | Glu | Lys | Thr |
| | | | 260 | | | | | 265 | | | | | 270 | | |
| Cys | Gln | Val | Ser | Gly | Leu | Leu | Tyr | Arg | Asp | Gln | Asp | Ser | Trp | Val | Asp |
| | | 275 | | | | | 280 | | | | | 285 | | | |
| Gly | Asp | His | Cys | Arg | Asn | Cys | Thr | Cys | Lys | Ser | Gly | Ala | Val | Glu | Cys |
| | 290 | | | | | 295 | | | | | 300 | | | | |
| Arg | Arg | Met | Ser | Cys | Pro | Pro | Leu | Asn | Cys | Ser | Pro | Asp | Ser | Leu | Pro |
| 305 | | | | | 310 | | | | | 315 | | | | | 320 |
| Val | His | Ile | Ala | Gly | Gln | Cys | Cys | Lys | Val | Cys | Arg | Pro | Lys | Cys | Ile |
| | | | | 325 | | | | | 330 | | | | | 335 | |
| Tyr | Gly | Gly | Lys | Val | Leu | Ala | Glu | Gly | Gln | Arg | Ile | Leu | Thr | Lys | Ser |
| | | | 340 | | | | | 345 | | | | | 350 | | |
| Cys | Arg | Glu | Cys | Arg | Gly | Gly | Val | Leu | Val | Lys | Ile | Thr | Glu | Met | Cys |
| | | 355 | | | | | 360 | | | | | 365 | | | |
| Pro | Pro | Leu | Asn | Cys | Ser | Glu | Lys | Asp | His | Ile | Leu | Pro | Glu | Asn | Gln |
| | 370 | | | | | 375 | | | | | 380 | | | | |
| Cys | Cys | Arg | Val | Cys | Arg | Gly | His | Asn | Phe | Cys | Ala | Glu | Gly | Pro | Lys |
| 385 | | | | | 390 | | | | | 395 | | | | | 400 |
| Cys | Gly | Glu | Asn | Ser | Glu | Cys | Lys | Asn | Trp | Asn | Thr | Lys | Ala | Thr | Cys |
| | | | | 405 | | | | | 410 | | | | | 415 | |
| Glu | Cys | Lys | Ser | Gly | Tyr | Ile | Ser | Val | Gln | Gly | Asp | Ser | Ala | Tyr | Cys |
| | | | 420 | | | | | 425 | | | | | 430 | | |
| Glu | Asp | Ile | Asp | Glu | Cys | Ala | Ala | Lys | Met | His | Tyr | Cys | His | Ala | Asn |
| | | 435 | | | | | 440 | | | | | 445 | | | |
| Thr | Val | Cys | Val | Asn | Leu | Pro | Gly | Leu | Tyr | Arg | Cys | Asp | Cys | Val | Pro |
| | 450 | | | | | 455 | | | | | 460 | | | | |
| Gly | Tyr | Ile | Arg | Val | Asp | Asp | Phe | Ser | Cys | Thr | Glu | His | Asp | Glu | Cys |
| 465 | | | | | 470 | | | | | 475 | | | | | 480 |
| Gly | Ser | Gly | Gln | His | Asn | Cys | Asp | Glu | Asn | Ala | Ile | Cys | Thr | Asn | Thr |
| | | | | 485 | | | | | 490 | | | | | 495 | |
| Val | Gln | Gly | His | Ser | Cys | Thr | Cys | Lys | Pro | Gly | Tyr | Val | Gly | Asn | Gly |
| | | | 500 | | | | | 505 | | | | | 510 | | |
| Thr | Ile | Cys | Arg | Ala | Phe | Cys | Glu | Glu | Gly | Cys | Arg | Tyr | Gly | Gly | Thr |
| | | 515 | | | | | 520 | | | | | 525 | | | |

-continued

Cys Val Ala Pro Asn Lys Cys Val Cys Pro Ser Gly Phe Thr Gly Ser
530 535 540

His Cys Glu Lys Asp Ile Asp Glu Cys Ser Glu Gly Ile Ile Glu Cys
545 550 555 560

His Asn His Ser Arg Cys Val Asn Leu Pro Gly Trp Tyr His Cys Glu
565 570 575

Cys Arg Ser Gly Phe His Asp Asp Gly Thr Tyr Ser Leu Ser Gly Glu
580 585 590

Ser Cys Ile Asp Ile Asp Glu Cys Ala Leu Arg Thr His Thr Cys Trp
595 600 605

Asn Asp Ser Ala Cys Ile Asn Leu Ala Gly Gly Phe Asp Cys Leu Cys
610 615 620

Pro Ser Gly Pro Ser Cys Ser Gly Asp Cys Pro His Glu Gly Gly Leu
625 630 635 640

Lys His Asn Gly Gln Val Trp Thr Leu Lys Glu Asp Arg Cys Ser Val
645 650 655

Cys Ser Cys Lys Asp Gly Lys Ile Phe Cys Arg Arg Thr Ala Cys Asp
660 665 670

Cys Gln Asn Pro Ser Ala Asp Leu Phe Cys Cys Pro Glu Cys Asp Thr
675 680 685

Arg Val Thr Ser Gln Cys Leu Asp Gln Asn Gly His Lys Leu Tyr Arg
690 695 700

Ser Gly Asp Asn Trp Thr His Ser Cys Gln Gln Cys Arg Cys Leu Glu
705 710 715 720

Gly Glu Val Asp Cys Trp Pro Leu Thr Cys Pro Asn Leu Ser Cys Glu
725 730 735

Tyr Thr Ala Ile Leu Glu Gly Glu Cys Cys Pro Arg Cys Val Ser Asp
740 745 750

Pro Cys Leu Ala Asp Asn Ile Thr Tyr Asp Ile Arg Lys Thr Cys Leu
755 760 765

Asp Ser Tyr Gly Val Ser Arg Leu Ser Gly Ser Val Trp Thr Met Ala
770 775 780

Gly Ser Pro Cys Thr Thr Cys Lys Cys Lys Asn Gly Arg Val Cys Cys
785 790 795 800

Ser Val Asp Phe Glu Cys Leu Gln Asn Asn
805 810

( 2 ) INFORMATION FOR SEQ ID NO:35:

( i ) SEQUENCE CHARACTERISTICS:
( A ) LENGTH: 2430 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:35:

ATGCCGATGG ATTTGATTTT AGTTGTGTGG TTCTGTGTGT GCACTGCCAG GACAGTGGTG 60

GGCTTTGGGA TGGACCCTGA CCTTCAGATG GATATCGTCA CCGAGCTTGA CCTTGTGAAC 120

ACCACCCTTG GAGTTGCTCA GGTGTCTGGA ATGCACAATG CCAGCAAAGC ATTTTTATTT 180

CAAGACATAG AAAGAGAGAT CCATGCAGCT CCTCATGTGA GTGAGAAATT AATTCAGCTG 240

TTCCAGAACA AGAGTGAATT CACCATTTTG GCCACTGTAC AGCAGAAGCC ATCCACTTCA 300

GGAGTGATAC TGTCCATTCG AGAACTGGAG CACAGCTATT TTGAACTGGA GAGCAGTGGC 360

-continued

```
CTGAGGGATG AGATTCGGTA TCACTACATA CACAATGGGA AGCCAAGGAC AGAGGCACTT   420
CCTTACCGCA TGGCAGATGG ACAATGGCAC AAGGTTGCAC TGTCAGTTAG CGCCTCTCAT   480
CTCCTGCTCC ATGTCGACTG TAACAGGATT TATGAGCGTG TGATAGACCC TCCAGATACC   540
AACCTTCCCC CAGGAATCAA TTTATGGCTT GGCCAGCGCA ACCAAAAGCA TGGCTTATTC   600
AAAGGGATCA TCCAAGATGG GAAGATCATC TTTATGCCGA ATGGATATAT AACACAGTGT   660
CCAAATCTAA ATCACACTTG CCCAACCTGC AGTGATTTCT TAAGCCTGGT GCAAGGAATA   720
ATGGATTTAC AAGAGCTTTT GGCCAAGATG ACTGCAAAAC TAAATTATGC AGAGACAAGA   780
CTTAGTCAAT TGGAAAACTG TCATTGTGAG AAGACTTGTC AAGTGAGTGG ACTGCTCTAT   840
CGAGATCAAG ACTCTTGGGT AGATGGTGAC CATTGCAGGA ACTGCACTTG CAAAAGTGGT   900
GCCGTGGAAT GCCGAAGGAT GTCCTGTCCC CCTCTCAATT GCTCCCCAGA CTCCCTCCCA   960
GTACACATTG CTGGCCAGTG CTGTAAGGTC TGCCGACCAA AATGTATCTA TGGAGGAAAA  1020
GTTCTTGCAG AAGGCCAGCG GATTTTAACC AAGAGCTGTC GGGAATGCCG AGGTGGAGTT  1080
TTAGTAAAAA TTACAGAAAT GTGTCCTCCT TTGAACTGCT CAGAAAAGGA TCACATTCTT  1140
CCTGAGAATC AGTGCTGCCG TGTCTGTAGA GGTCATAACT TTTGTGCAGA AGGACCTAAA  1200
TGTGGTGAAA ACTCAGAGTG CAAAAACTGG AATACAAAAG CTACTTGTGA GTGCAAGAGT  1260
GGTTACATCT CTGTCCAGGG AGACTCTGCC TACTGTGAAG ATATTGATGA GTGTGCAGCT  1320
AAGATGCATT ACTGTCATGC CAATACTGTG TGTGTCAACC TTCCTGGGTT ATATCGCTGT  1380
GACTGTGTCC CAGGATACAT TCGTGTGGAT GACTTCTCTT GTACAGAACA CGATGAATGT  1440
GGCAGCGGCC AGCACAACTG TGATGAGAAT GCCATCTGCA CCAACACTGT CCAGGGACAC  1500
AGCTGCACCT GCAAACCGGG CTACGTGGGG AACGGGACCA TCTGCAGAGC TTTCTGTGAA  1560
GAGGGCTGCA GATACGGTGG AACGTGTGTG GCTCCCAACA AATGTGTCTG TCCATCTGGA  1620
TTCACAGGAA GCCACTGCGA GAAAGATATT GATGAATGTT CAGAGGGAAT CATTGAGTGC  1680
CACAACCATT CCCGCTGCGT TAACCTGCCA GGGTGGTACC ACTGTGAGTG CAGAAGCGGT  1740
TTCCATGACG ATGGGACCTA TTCACTGTCC GGGGAGTCCT GTATTGACAT TGATGAATGT  1800
GCCTTAAGAA CTCACACCTG TTGGAACGAT TCTGCCTGCA TCAACCTGGC AGGGGGTTTT  1860
GACTGTCTCT GCCCCTCTGG GCCCTCCTGC TCTGGTGACT GTCCTCATGA AGGGGGGCTG  1920
AAGCACAATG GCCAGGTGTG GACCTTGAAA GAAGACAGGT GTTCTGTCTG CTCCTGCAAG  1980
GATGGCAAGA TATTCTGCCG ACGGACAGCT TGTGATTGCC AGAATCCAAG TGCTGACCTA  2040
TTCTGTTGCC CAGAATGTGA CACCAGAGTC ACAAGTCAAT GTTTAGACCA AAATGGTCAC  2100
AAGCTGTATC GAAGTGGAGA CAATTGGACC CATAGCTGTC AGCAGTGTCG GTGTCTGGAA  2160
GGAGAGGTAG ATTGCTGGCC ACTCACTTGC CCCAACTTGA GCTGTGAGTA TACAGCTATC  2220
TTAGAAGGGG AATGTTGTCC CCGCTGTGTC AGTGACCCCT GCCTAGCTGA TAACATCACC  2280
TATGACATCA GAAAAACTTG CCTGGACAGC TATGGTGTTT CACGGCTTAG TGGCTCAGTG  2340
TGGACGATGG CTGGATCTCC CTGCACAACC TGTAAATGCA AGAATGGAAG AGTCTGTTGT  2400
TCTGTGGATT TTGAGTGTCT TCAAAATAAT                                   2430
```

( 2 ) INFORMATION FOR SEQ ID NO:36:

( i ) SEQUENCE CHARACTERISTICS:
( A ) LENGTH: 2977 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-073E07

( i x ) FEATURE:
( A ) NAME/KEY: CDS
( B ) LOCATION: 103..2532

( x i ) SEQUENCE DESCRIPTION: SEQ ID NO:36:

```
TAGCAAGTTT GGCGGCTCCA AGCCAGGCGC GCCTCAGGAT CCAGGCTCAT TTGCTTCCAC      60

CTAGCTTCGG TGCCCCCTGC TAGGCGGGGA CCCTCGAGAG CG ATG CCG ATG GAT        114
                                               Met Pro Met Asp
                                                1

TTG ATT TTA GTT GTG TGG TTC TGT GTG TGC ACT GCC AGG ACA GTG GTG       162
Leu Ile Leu Val Val Trp Phe Cys Val Cys Thr Ala Arg Thr Val Val
 5                  10                  15                  20

GGC TTT GGG ATG GAC CCT GAC CTT CAG ATG GAT ATC GTC ACC GAG CTT       210
Gly Phe Gly Met Asp Pro Asp Leu Gln Met Asp Ile Val Thr Glu Leu
                25                  30                  35

GAC CTT GTG AAC ACC ACC CTT GGA GTT GCT CAG GTG TCT GGA ATG CAC       258
Asp Leu Val Asn Thr Thr Leu Gly Val Ala Gln Val Ser Gly Met His
            40                  45                  50

AAT GCC AGC AAA GCA TTT TTA TTT CAA GAC ATA GAA AGA GAG ATC CAT       306
Asn Ala Ser Lys Ala Phe Leu Phe Gln Asp Ile Glu Arg Glu Ile His
        55                  60                  65

GCA GCT CCT CAT GTG AGT GAG AAA TTA ATT CAG CTG TTC CAG AAC AAG       354
Ala Ala Pro His Val Ser Glu Lys Leu Ile Gln Leu Phe Gln Asn Lys
    70                  75                  80

AGT GAA TTC ACC ATT TTG GCC ACT GTA CAG CAG AAG CCA TCC ACT TCA       402
Ser Glu Phe Thr Ile Leu Ala Thr Val Gln Gln Lys Pro Ser Thr Ser
 85                  90                  95                 100

GGA GTG ATA CTG TCC ATT CGA GAA CTG GAG CAC AGC TAT TTT GAA CTG       450
Gly Val Ile Leu Ser Ile Arg Glu Leu Glu His Ser Tyr Phe Glu Leu
                105                 110                 115

GAG AGC AGT GGC CTG AGG GAT GAG ATT CGG TAT CAC TAC ATA CAC AAT       498
Glu Ser Ser Gly Leu Arg Asp Glu Ile Arg Tyr His Tyr Ile His Asn
            120                 125                 130

GGG AAG CCA AGG ACA GAG GCA CTT CCT TAC CGC ATG GCA GAT GGA CAA       546
Gly Lys Pro Arg Thr Glu Ala Leu Pro Tyr Arg Met Ala Asp Gly Gln
        135                 140                 145

TGG CAC AAG GTT GCA CTG TCA GTT AGC GCC TCT CAT CTC CTG CTC CAT       594
Trp His Lys Val Ala Leu Ser Val Ser Ala Ser His Leu Leu Leu His
    150                 155                 160

GTC GAC TGT AAC AGG ATT TAT GAG CGT GTG ATA GAC CCT CCA GAT ACC       642
Val Asp Cys Asn Arg Ile Tyr Glu Arg Val Ile Asp Pro Pro Asp Thr
165                 170                 175                 180

AAC CTT CCC CCA GGA ATC AAT TTA TGG CTT GGC CAG CGC AAC CAA AAG       690
Asn Leu Pro Pro Gly Ile Asn Leu Trp Leu Gly Gln Arg Asn Gln Lys
                185                 190                 195

CAT GGC TTA TTC AAA GGG ATC ATC CAA GAT GGG AAG ATC ATC TTT ATG       738
His Gly Leu Phe Lys Gly Ile Ile Gln Asp Gly Lys Ile Ile Phe Met
            200                 205                 210

CCG AAT GGA TAT ATA ACA CAG TGT CCA AAT CTA AAT CAC ACT TGC CCA       786
Pro Asn Gly Tyr Ile Thr Gln Cys Pro Asn Leu Asn His Thr Cys Pro
        215                 220                 225

ACC TGC AGT GAT TTC TTA AGC CTG GTG CAA GGA ATA ATG GAT TTA CAA       834
Thr Cys Ser Asp Phe Leu Ser Leu Val Gln Gly Ile Met Asp Leu Gln
    230                 235                 240
```

-continued

GAG CTT TTG GCC AAG ATG ACT GCA AAA CTA AAT TAT GCA GAG ACA AGA 882
Glu Leu Leu Ala Lys Met Thr Ala Lys Leu Asn Tyr Ala Glu Thr Arg
245 250 255 260

CTT AGT CAA TTG GAA AAC TGT CAT TGT GAG AAG ACT TGT CAA GTG AGT 930
Leu Ser Gln Leu Glu Asn Cys His Cys Glu Lys Thr Cys Gln Val Ser
265 270 275

GGA CTG CTC TAT CGA GAT CAA GAC TCT TGG GTA GAT GGT GAC CAT TGC 978
Gly Leu Leu Tyr Arg Asp Gln Asp Ser Trp Val Asp Gly Asp His Cys
280 285 290

AGG AAC TGC ACT TGC AAA AGT GGT GCC GTG GAA TGC CGA AGG ATG TCC 1026
Arg Asn Cys Thr Cys Lys Ser Gly Ala Val Glu Cys Arg Arg Met Ser
295 300 305

TGT CCC CCT CTC AAT TGC TCC CCA GAC TCC CTC CCA GTA CAC ATT GCT 1074
Cys Pro Pro Leu Asn Cys Ser Pro Asp Ser Leu Pro Val His Ile Ala
310 315 320

GGC CAG TGC TGT AAG GTC TGC CGA CCA AAA TGT ATC TAT GGA GGA AAA 1122
Gly Gln Cys Cys Lys Val Cys Arg Pro Lys Cys Ile Tyr Gly Gly Lys
325 330 335 340

GTT CTT GCA GAA GGC CAG CGG ATT TTA ACC AAG AGC TGT CGG GAA TGC 1170
Val Leu Ala Glu Gly Gln Arg Ile Leu Thr Lys Ser Cys Arg Glu Cys
345 350 355

CGA GGT GGA GTT TTA GTA AAA ATT ACA GAA ATG TGT CCT CCT TTG AAC 1218
Arg Gly Gly Val Leu Val Lys Ile Thr Glu Met Cys Pro Pro Leu Asn
360 365 370

TGC TCA GAA AAG GAT CAC ATT CTT CCT GAG AAT CAG TGC TGC CGT GTC 1266
Cys Ser Glu Lys Asp His Ile Leu Pro Glu Asn Gln Cys Cys Arg Val
375 380 385

TGT AGA GGT CAT AAC TTT TGT GCA GAA GGA CCT AAA TGT GGT GAA AAC 1314
Cys Arg Gly His Asn Phe Cys Ala Glu Gly Pro Lys Cys Gly Glu Asn
390 395 400

TCA GAG TGC AAA AAC TGG AAT ACA AAA GCT ACT TGT GAG TGC AAG AGT 1362
Ser Glu Cys Lys Asn Trp Asn Thr Lys Ala Thr Cys Glu Cys Lys Ser
405 410 415 420

GGT TAC ATC TCT GTC CAG GGA GAC TCT GCC TAC TGT GAA GAT ATT GAT 1410
Gly Tyr Ile Ser Val Gln Gly Asp Ser Ala Tyr Cys Glu Asp Ile Asp
425 430 435

GAG TGT GCA GCT AAG ATG CAT TAC TGT CAT GCC AAT ACT GTG TGT GTC 1458
Glu Cys Ala Ala Lys Met His Tyr Cys His Ala Asn Thr Val Cys Val
440 445 450

AAC CTT CCT GGG TTA TAT CGC TGT GAC TGT GTC CCA GGA TAC ATT CGT 1506
Asn Leu Pro Gly Leu Tyr Arg Cys Asp Cys Val Pro Gly Tyr Ile Arg
455 460 465

GTG GAT GAC TTC TCT TGT ACA GAA CAC GAT GAA TGT GGC AGC GGC CAG 1554
Val Asp Asp Phe Ser Cys Thr Glu His Asp Glu Cys Gly Ser Gly Gln
470 475 480

CAC AAC TGT GAT GAG AAT GCC ATC TGC ACC AAC ACT GTC CAG GGA CAC 1602
His Asn Cys Asp Glu Asn Ala Ile Cys Thr Asn Thr Val Gln Gly His
485 490 495 500

AGC TGC ACC TGC AAA CCG GGC TAC GTG GGG AAC GGG ACC ATC TGC AGA 1650
Ser Cys Thr Cys Lys Pro Gly Tyr Val Gly Asn Gly Thr Ile Cys Arg
505 510 515

GCT TTC TGT GAA GAG GGC TGC AGA TAC GGT GGA ACG TGT GTG GCT CCC 1698
Ala Phe Cys Glu Glu Gly Cys Arg Tyr Gly Gly Thr Cys Val Ala Pro
520 525 530

AAC AAA TGT GTC TGT CCA TCT GGA TTC ACA GGA AGC CAC TGC GAG AAA 1746
Asn Lys Cys Val Cys Pro Ser Gly Phe Thr Gly Ser His Cys Glu Lys
535 540 545

GAT ATT GAT GAA TGT TCA GAG GGA ATC ATT GAG TGC CAC AAC CAT TCC 1794
Asp Ile Asp Glu Cys Ser Glu Gly Ile Ile Glu Cys His Asn His Ser
550 555 560

CGC TGC GTT AAC CTG CCA GGG TGG TAC CAC TGT GAG TGC AGA AGC GGT 1842
Arg Cys Val Asn Leu Pro Gly Trp Tyr His Cys Glu Cys Arg Ser Gly
565 570 575 580

TTC CAT GAC GAT GGG ACC TAT TCA CTG TCC GGG GAG TCC TGT ATT GAC 1890
Phe His Asp Asp Gly Thr Tyr Ser Leu Ser Gly Glu Ser Cys Ile Asp
585 590 595

ATT GAT GAA TGT GCC TTA AGA ACT CAC ACC TGT TGG AAC GAT TCT GCC 1938
Ile Asp Glu Cys Ala Leu Arg Thr His Thr Cys Trp Asn Asp Ser Ala
600 605 610

TGC ATC AAC CTG GCA GGG GGT TTT GAC TGT CTC TGC CCC TCT GGG CCC 1986
Cys Ile Asn Leu Ala Gly Gly Phe Asp Cys Leu Cys Pro Ser Gly Pro
615 620 625

TCC TGC TCT GGT GAC TGT CCT CAT GAA GGG GGG CTG AAG CAC AAT GGC 2034
Ser Cys Ser Gly Asp Cys Pro His Glu Gly Gly Leu Lys His Asn Gly
630 635 640

CAG GTG TGG ACC TTG AAA GAA GAC AGG TGT TCT GTC TGC TCC TGC AAG 2082
Gln Val Trp Thr Leu Lys Glu Asp Arg Cys Ser Val Cys Ser Cys Lys
645 650 655 660

GAT GGC AAG ATA TTC TGC CGA CGG ACA GCT TGT GAT TGC CAG AAT CCA 2130
Asp Gly Lys Ile Phe Cys Arg Arg Thr Ala Cys Asp Cys Gln Asn Pro
665 670 675

AGT GCT GAC CTA TTC TGT TGC CCA GAA TGT GAC ACC AGA GTC ACA AGT 2178
Ser Ala Asp Leu Phe Cys Cys Pro Glu Cys Asp Thr Arg Val Thr Ser
680 685 690

CAA TGT TTA GAC CAA AAT GGT CAC AAG CTG TAT CGA AGT GGA GAC AAT 2226
Gln Cys Leu Asp Gln Asn Gly His Lys Leu Tyr Arg Ser Gly Asp Asn
695 700 705

TGG ACC CAT AGC TGT CAG CAG TGT CGG TGT CTG GAA GGA GAG GTA GAT 2274
Trp Thr His Ser Cys Gln Gln Cys Arg Cys Leu Glu Gly Glu Val Asp
710 715 720

TGC TGG CCA CTC ACT TGC CCC AAC TTG AGC TGT GAG TAT ACA GCT ATC 2322
Cys Trp Pro Leu Thr Cys Pro Asn Leu Ser Cys Glu Tyr Thr Ala Ile
725 730 735 740

TTA GAA GGG GAA TGT TGT CCC CGC TGT GTC AGT GAC CCC TGC CTA GCT 2370
Leu Glu Gly Glu Cys Cys Pro Arg Cys Val Ser Asp Pro Cys Leu Ala
745 750 755

GAT AAC ATC ACC TAT GAC ATC AGA AAA ACT TGC CTG GAC AGC TAT GGT 2418
Asp Asn Ile Thr Tyr Asp Ile Arg Lys Thr Cys Leu Asp Ser Tyr Gly
760 765 770

GTT TCA CGG CTT AGT GGC TCA GTG TGG ACG ATG GCT GGA TCT CCC TGC 2466
Val Ser Arg Leu Ser Gly Ser Val Trp Thr Met Ala Gly Ser Pro Cys
775 780 785

ACA ACC TGT AAA TGC AAG AAT GGA AGA GTC TGT TGT TCT GTG GAT TTT 2514
Thr Thr Cys Lys Cys Lys Asn Gly Arg Val Cys Cys Ser Val Asp Phe
790 795 800

GAG TGT CTT CAA AAT AAT TGAAGTATTT ACAGTGGACT CAACGCAGAA 2562
Glu Cys Leu Gln Asn Asn
805 810

GAATGGACGA AATGACCATC CAACGTGATT AAGGATAGGA ATCGGTAGTT TGGTTTTTTT 2622

GTTTGTTTTG TTTTTTTAAC CACAGATAAT TGCCAAAGTT TCCACCTGAG GACGGTGTTT 2682

CGGAGGTTGC CTTTTGGACC TACCACTTTG CTCATTCTTG CTAACCTAGT CTAGGTGACC 2742

TACAGTGCCG TGCATTTAAG TCAATGGTTG TTAAAAGAAG TTTCCCGTGT TGTAAATCAT 2802

GTTTCCCTTA TCAGATCATT TGCAAATACA TTTAAATGAT CTCATGGTAA ATGGTTGATG 2862

TATTTTTTGG GTTTATTTTG TGTACTAACC ATAATAGAGA GAGACTCAGC TCCTTTTATT 2922

TATTTTGTTG ATTTATGGAT CAAATTCTAA AATAAAGTTG CCTGTTGTGA CTTTT 2977

( 2 ) INFORMATION FOR SEQ ID NO:37:

( i ) SEQUENCE CHARACTERISTICS:
( A ) LENGTH: 816 amino acids
( B ) TYPE: amino acid
( D ) TOPOLOGY: linear ( i i ) MOLECULE TYPE: protein ( x i ) SEQUENCE DESCRIPTION: SEQ ID NO:37:

Met Glu Ser Arg Val Leu Leu Arg Thr Phe Cys Leu Ile Phe Gly Leu
1 5 10 15

Gly Ala Val Trp Gly Leu Gly Val Asp Pro Ser Leu Gln Ile Asp Val
20 25 30

Leu Thr Glu Leu Glu Leu Gly Glu Ser Thr Thr Gly Val Arg Gln Val
35 40 45

Pro Gly Leu His Asn Gly Thr Lys Ala Phe Leu Phe Gln Asp Thr Pro
50 55 60

Arg Ser Ile Lys Ala Ser Thr Ala Thr Ala Glu Gln Phe Phe Gln Lys
65 70 75 80

Leu Arg Asn Lys His Glu Phe Thr Ile Leu Val Thr Leu Lys Gln Thr
85 90 95

His Leu Asn Ser Gly Val Ile Leu Ser Ile His His Leu Asp His Arg
100 105 110

Tyr Leu Glu Leu Glu Ser Ser Gly His Arg Asn Glu Val Arg Leu His
115 120 125

Tyr Arg Ser Gly Ser His Arg Pro His Thr Glu Val Phe Pro Tyr Ile
130 135 140

Leu Ala Asp Asp Lys Trp His Lys Leu Ser Leu Ala Ile Ser Ala Ser
145 150 155 160

His Leu Ile Leu His Ile Asp Cys Asn Lys Ile Tyr Glu Arg Val Val
165 170 175

Glu Lys Pro Ser Thr Asp Leu Pro Leu Gly Thr Thr Phe Trp Leu Gly
180 185 190

Gln Arg Asn Asn Ala His Gly Tyr Phe Lys Gly Ile Met Gln Asp Val
195 200 205

Gln Leu Leu Val Met Pro Gln Gly Phe Ile Ala Gln Cys Pro Asp Leu
210 215 220

Asn Arg Thr Cys Pro Thr Cys Asn Asp Phe His Gly Leu Val Gln Lys
225 230 235 240

Ile Met Glu Leu Gln Asp Ile Leu Ala Lys Thr Ser Ala Lys Leu Ser
245 250 255

Arg Ala Glu Gln Arg Met Asn Arg Leu Asp Gln Cys Tyr Cys Glu Arg
260 265 270

Thr Cys Thr Met Lys Gly Thr Thr Tyr Arg Glu Phe Glu Ser Trp Ile
275 280 285

Asp Gly Cys Lys Asn Cys Thr Cys Leu Asn Gly Thr Ile Gln Cys Glu
290 295 300

Thr Leu Ile Cys Pro Asn Pro Asp Cys Pro Leu Lys Ser Ala Leu Ala
305 310 315 320

Tyr Val Asp Gly Lys Cys Cys Lys Glu Cys Lys Ser Ile Cys Gln Phe
325 330 335

Gln Gly Arg Thr Tyr Phe Glu Gly Glu Arg Asn Thr Val Tyr Ser Ser
340 345 350

Ser Gly Val Cys Val Leu Tyr Glu Cys Lys Asp Gln Thr Met Lys Leu
355 360 365

-continued

| | | | | | | | | | | | | | | | |
|---|---|---|---|---|---|---|---|---|---|---|---|---|---|---|---|
| Val | Glu | Ser | Ser | Gly | Cys | Pro | Ala | Leu | Asp | Cys | Pro | Glu | Ser | His | Gln |
| | 370 | | | | | 375 | | | | | 380 | | | | |
| Ile | Thr | Leu | Ser | His | Ser | Cys | Cys | Lys | Val | Cys | Lys | Gly | Tyr | Asp | Phe |
| 385 | | | | | 390 | | | | | 395 | | | | | 400 |
| Cys | Ser | Glu | Arg | His | Asn | Cys | Met | Glu | Asn | Ser | Ile | Cys | Arg | Asn | Leu |
| | | | | 405 | | | | | 410 | | | | | 415 | |
| Asn | Asp | Arg | Ala | Val | Cys | Ser | Cys | Arg | Asp | Gly | Phe | Arg | Ala | Leu | Arg |
| | | | 420 | | | | | 425 | | | | | 430 | | |
| Glu | Asp | Asn | Ala | Tyr | Cys | Glu | Asp | Ile | Asp | Glu | Cys | Ala | Glu | Gly | Arg |
| | | 435 | | | | | 440 | | | | | 445 | | | |
| His | Tyr | Cys | Arg | Glu | Asn | Thr | Met | Cys | Val | Asn | Thr | Pro | Gly | Ser | Phe |
| | 450 | | | | | 455 | | | | | 460 | | | | |
| Met | Cys | Ile | Cys | Lys | Thr | Gly | Tyr | Ile | Arg | Ile | Asp | Asp | Tyr | Ser | Cys |
| 465 | | | | | 470 | | | | | 475 | | | | | 480 |
| Thr | Glu | His | Asp | Glu | Cys | Ile | Thr | Asn | Gln | His | Asn | Cys | Asp | Glu | Asn |
| | | | | 485 | | | | | 490 | | | | | 495 | |
| Ala | Leu | Cys | Phe | Asn | Thr | Val | Gly | Gly | His | Asn | Cys | Val | Cys | Lys | Pro |
| | | | 500 | | | | | 505 | | | | | 510 | | |
| Gly | Tyr | Thr | Gly | Asn | Gly | Thr | Thr | Cys | Lys | Ala | Phe | Cys | Lys | Asp | Gly |
| | | 515 | | | | | 520 | | | | | 525 | | | |
| Cys | Arg | Asn | Gly | Gly | Ala | Cys | Ile | Ala | Ala | Asn | Val | Cys | Ala | Cys | Pro |
| | 530 | | | | | 535 | | | | | 540 | | | | |
| Gln | Gly | Phe | Thr | Gly | Pro | Ser | Cys | Glu | Thr | Asp | Ile | Asp | Glu | Cys | Ser |
| 545 | | | | | 550 | | | | | 555 | | | | | 560 |
| Asp | Gly | Phe | Val | Gln | Cys | Asp | Ser | Arg | Ala | Asn | Cys | Ile | Asn | Leu | Pro |
| | | | | 565 | | | | | 570 | | | | | 575 | |
| Gly | Trp | Tyr | His | Cys | Glu | Cys | Arg | Asp | Gly | Tyr | His | Asp | Asn | Gly | Met |
| | | | 580 | | | | | 585 | | | | | 590 | | |
| Phe | Ser | Pro | Ser | Gly | Glu | Ser | Cys | Glu | Asp | Ile | Asp | Glu | Cys | Gly | Thr |
| | | 595 | | | | | 600 | | | | | 605 | | | |
| Gly | Arg | His | Ser | Cys | Ala | Asn | Asp | Thr | Ile | Cys | Phe | Asn | Leu | Asp | Gly |
| | 610 | | | | | 615 | | | | | 620 | | | | |
| Gly | Tyr | Asp | Cys | Arg | Cys | Pro | His | Gly | Lys | Asn | Cys | Thr | Gly | Asp | Cys |
| 625 | | | | | 630 | | | | | 635 | | | | | 640 |
| Ile | His | Asp | Gly | Lys | Val | Lys | His | Asn | Gly | Gln | Ile | Trp | Val | Leu | Glu |
| | | | | 645 | | | | | 650 | | | | | 655 | |
| Asn | Asp | Arg | Cys | Ser | Val | Cys | Ser | Cys | Gln | Asn | Gly | Phe | Val | Met | Cys |
| | | | 660 | | | | | 665 | | | | | 670 | | |
| Arg | Arg | Met | Val | Cys | Asp | Cys | Glu | Asn | Pro | Thr | Val | Asp | Leu | Phe | Cys |
| | | 675 | | | | | 680 | | | | | 685 | | | |
| Cys | Pro | Glu | Cys | Asp | Pro | Arg | Leu | Ser | Ser | Gln | Cys | Leu | His | Gln | Asn |
| | 690 | | | | | 695 | | | | | 700 | | | | |
| Gly | Glu | Thr | Leu | Tyr | Asn | Ser | Gly | Asp | Thr | Trp | Val | Gln | Asn | Cys | Gln |
| 705 | | | | | 710 | | | | | 715 | | | | | 720 |
| Gln | Cys | Arg | Cys | Leu | Gln | Gly | Glu | Val | Asp | Cys | Trp | Pro | Leu | Pro | Cys |
| | | | | 725 | | | | | 730 | | | | | 735 | |
| Pro | Asp | Val | Glu | Cys | Glu | Phe | Ser | Ile | Leu | Pro | Glu | Asn | Glu | Cys | Cys |
| | | | 740 | | | | | 745 | | | | | 750 | | |
| Pro | Arg | Cys | Val | Thr | Asp | Pro | Cys | Gln | Ala | Asp | Thr | Ile | Arg | Asn | Asp |
| | | 755 | | | | | 760 | | | | | 765 | | | |
| Ile | Thr | Lys | Thr | Cys | Leu | Asp | Glu | Met | Asn | Val | Val | Arg | Phe | Thr | Gly |
| | 770 | | | | | 775 | | | | | 780 | | | | |
| Ser | Ser | Trp | Ile | Lys | His | Gly | Thr | Glu | Cys | Thr | Leu | Cys | Gln | Cys | Lys |
| 785 | | | | | 790 | | | | | 795 | | | | | 800 |

Asn Gly His Ile Cys Cys Ser Val Asp Pro Gln Cys Leu Gln Glu Leu
805 810 815

(2) INFORMATION FOR SEQ ID NO:38:

(i) SEQUENCE CHARACTERISTICS:
(A) LENGTH: 2448 base pairs
(B) TYPE: nucleic acid
(C) STRANDEDNESS: single
(D) TOPOLOGY: linear (ii) MOLECULE TYPE: DNA(genomic)

(xi) SEQUENCE DESCRIPTION: SEQ ID NO:38:

```
ATGGAGTCTC GGGTCTTACT GAGAACATTC TGTTTGATCT TCGGTCTCGG AGCAGTTTGG    60
GGGCTTGGTG TGGACCCTTC CCTACAGATT GACGTCTTAA CAGAGTTAGA ACTTGGGGAG   120
TCCACGACCG GAGTGCGTCA GGTCCCGGGG CTGCATAATG GGACGAAAGC CTTTCTCTTT   180
CAAGATACTC CCAGAAGCAT AAAAGCATCC ACTGCTACAG CTGAACAGTT TTTTCAGAAG   240
CTGAGAAATA AACATGAATT TACTATTTTG GTGACCCTAA AACAGACCCA CTTAAATTCA   300
GGAGTTATTC TCTCAATTCA CCACTTGGAT CACAGGTACC TGGAACTGGA AAGTAGTGGC   360
CATCGGAATG AAGTCAGACT GCATTACCGC TCAGGCAGTC ACCGCCCTCA CACAGAAGTG   420
TTTCCTTACA TTTTGGCTGA TGACAAGTGG CACAAGCTCT CCTTAGCCAT CAGTGCTTCC   480
CATTTGATTT TACACATTGA CTGCAATAAA ATTTATGAAA GGGTAGTAGA AAAGCCCTCC   540
ACAGACTTGC CTCTAGGCAC AACATTTTGG CTAGGACAGA GAAATAATGC GCATGGATAT   600
TTTAAGGGTA TAATGCAAGA TGTCCAATTA CTTGTCATGC CCCAGGGATT TATTGCTCAG   660
TGCCCAGATC TTAATCGCAC CTGTCCAACT TGCAATGACT TCCATGGACT TGTGCAGAAA   720
ATCATGGAGC TACAGGATAT TTTAGCCAAA ACATCAGCCA AGCTGTCTCG AGCTGAACAG   780
CGAATGAATA GATTGGATCA GTGCTATTGT GAAAGGACTT GCACCATGAA GGGAACCACC   840
TACCGAGAAT TTGAGTCCTG GATAGACGGC TGTAAGAACT GCACATGCCT GAATGGAACC   900
ATCCAGTGTG AAACTCTAAT CTGCCCAAAT CCTGACTGCC CACTTAAGTC GGCTCTTGCG   960
TATGTGGATG GCAAATGCTG TAAGGAATGC AAATCGATAT GCCAATTTCA AGGACGAACC  1020
TACTTTGAAG GAGAAAGAAA TACAGTCTAT TCCTCTTCTG GAGTATGTGT TCTCTATGAG  1080
TGCAAGGACC AGACCATGAA ACTTGTTGAG AGTTCAGGCT GTCCAGCTTT GGATTGTCCA  1140
GAGTCTCATC AGATAACCTT GTCTCACAGC TGTTGCAAAG TTTGTAAAGG TTATGACTTT  1200
TGTTCTGAAA GGCATAACTG CATGGAGAAT TCCATCTGCA GAAATCTGAA TGACAGGGCT  1260
GTTTGTAGCT GTCGAGATGG TTTTAGGGCT CTTCGAGAGG ATAATGCCTA CTGTGAAGAC  1320
ATCGATGAGT GTGCTGAAGG GCGCCATTAC TGTCGTGAAA ATACAATGTG TGTCAACACC  1380
CCGGGTTCTT TTATGTGCAT CTGCAAAACT GGATACATCA GAATTGATGA TTATTCATGT  1440
ACAGAACATG ATGAGTGTAT CACAAATCAG CACAACTGTG ATGAAAATGC TTTATGCTTC  1500
AACACTGTTG GAGGACACAA CTGTGTTTGC AAGCCGGGCT ATACAGGGAA TGGAACGACA  1560
TGCAAAGCAT TTTGCAAAGA TGGCTGTAGG AATGGAGGAG CCTGTATTGC CGCTAATGTG  1620
TGTGCCTGCC CACAAGGCTT CACTGGACCC AGCTGTGAAA CGGACATTGA TGAATGCTCT  1680
GATGGTTTTG TTCAATGTGA CAGTCGTGCT AATTGCATTA ACCTGCCTGG ATGGTACCAC  1740
TGTGAGTGCA GAGATGGCTA CCATGACAAT GGGATGTTTT CACCAAGTGG AGAATCGTGT  1800
GAAGATATTG ATGAGTGTGG GACCGGGAGG CACAGCTGTG CCAATGATAC CATTTGCTTC  1860
AATTTGGATG GCGGATATGA TTGTCGATGT CCTCATGGAA AGAATTGCAC AGGGGACTGC  1920
```

-continued

```
ATCCATGATG GAAAAGTTAA GCACAATGGT CAGATTTGGG TGTTGGAAAA TGACAGGTGC 1980

TCTGTGTGCT CATGTCAGAA TGGATTCGTT ATGTGTCGAC GGATGGTCTG TGACTGTGAG 2040

AATCCCACAG TTGATCTTTT TTGCTGCCCT GAATGTGACC CAAGGCTTAG TAGTCAGTGC 2100

CTCCATCAAA ATGGGGAAAC TTTGTATAAC AGTGGTGACA CCTGGGTCCA GAATTGTCAA 2160

CAGTGCCGCT GCTTGCAAGG GGAAGTTGAT TGTTGGCCCC TGCCTTGCCC AGATGTGGAG 2220

TGTGAATTCA GCATTCTCCC AGAGAATGAG TGCTGCCCGC GCTGTGTCAC AGACCCTTGC 2280

CAGGCTGACA CCATCCGCAA TGACATCACC AAGACTTGCC TGGACGAAAT GAATGTGGTT 2340

CGCTTCACCG GGTCCTCTTG GATCAAACAT GGCACTGAGT GTACTCTCTG CCAGTGCAAG 2400

AATGGCCACA TCTGTTGCTC AGTGGATCCA CAGTGCCTTC AGGAACTG             2448
```

( 2 ) INFORMATION FOR SEQ ID NO:39:

( i ) SEQUENCE CHARACTERISTICS:
( A ) LENGTH: 3198 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-093E05

( i x ) FEATURE:
( A ) NAME/KEY: CDS
( B ) LOCATION: 97..2544

( x i ) SEQUENCE DESCRIPTION: SEQ ID NO:39:

```
TTGGGAGGAG CAGTCTCTCC GCTCGTCTCC CGGAGCTTTC TCCATTGTCT CTGCCTTTAC     60

AACAGAGGGA GACGATGGAC TGAGCTGATC CGCACC ATG GAG TCT CGG GTC TTA      114
                                        Met Glu Ser Arg Val Leu
                                          1               5

CTG AGA ACA TTC TGT TTG ATC TTC GGT CTC GGA GCA GTT TGG GGG CTT      162
Leu Arg Thr Phe Cys Leu Ile Phe Gly Leu Gly Ala Val Trp Gly Leu
             10                  15                  20

GGT GTG GAC CCT TCC CTA CAG ATT GAC GTC TTA ACA GAG TTA GAA CTT      210
Gly Val Asp Pro Ser Leu Gln Ile Asp Val Leu Thr Glu Leu Glu Leu
         25                  30                  35

GGG GAG TCC ACG ACC GGA GTG CGT CAG GTC CCG GGG CTG CAT AAT GGG      258
Gly Glu Ser Thr Thr Gly Val Arg Gln Val Pro Gly Leu His Asn Gly
     40                  45                  50

ACG AAA GCC TTT CTC TTT CAA GAT ACT CCC AGA AGC ATA AAA GCA TCC      306
Thr Lys Ala Phe Leu Phe Gln Asp Thr Pro Arg Ser Ile Lys Ala Ser
 55                  60                  65                  70

ACT GCT ACA GCT GAA CAG TTT TTT CAG AAG CTG AGA AAT AAA CAT GAA      354
Thr Ala Thr Ala Glu Gln Phe Phe Gln Lys Leu Arg Asn Lys His Glu
                 75                  80                  85

TTT ACT ATT TTG GTG ACC CTA AAA CAG ACC CAC TTA AAT TCA GGA GTT      402
Phe Thr Ile Leu Val Thr Leu Lys Gln Thr His Leu Asn Ser Gly Val
             90                  95                 100

ATT CTC TCA ATT CAC CAC TTG GAT CAC AGG TAC CTG GAA CTG GAA AGT      450
Ile Leu Ser Ile His His Leu Asp His Arg Tyr Leu Glu Leu Glu Ser
        105                 110                 115

AGT GGC CAT CGG AAT GAA GTC AGA CTG CAT TAC CGC TCA GGC AGT CAC      498
Ser Gly His Arg Asn Glu Val Arg Leu His Tyr Arg Ser Gly Ser His
```

-continued

```
    120                     125                     130

CGC CCT CAC ACA GAA GTG TTT CCT TAC ATT TTG GCT GAT GAC AAG TGG      546
Arg Pro His Thr Glu Val Phe Pro Tyr Ile Leu Ala Asp Asp Lys Trp
135                 140                 145                 150

CAC AAG CTC TCC TTA GCC ATC AGT GCT TCC CAT TTG ATT TTA CAC ATT      594
His Lys Leu Ser Leu Ala Ile Ser Ala Ser His Leu Ile Leu His Ile
                155                 160                 165

GAC TGC AAT AAA ATT TAT GAA AGG GTA GTA GAA AAG CCC TCC ACA GAC      642
Asp Cys Asn Lys Ile Tyr Glu Arg Val Val Glu Lys Pro Ser Thr Asp
            170                 175                 180

TTG CCT CTA GGC ACA ACA TTT TGG CTA GGA CAG AGA AAT AAT GCG CAT      690
Leu Pro Leu Gly Thr Thr Phe Trp Leu Gly Gln Arg Asn Asn Ala His
        185                 190                 195

GGA TAT TTT AAG GGT ATA ATG CAA GAT GTC CAA TTA CTT GTC ATG CCC      738
Gly Tyr Phe Lys Gly Ile Met Gln Asp Val Gln Leu Leu Val Met Pro
    200                 205                 210

CAG GGA TTT ATT GCT CAG TGC CCA GAT CTT AAT CGC ACC TGT CCA ACT      786
Gln Gly Phe Ile Ala Gln Cys Pro Asp Leu Asn Arg Thr Cys Pro Thr
215                 220                 225                 230

TGC AAT GAC TTC CAT GGA CTT GTG CAG AAA ATC ATG GAG CTA CAG GAT      834
Cys Asn Asp Phe His Gly Leu Val Gln Lys Ile Met Glu Leu Gln Asp
                235                 240                 245

ATT TTA GCC AAA ACA TCA GCC AAG CTG TCT CGA GCT GAA CAG CGA ATG      882
Ile Leu Ala Lys Thr Ser Ala Lys Leu Ser Arg Ala Glu Gln Arg Met
            250                 255                 260

AAT AGA TTG GAT CAG TGC TAT TGT GAA AGG ACT TGC ACC ATG AAG GGA      930
Asn Arg Leu Asp Gln Cys Tyr Cys Glu Arg Thr Cys Thr Met Lys Gly
        265                 270                 275

ACC ACC TAC CGA GAA TTT GAG TCC TGG ATA GAC GGC TGT AAG AAC TGC      978
Thr Thr Tyr Arg Glu Phe Glu Ser Trp Ile Asp Gly Cys Lys Asn Cys
    280                 285                 290

ACA TGC CTG AAT GGA ACC ATC CAG TGT GAA ACT CTA ATC TGC CCA AAT     1026
Thr Cys Leu Asn Gly Thr Ile Gln Cys Glu Thr Leu Ile Cys Pro Asn
295                 300                 305                 310

CCT GAC TGC CCA CTT AAG TCG GCT CTT GCG TAT GTG GAT GGC AAA TGC     1074
Pro Asp Cys Pro Leu Lys Ser Ala Leu Ala Tyr Val Asp Gly Lys Cys
                315                 320                 325

TGT AAG GAA TGC AAA TCG ATA TGC CAA TTT CAA GGA CGA ACC TAC TTT     1122
Cys Lys Glu Cys Lys Ser Ile Cys Gln Phe Gln Gly Arg Thr Tyr Phe
            330                 335                 340

GAA GGA GAA AGA AAT ACA GTC TAT TCC TCT TCT GGA GTA TGT GTT CTC     1170
Glu Gly Glu Arg Asn Thr Val Tyr Ser Ser Ser Gly Val Cys Val Leu
        345                 350                 355

TAT GAG TGC AAG GAC CAG ACC ATG AAA CTT GTT GAG AGT TCA GGC TGT     1218
Tyr Glu Cys Lys Asp Gln Thr Met Lys Leu Val Glu Ser Ser Gly Cys
    360                 365                 370

CCA GCT TTG GAT TGT CCA GAG TCT CAT CAG ATA ACC TTG TCT CAC AGC     1266
Pro Ala Leu Asp Cys Pro Glu Ser His Gln Ile Thr Leu Ser His Ser
375                 380                 385                 390

TGT TGC AAA GTT TGT AAA GGT TAT GAC TTT TGT TCT GAA AGG CAT AAC     1314
Cys Cys Lys Val Cys Lys Gly Tyr Asp Phe Cys Ser Glu Arg His Asn
                395                 400                 405

TGC ATG GAG AAT TCC ATC TGC AGA AAT CTG AAT GAC AGG GCT GTT TGT     1362
Cys Met Glu Asn Ser Ile Cys Arg Asn Leu Asn Asp Arg Ala Val Cys
            410                 415                 420

AGC TGT CGA GAT GGT TTT AGG GCT CTT CGA GAG GAT AAT GCC TAC TGT     1410
Ser Cys Arg Asp Gly Phe Arg Ala Leu Arg Glu Asp Asn Ala Tyr Cys
        425                 430                 435

GAA GAC ATC GAT GAG TGT GCT GAA GGG CGC CAT TAC TGT CGT GAA AAT     1458
Glu Asp Ile Asp Glu Cys Ala Glu Gly Arg His Tyr Cys Arg Glu Asn
```

-continued

```
    440                 445                 450

ACA ATG TGT GTC AAC ACC CCG GGT TCT TTT ATG TGC ATC TGC AAA ACT    1506
Thr Met Cys Val Asn Thr Pro Gly Ser Phe Met Cys Ile Cys Lys Thr
455                 460                 465                 470

GGA TAC ATC AGA ATT GAT GAT TAT TCA TGT ACA GAA CAT GAT GAG TGT    1554
Gly Tyr Ile Arg Ile Asp Asp Tyr Ser Cys Thr Glu His Asp Glu Cys
                475                 480                 485

ATC ACA AAT CAG CAC AAC TGT GAT GAA AAT GCT TTA TGC TTC AAC ACT    1602
Ile Thr Asn Gln His Asn Cys Asp Glu Asn Ala Leu Cys Phe Asn Thr
            490                 495                 500

GTT GGA GGA CAC AAC TGT GTT TGC AAG CCG GGC TAT ACA GGG AAT GGA    1650
Val Gly Gly His Asn Cys Val Cys Lys Pro Gly Tyr Thr Gly Asn Gly
        505                 510                 515

ACG ACA TGC AAA GCA TTT TGC AAA GAT GGC TGT AGG AAT GGA GGA GCC    1698
Thr Thr Cys Lys Ala Phe Cys Lys Asp Gly Cys Arg Asn Gly Gly Ala
    520                 525                 530

TGT ATT GCC GCT AAT GTG TGT GCC TGC CCA CAA GGC TTC ACT GGA CCC    1746
Cys Ile Ala Ala Asn Val Cys Ala Cys Pro Gln Gly Phe Thr Gly Pro
535                 540                 545                 550

AGC TGT GAA ACG GAC ATT GAT GAA TGC TCT GAT GGT TTT GTT CAA TGT    1794
Ser Cys Glu Thr Asp Ile Asp Glu Cys Ser Asp Gly Phe Val Gln Cys
                555                 560                 565

GAC AGT CGT GCT AAT TGC ATT AAC CTG CCT GGA TGG TAC CAC TGT GAG    1842
Asp Ser Arg Ala Asn Cys Ile Asn Leu Pro Gly Trp Tyr His Cys Glu
            570                 575                 580

TGC AGA GAT GGC TAC CAT GAC AAT GGG ATG TTT TCA CCA AGT GGA GAA    1890
Cys Arg Asp Gly Tyr His Asp Asn Gly Met Phe Ser Pro Ser Gly Glu
        585                 590                 595

TCG TGT GAA GAT ATT GAT GAG TGT GGG ACC GGG AGG CAC AGC TGT GCC    1938
Ser Cys Glu Asp Ile Asp Glu Cys Gly Thr Gly Arg His Ser Cys Ala
    600                 605                 610

AAT GAT ACC ATT TGC TTC AAT TTG GAT GGC GGA TAT GAT TGT CGA TGT    1986
Asn Asp Thr Ile Cys Phe Asn Leu Asp Gly Gly Tyr Asp Cys Arg Cys
615                 620                 625                 630

CCT CAT GGA AAG AAT TGC ACA GGG GAC TGC ATC CAT GAT GGA AAA GTT    2034
Pro His Gly Lys Asn Cys Thr Gly Asp Cys Ile His Asp Gly Lys Val
                635                 640                 645

AAG CAC AAT GGT CAG ATT TGG GTG TTG GAA AAT GAC AGG TGC TCT GTG    2082
Lys His Asn Gly Gln Ile Trp Val Leu Glu Asn Asp Arg Cys Ser Val
            650                 655                 660

TGC TCA TGT CAG AAT GGA TTC GTT ATG TGT CGA CGG ATG GTC TGT GAC    2130
Cys Ser Cys Gln Asn Gly Phe Val Met Cys Arg Arg Met Val Cys Asp
        665                 670                 675

TGT GAG AAT CCC ACA GTT GAT CTT TTT TGC TGC CCT GAA TGT GAC CCA    2178
Cys Glu Asn Pro Thr Val Asp Leu Phe Cys Cys Pro Glu Cys Asp Pro
    680                 685                 690

AGG CTT AGT AGT CAG TGC CTC CAT CAA AAT GGG GAA ACT TTG TAT AAC    2226
Arg Leu Ser Ser Gln Cys Leu His Gln Asn Gly Glu Thr Leu Tyr Asn
695                 700                 705                 710

AGT GGT GAC ACC TGG GTC CAG AAT TGT CAA CAG TGC CGC TGC TTG CAA    2274
Ser Gly Asp Thr Trp Val Gln Asn Cys Gln Gln Cys Arg Cys Leu Gln
                715                 720                 725

GGG GAA GTT GAT TGT TGG CCC CTG CCT TGC CCA GAT GTG GAG TGT GAA    2322
Gly Glu Val Asp Cys Trp Pro Leu Pro Cys Pro Asp Val Glu Cys Glu
            730                 735                 740

TTC AGC ATT CTC CCA GAG AAT GAG TGC TGC CCG CGC TGT GTC ACA GAC    2370
Phe Ser Ile Leu Pro Glu Asn Glu Cys Cys Pro Arg Cys Val Thr Asp
        745                 750                 755

CCT TGC CAG GCT GAC ACC ATC CGC AAT GAC ATC ACC AAG ACT TGC CTG    2418
Pro Cys Gln Ala Asp Thr Ile Arg Asn Asp Ile Thr Lys Thr Cys Leu
```

```
      760                       765                       770

GAC GAA ATG AAT GTG GTT CGC TTC ACC GGG TCC TCT TGG ATC AAA CAT        2466
Asp Glu Met Asn Val Val Arg Phe Thr Gly Ser Ser Trp Ile Lys His
775                     780                     785                 790

GGC ACT GAG TGT ACT CTC TGC CAG TGC AAG AAT GGC CAC ATC TGT TGC        2514
Gly Thr Glu Cys Thr Leu Cys Gln Cys Lys Asn Gly His Ile Cys Cys
                795                     800                     805

TCA GTG GAT CCA CAG TGC CTT CAG GAA CTG TGAAGTTAAC TGTCTCATGG          2564
Ser Val Asp Pro Gln Cys Leu Gln Glu Leu
            810                     815

GAGATTTCTG TTAAAAGAAT GTTCTTTCAT TAAAAGACCA AAAAGAAGTT AAAACTTAAA      2624

TTGGGTGATT TGTGGGCAGC TAAATGCAGC TTTGTTAATA GCTGAGTGAA CTTTCAATTA      2684

TGAAATTTGT GGAGCTTGAC AAAATCACAA AAGGAAAATT ACTGGGGCAA AATTAGACCT      2744

CAAGTCTGCC TCTACTGTGT CTCACATCAC CATGTAGAAG AATGGGCGTA CAGTATATAC      2804

CGTGACATCC TGAACCCTGG ATAGAAAGCC TGAGCCCATT GGATCTGTGA AAGCCTCTAG      2864

CTTCACTGGT GCAGAAAATT TTCCTCTAGA TCAGAATCTT CAGAATCAGT TAGGTTCCTC      2924

ACTGCAAGAA ATAAAATGTC AGGCAGTGAA TGAATTATAT TTTCAGAAGT AAAGCAAAGA      2984

AGCTATAACA TGTTATGTAC AGTACACTCT GAAAAGAAAT CTGAAACAAG TTATTGTAAT      3044

GATAAAAATA ATGCACAGGC ATGGTTACTT AATATTTTCT AACAGGAAAA GTCATCCCTA      3104

TTTCCTTGTT TTACTGCACT TAATATTATT TGGTTGAATT TGTTCAGTAT AAGCTCGTTC      3164

TTGTGCAAAA TTAAATAAAT ATTTCTCTTA CCTT                                  3198
```

( 2 ) INFORMATION FOR SEQ ID NO:40:

( i ) SEQUENCE CHARACTERISTICS:
( A ) LENGTH: 499 amino acids
( B ) TYPE: amino acid
( D ) TOPOLOGY: linear ( i i ) MOLECULE TYPE: protein ( x i ) SEQUENCE DESCRIPTION: SEQ ID NO:40:

```
Met Glu Leu Ser Glu Pro Val Val Glu Asn Gly Glu Val Glu Met Ala
  1               5                  10                  15

Leu Glu Glu Ser Trp Glu His Ser Lys Glu Val Ser Glu Ala Glu Pro
             20                  25                  30

Gly Gly Gly Ser Ser Gly Asp Ser Gly Pro Pro Glu Glu Ser Gly Gln
         35                  40                  45

Glu Met Met Glu Glu Lys Glu Glu Ile Arg Lys Ser Lys Ser Val Ile
     50                  55                  60

Val Pro Ser Gly Ala Pro Lys Lys Glu His Val Asn Val Val Phe Ile
 65                  70                  75                  80

Gly His Val Asp Ala Gly Lys Ser Thr Ile Gly Gly Gln Ile Met Phe
                 85                  90                  95

Leu Thr Gly Met Ala Asp Lys Arg Thr Leu Glu Lys Tyr Glu Arg Glu
            100                 105                 110

Ala Glu Glu Lys Asn Arg Glu Thr Trp Tyr Leu Ser Trp Ala Leu Asp
        115                 120                 125

Thr Asn Gln Glu Glu Arg Asp Lys Gly Lys Thr Val Glu Val Gly Arg
    130                 135                 140

Ala Tyr Phe Glu Thr Glu Arg Lys His Phe Thr Ile Leu Asp Ala Pro
145                 150                 155                 160

Gly His Lys Ser Phe Val Pro Asn Met Ile Gly Gly Ala Ser Gln Ala
                165                 170                 175
```

-continued

Asp Leu Ala Val Leu Val Ile Ser Ala Arg Lys Gly Glu Phe Glu Thr
180 185 190

Gly Phe Glu Lys Gly Gly Gln Thr Arg Glu His Ala Met Phe Gly Lys
195 200 205

Thr Ala Gly Val Lys His Leu Ile Val Leu Ile Asn Lys Met Asp Asp
210 215 220

Pro Thr Val Asn Trp Gly Ile Glu Arg Tyr Glu Glu Cys Lys Glu Lys
225 230 235 240

Leu Val Pro Phe Leu Lys Lys Val Gly Phe Ser Pro Lys Lys Asp Ile
245 250 255

His Phe Met Pro Cys Ser Gly Leu Thr Gly Ala Asn Ile Lys Glu Gln
260 265 270

Ser Asp Phe Cys Pro Trp Tyr Thr Gly Leu Pro Phe Ile Pro Tyr Leu
275 280 285

Asn Asn Leu Pro Asn Phe Asn Arg Ser Ile Asp Gly Pro Ile Arg Leu
290 295 300

Pro Ile Val Asp Lys Tyr Lys Asp Met Gly Thr Val Val Leu Gly Lys
305 310 315 320

Leu Glu Ser Gly Ser Ile Phe Lys Gly Gln Gln Leu Val Met Met Pro
325 330 335

Asn Lys His Asn Val Glu Val Leu Gly Ile Leu Ser Asp Asp Thr Glu
340 345 350

Thr Asp Phe Val Ala Pro Gly Glu Asn Leu Lys Ile Arg Leu Lys Gly
355 360 365

Ile Glu Glu Glu Glu Ile Leu Pro Glu Phe Ile Leu Cys Asp Pro Ser
370 375 380

Asn Leu Cys His Ser Gly Arg Thr Phe Asp Val Gln Ile Val Ile Ile
385 390 395 400

Glu His Lys Ser Ile Ile Cys Pro Gly Tyr Asn Ala Val Leu His Ile
405 410 415

His Thr Cys Ile Glu Glu Val Glu Ile Thr Ala Leu Ile Ser Leu Val
420 425 430

Asp Lys Lys Ser Gly Glu Lys Ser Lys Thr Arg Pro Arg Phe Val Lys
435 440 445

Gln Asp Gln Val Cys Ile Ala Arg Leu Arg Thr Ala Gly Thr Ile Cys
450 455 460

Leu Glu Thr Phe Lys Asp Phe Pro Gln Met Gly Arg Phe Thr Leu Arg
465 470 475 480

Asp Glu Gly Lys Thr Ile Ala Ile Gly Lys Val Leu Lys Leu Val Pro
485 490 495

Glu Lys Asp ( 2 ) INFORMATION FOR SEQ ID NO:41:

( i ) SEQUENCE CHARACTERISTICS:
( A ) LENGTH: 1497 base pairs
( B ) TYPE: nucleic acid
( C ) STRANDEDNESS: single
( D ) TOPOLOGY: linear ( i i ) MOLECULE TYPE: DNA(genomic)

( x i ) SEQUENCE DESCRIPTION: SEQ ID NO:41:

ATGGAACTTT CAGAACCTGT TGTAGAAAAT GGAGAGGTGG AAATGGCCCT AGAAGAATCA 60

TGGGAGCACA GTAAAGAAGT AAGTGAAGCC GAGCCTGGGG GTGGTTCCTC GGGAGATTCA 120

-continued

GGGCCCCCAG AAGAAAGTGG CCAGGAAATG ATGGAGGAAA AAGAGGAAAT AAGAAAATCC 180

AAATCTGTGA TCGTACCCTC AGGTGCACCT AAGAAAGAAC ACGTAAATGT AGTATTCATT 240

GGCCATGTAG ACGCTGGCAA GTCAACCATC GGAGGACAGA TAATGTTTTT GACTGGAATG 300

GCTGACAAAA GAACACTGGA GAAATATGAA AGAGAAGCTG AGGAAAAAAA CAGAGAAACC 360

TGGTATTTGT CCTGGGCCTT AGATACAAAT CAGGAGGAAC GAGACAAGGG TAAAACAGTC 420

GAAGTGGGTC GTGCCTATTT TGAAACAGAA AGGAAACATT TCACAATTTT AGATGCCCCT 480

GGCCACAAGA GTTTTGTCCC AAATATGATT GGTGGTGCTT CTCAAGCTGA TTTGGCTGTG 540

CTGGTCATCT CTGCCAGGAA AGGAGAGTTT GAAACTGGAT TTGAAAAAGG TGGACAGACA 600

AGAGAACATG CGATGTTTGG CAAAACGGCA GGAGTAAAAC ATTTAATAGT GCTTATTAAT 660

AAGATGGATG ATCCCACAGT AAATTGGGGC ATCGAGAGAT ATGAAGAATG TAAAGAAAAA 720

CTGGTGCCCT TTTTGAAAAA AGTAGGCTTT AGTCCAAAAA AGGACATTCA CTTTATGCCC 780

TGCTCAGGAC TGACCGGAGC AAATATTAAA GAGCAGTCAG ATTTCTGCCC TTGGTACACT 840

GGATTACCAT TTATTCCGTA TTTGAATAAC TTGCCAAACT TCAACAGATC AATTGATGGA 900

CCAATAAGAC TGCCAATTGT GGATAAGTAC AAAGATATGG GCACTGTGGT CCTGGGAAAG 960

CTGGAATCCG GGTCCATTTT TAAAGGCCAG CAGCTCGTGA TGATGCCAAA CAAGCACAAT 1020

GTAGAAGTTC TTGGAATACT TTCTGATGAT ACTGAAACTG ATTTTGTAGC CCCAGGTGAA 1080

AACCTCAAAA TCAGACTGAA GGGAATTGAA GAAGAAGAGA TTCTTCCAGA ATTCATACTT 1140

TGTGATCCTA GTAACCTCTG CCATTCTGGA CGCACGTTTG ATGTTCAGAT AGTGATTATT 1200

GAGCACAAAT CCATCATCTG CCCAGGTTAT AATGCGGTGC TGCACATTCA TACTTGTATT 1260

GAGGAAGTTG AGATAACAGC GTTAATCTCC TTGGTAGACA AAAAATCAGG GGAAAAAAGT 1320

AAGACACGAC CCCGCTTCGT GAAACAAGAT CAAGTATGCA TTGCTCGTTT AAGGACAGCA 1380

GGAACCATCT GCCTCGAGAC GTTCAAAGAT TTTCCTCAGA TGGGTCGTTT TACTTTAAGA 1440

GATGAGGGTA AGACCATTGC AATTGGAAAA GTTCTGAAAT TGGTCCCAGA GAAGGAC 1497

( 2 ) INFORMATION FOR SEQ ID NO:42:

( i ) SEQUENCE CHARACTERISTICS:
( A ) LENGTH: 2057 base pairs
( B ) TYPE: nucleic acid
( C ) STRANDEDNESS: single
( D ) TOPOLOGY: linear ( i i ) MOLECULE TYPE: DNA(genomic)

( i i i ) HYPOTHETICAL: NO ( i v ) ANTI-SENSE: NO ( v i i ) IMMEDIATE SOURCE:
( A ) LIBRARY: Human fetal brain cDNA library
( B ) CLONE: GEN-077A09

( i x ) FEATURE:
( A ) NAME/KEY: CDS
( B ) LOCATION: 144..1640

( x i ) SEQUENCE DESCRIPTION: SEQ ID NO:42:

TCCCGGCCGG CTCCGGCAGC AACGATGAAG CCTGCACCGG CGCGGGATAC CCTCAAGGTA 60

AAAGGATGGG ACGGGGGGCA CCTGTGGAAC CTTCCCGAGA GGAACCGTTA GTGTCGCTTG 120

AAGGTTCCAA TTCAGCCGTT ACC ATG GAA CTT TCA GAA CCT GTT GTA GAA 170
Met Glu Leu Ser Glu Pro Val Val Glu
1 5

AAT GGA GAG GTG GAA ATG GCC CTA GAA GAA TCA TGG GAG CAC AGT AAA 218

-continued

```
Asn Gly Glu Val Glu Met Ala Leu Glu Glu Ser Trp Glu His Ser Lys
 10                  15                  20                  25

GAA GTA AGT GAA GCC GAG CCT GGG GGT GGT TCC TCG GGA GAT TCA GGG      266
Glu Val Ser Glu Ala Glu Pro Gly Gly Gly Ser Ser Gly Asp Ser Gly
                 30                  35                  40

CCC CCA GAA GAA AGT GGC CAG GAA ATG ATG GAG GAA AAA GAG GAA ATA      314
Pro Pro Glu Glu Ser Gly Gln Glu Met Met Glu Glu Lys Glu Glu Ile
             45                  50                  55

AGA AAA TCC AAA TCT GTG ATC GTA CCC TCA GGT GCA CCT AAG AAA GAA      362
Arg Lys Ser Lys Ser Val Ile Val Pro Ser Gly Ala Pro Lys Lys Glu
         60                  65                  70

CAC GTA AAT GTA GTA TTC ATT GGC CAT GTA GAC GCT GGC AAG TCA ACC      410
His Val Asn Val Val Phe Ile Gly His Val Asp Ala Gly Lys Ser Thr
     75                  80                  85

ATC GGA GGA CAG ATA ATG TTT TTG ACT GGA ATG GCT GAC AAA AGA ACA      458
Ile Gly Gly Gln Ile Met Phe Leu Thr Gly Met Ala Asp Lys Arg Thr
 90                  95                 100                 105

CTG GAG AAA TAT GAA AGA GAA GCT GAG GAA AAA AAC AGA GAA ACC TGG      506
Leu Glu Lys Tyr Glu Arg Glu Ala Glu Glu Lys Asn Arg Glu Thr Trp
                110                 115                 120

TAT TTG TCC TGG GCC TTA GAT ACA AAT CAG GAG GAA CGA GAC AAG GGT      554
Tyr Leu Ser Trp Ala Leu Asp Thr Asn Gln Glu Glu Arg Asp Lys Gly
            125                 130                 135

AAA ACA GTC GAA GTG GGT CGT GCC TAT TTT GAA ACA GAA AGG AAA CAT      602
Lys Thr Val Glu Val Gly Arg Ala Tyr Phe Glu Thr Glu Arg Lys His
        140                 145                 150

TTC ACA ATT TTA GAT GCC CCT GGC CAC AAG AGT TTT GTC CCA AAT ATG      650
Phe Thr Ile Leu Asp Ala Pro Gly His Lys Ser Phe Val Pro Asn Met
    155                 160                 165

ATT GGT GGT GCT TCT CAA GCT GAT TTG GCT GTG CTG GTC ATC TCT GCC      698
Ile Gly Gly Ala Ser Gln Ala Asp Leu Ala Val Leu Val Ile Ser Ala
170                 175                 180                 185

AGG AAA GGA GAG TTT GAA ACT GGA TTT GAA AAA GGT GGA CAG ACA AGA      746
Arg Lys Gly Glu Phe Glu Thr Gly Phe Glu Lys Gly Gly Gln Thr Arg
                190                 195                 200

GAA CAT GCG ATG TTT GGC AAA ACG GCA GGA GTA AAA CAT TTA ATA GTG      794
Glu His Ala Met Phe Gly Lys Thr Ala Gly Val Lys His Leu Ile Val
            205                 210                 215

CTT ATT AAT AAG ATG GAT GAT CCC ACA GTA AAT TGG GGC ATC GAG AGA      842
Leu Ile Asn Lys Met Asp Asp Pro Thr Val Asn Trp Gly Ile Glu Arg
        220                 225                 230

TAT GAA GAA TGT AAA GAA AAA CTG GTG CCC TTT TTG AAA AAA GTA GGC      890
Tyr Glu Glu Cys Lys Glu Lys Leu Val Pro Phe Leu Lys Lys Val Gly
    235                 240                 245

TTT AGT CCA AAA AAG GAC ATT CAC TTT ATG CCC TGC TCA GGA CTG ACC      938
Phe Ser Pro Lys Lys Asp Ile His Phe Met Pro Cys Ser Gly Leu Thr
250                 255                 260                 265

GGA GCA AAT ATT AAA GAG CAG TCA GAT TTC TGC CCT TGG TAC ACT GGA      986
Gly Ala Asn Ile Lys Glu Gln Ser Asp Phe Cys Pro Trp Tyr Thr Gly
                270                 275                 280

TTA CCA TTT ATT CCG TAT TTG AAT AAC TTG CCA AAC TTC AAC AGA TCA     1034
Leu Pro Phe Ile Pro Tyr Leu Asn Asn Leu Pro Asn Phe Asn Arg Ser
            285                 290                 295

ATT GAT GGA CCA ATA AGA CTG CCA ATT GTG GAT AAG TAC AAA GAT ATG     1082
Ile Asp Gly Pro Ile Arg Leu Pro Ile Val Asp Lys Tyr Lys Asp Met
        300                 305                 310

GGC ACT GTG GTC CTG GGA AAG CTG GAA TCC GGG TCC ATT TTT AAA GGC     1130
Gly Thr Val Val Leu Gly Lys Leu Glu Ser Gly Ser Ile Phe Lys Gly
    315                 320                 325

CAG CAG CTC GTG ATG ATG CCA AAC AAG CAC AAT GTA GAA GTT CTT GGA     1178
```

-continued

```
Gln Gln Leu Val Met Met Pro Asn Lys His Asn Val Glu Val Leu Gly
330                 335                 340                 345

ATA CTT TCT GAT GAT ACT GAA ACT GAT TTT GTA GCC CCA GGT GAA AAC     1226
Ile Leu Ser Asp Asp Thr Glu Thr Asp Phe Val Ala Pro Gly Glu Asn
                350                 355                 360

CTC AAA ATC AGA CTG AAG GGA ATT GAA GAA GAA GAG ATT CTT CCA GAA     1274
Leu Lys Ile Arg Leu Lys Gly Ile Glu Glu Glu Glu Ile Leu Pro Glu
            365                 370                 375

TTC ATA CTT TGT GAT CCT AGT AAC CTC TGC CAT TCT GGA CGC ACG TTT     1322
Phe Ile Leu Cys Asp Pro Ser Asn Leu Cys His Ser Gly Arg Thr Phe
        380                 385                 390

GAT GTT CAG ATA GTG ATT ATT GAG CAC AAA TCC ATC ATC TGC CCA GGT     1370
Asp Val Gln Ile Val Ile Ile Glu His Lys Ser Ile Ile Cys Pro Gly
    395                 400                 405

TAT AAT GCG GTG CTG CAC ATT CAT ACT TGT ATT GAG GAA GTT GAG ATA     1418
Tyr Asn Ala Val Leu His Ile His Thr Cys Ile Glu Glu Val Glu Ile
410                 415                 420                 425

ACA GCG TTA ATC TCC TTG GTA GAC AAA AAA TCA GGG GAA AAA AGT AAG     1466
Thr Ala Leu Ile Ser Leu Val Asp Lys Lys Ser Gly Glu Lys Ser Lys
                430                 435                 440

ACA CGA CCC CGC TTC GTG AAA CAA GAT CAA GTA TGC ATT GCT CGT TTA     1514
Thr Arg Pro Arg Phe Val Lys Gln Asp Gln Val Cys Ile Ala Arg Leu
            445                 450                 455

AGG ACA GCA GGA ACC ATC TGC CTC GAG ACG TTC AAA GAT TTT CCT CAG     1562
Arg Thr Ala Gly Thr Ile Cys Leu Glu Thr Phe Lys Asp Phe Pro Gln
        460                 465                 470

ATG GGT CGT TTT ACT TTA AGA GAT GAG GGT AAG ACC ATT GCA ATT GGA     1610
Met Gly Arg Phe Thr Leu Arg Asp Glu Gly Lys Thr Ile Ala Ile Gly
    475                 480                 485

AAA GTT CTG AAA TTG GTC CCA GAG AAG GAC TAAGCAATTT TCTTGATGCC       1660
Lys Val Leu Lys Leu Val Pro Glu Lys Asp
490                 495

TCTGCAAGAT ACTGTGAGGA GAATTGACAG CAAAAGTTCA CCACCTACTC TTATTTACTG   1720

CCCATTGATT GACTTTTCTT CATATTTTGC AAAGAGAAAT TTCACAGCAA AAATTCATGT   1780

TTTGTCAGCT TTCTCATGTT GAGATCTGTT ATGTCACTGA TGAATTTACC CTCAAGTTTC   1840

CTTCCTCTGT ACCACTCTGC TTCCTTGGAC AATATCAGTA ATAGCTTTGT AAGTGATGTG   1900

GACGTAATTG CCTACAGTAA TAAAAAAATA ATGTACTTTA ATTTTTCATT TTCTTTTAGG   1960

ATATTTAGAC CACCCTTGTT CCACGCAAAC CAGAGTGTGT CAGTGTTTGT GTGTGTGTTA   2020

AAATGATAAC TAACATGTGA ATAAAATACT CCATTTG                            2057
```

HUMAN GDP DISSOCIATION STIMULATING PROTEIN GENE

TECHNICAL FIELD

The present invention relates to a gene useful as an indicator in the prophylaxis, diagnosis and treatment of diseases in humans. More particularly, it relates to a novel human gene analogous to rat, mouse, yeast, nematode and known human genes, among others, and utilizable, after cDNA analysis thereof, chromosome mapping of cDNA and function analysis of cDNA, in gene diagnosis using said gene and in developing a novel therapeutic method.

BACKGROUND ART

The genetic information of a living thing has been accumulated as sequences (DNA) of four bases, namely A, C, G and T, which exist in cell nuclei. Said genetic information has been preserved for line preservation and ontogeny of each individual living thing.

In the case of human being, the number of said bases is said to be about 3 billion ($3\times10^9$) and supposedly there are 50 to 100 thousand genes therein. Such genetic information serves to maintain biological phenomena in that regulatory proteins, structural proteins and enzymes are produced via such route that mRNA is transcribed from a gene (DNA) and then translated into a protein. Abnormalities in said route from gene to protein translation are considered to be causative of abnormalities of life supporting systems, for example in cell proliferation and differentiation, hence causative of various diseases.

As a result of gene analyses so far made, a number of genes which may be expected to serve as useful materials in drug development, have been found, for example genes for various receptors such as insulin receptor and LDL receptor, genes involved in cell proliferation and differentiation and genes for metabolic enzymes such as proteases, ATPase and superoxide dismutases.

However, analysis of human genes and studies of the functions of the genes analyzed and of the relations between the genes analyzed and various diseases have been just begun and many points remain unknown. Further analysis of novel genes, analysis of the functions thereof, studies of the relations between the genes analyzed and diseases, and studies for applying the genes analyzed to gene diagnosis or for medicinal purposes, for instance, are therefore desired in the relevant art.

If such a novel human gene as mentioned above can be provided, it will be possible to analyze the level of expression thereof in each cell and the structure and function thereof and, through expression product analysis and other studies, it may become possible to reveal the pathogenesis of a disease associated therewith, for example a genopathy or cancer, or diagnose and treat said disease, for instance. It is an object of the present invention to provide such a novel human gene.

For attaining the above object, the present inventors made intensive investigations and obtained the findings mentioned below. Based thereon, the present invention has now been completed.

DISCLOSURE OF INVENTION

Thus, the present inventors synthesized cDNAs based on mRNAs extracted from various tissues, inclusive of human fetal brain, adult blood vessels and placenta, constructed libraries by inserting them into vectors, allowing colonies of *Escherichia coli* transformed with said libraries to form on agar medium, picked up colonies at random and transferred to 96-well micro plates and registered a large number of human gene-containing *E. coli* clones.

Each clone thus registered was cultivated on a small size, DNA was extracted and purified, the four base-specifically terminating extension reactions were carried out by the dideoxy chain terminator method using the cDNA extracted as a template, and the base sequence of the gene was determined over about 400 bases from the 5' terminus thereof using an automatic DNA sequencer. Based on the thus-obtained base sequence information, a novel family gene analogous to known genes of animal and plant species such as bacteria, yeasts, nematodes, mice and humans was searched for.

The method of the above-mentioned cDNA analysis is detailedly described in the literature by Fujiwara, one of the present inventors [Fujiwara, Tsutomu, Saibo Kogaku (Cell Engineering), 14, 645–654 (1995)].

Among this group, there are novel receptors, DNA binding domain-containing transcription regulating factors, signal transmission system factors, metabolic enzymes and so forth. Based on the homology of the novel gene of the present invention as obtained by gene analysis to the genes analogous thereto, the product of the gene, hence the function of the protein, can approximately be estimated by analogy. Furthermore, such functions as enzyme activity and binding ability can be investigated by inserting the candidate gene into an expression vector to give a recombinant.

According to the present invention, there are provided a novel human gene characterized by containing a nucleotide sequence coding for an amino acid sequence defined by SEQ ID NO:1, :4, :7, :10, :13, :16, :19, :22, :25, :28, :31, :34, :37 or 40, a human gene characterized by containing the nucleotide sequence defined by SEQ ID NO:2, :5, :8, :11, :14, :17, :20, :23, :26, :29, :32, :35, :38 or :41, respectively coding for the amino acid sequence mentioned above, and a novel human gene characterized by the nucleotide sequence defined by SEQ ID NO:3, :6, :9, :12, :15, :18, :21, :24, :27, :30, :33, :36, :39 or :42.

The symbols used herein for indicating amino acids, peptides, nucleotides, nucleotide sequences and so on are those recommended by IUPAC and IUB or in "Guideline for drafting specifications etc. including nucleotide sequences or amino acid sequences" (edited by the Japanese Patent Office), or those in conventional use in the relevant field of art.

As specific examples of such gene of the present invention, there may be mentioned genes deducible from the DNA sequences of the clones designated as "GEN-501D08", "GEN-080G01", "GEN-025F07", "GEN-076C09", "GEN-331G07", "GEN-163D09", "GEN-078D05TA13", "GEN-423A12", "GEN-092E10", "GEN-428B12", "GEN-073E07", "GEN-093E05" and "GEN-077A09" shown later herein in Examples 1 to 11. The respective nucleotide sequences are as shown in the sequence listing.

These clones have an open reading frame comprising nucleotides (nucleic acid) respectively coding for the amino acids shown in the sequence listing. Their molecular weights were calculated at the values shown later herein in the respective examples. Hereinafter, these human genes of the present invention are sometimes referred to as the designation used in Examples 1 to 11.

In the following, the human gene of the present invention is described in further detail.

As mentioned above, each human gene of the present invention is analogous to rat, mouse, yeast, nematode and known human genes, among others, and can be utilized in human gene analysis based on the information about the genes analogous thereto and in studying the function of the gene analyzed and the relation between the gene analyzed and a disease. It is possible to use said gene in gene diagnosis of the disease associated therewith and in exploitation studies of said gene for medicinal purposes.

The gene of the present invention is represented in terms of a single-stranded DNA sequence, as shown under SEQ ID NO:2. It is to be noted, however, that the present invention also includes a DNA sequence complementary to such a single-stranded DNA sequence and a component comprising both. The sequence of the gene of the present invention as shown under SEQ ID NO:3n -1 (where n is an integer of 1 to 14) is merely an example of the codon combination encoding the respective amino acid residues. The gene of the present invention is not limited thereto but can of course have a DNA sequence in which the codons are arbitrarily selected and combined for the respective amino acid residues. The codon selection can be made in the conventional manner, for example taking into consideration the codon utilization frequencies in the host to be used [Nucl. Acids Res., 9, 43–74 (1981)].

The gene of the present invention further includes DNA sequences coding for functional equivalents derived from the amino acid sequence mentioned above by partial amino acid or amino acid sequence substitution, deletion or addition. These polypeptides may be produced by spontaneous modification (mutation) or may be obtained by posttranslational modification or by modifying the natural gene (of the present invention) by a technique of genetic engineering, for example by site-specific mutagenesis [Methods in Enzymology, 154, p. 350, 367–382 (1987); ibid., 100, p. 468 (1983); Nucleic Acids Research, 12, p. 9441 (1984); Zoku Seikagaku Jikken Koza (Sequel to Experiments in Biochemistry) 1, "Idensi Kenkyu-ho (Methods in Gene Research) II", edited by the Japan Biochemical Society, p. 105 (1986)] or synthesizing mutant DNAs by a chemical synthetic technique such as the phosphotriester method or phosphoamidite method [J. Am. Chem. Soc., 89, p. 4801 (1967); ibid., 91, p. 3350 (1969); Science, 150, p. 178 (1968); Tetrahedron Lett., 22, p. 1859 (1981); ibid., 24, p. 245 (1983)], or by utilizing the techniques mentioned above in combination.

The protein encoded by the gene of the present invention can be expressed readily and stably by utilizing said gene, for example inserting it into a vector for use with a microorganism and cultivating the microorganism thus transformed.

The protein obtained by utilizing the gene of the present invention can be used in specific antibody production. In this case, the protein producible in large quantities by the genetic engineering technique mentioned above can be used as the component to serve as an antigen. The antibody obtained may be polyclonal or monoclonal and can be advantageously used in the purification, assay, discrimination or identification of the corresponding protein.

The gene of the present invention can be readily produced based on the sequence information thereof disclosed herein by using general genetic engineering techniques [cf. e.g. Molecular Cloning, 2nd Ed., Cold Spring Harbor Laboratory Press (1989); Zoku Seikagaku Jikken Koza, "Idenshi Kenkyu-ho I, II and III", edited by the Japan Biochemical Society (1986)].

This can be achieved, for example, by selecting a desired clone from a human cDNA library (prepared in the conventional manner from appropriate cells of origin in which the gene is expressed) using a probe or antibody specific to the gene of the present invention [e.g. Proc. Natl. Acad. Sci. USA, 78, 6613 (1981); Science, 222, 778 (1983)].

The cells of origin to be used in the above method are, for example, cells or tissues in which the gene in question is expressed, or cultured cells derived therefrom. Separation of total RNA, separation and purification of mRNA, conversion to (synthesis of) cDNA, cloning thereof and so on can be carried out by conventional methods. cDNA libraries are also commercially available and such cDNA libraries, for example various cDNA libraries available from Clontech Lab. Inc. can also be used in the above method.

Screening of the gene of the present invention from these cDNA libraries can be carried out by the conventional method mentioned above. These screening methods include, for example, the method comprising selecting a cDNA clone by immunological screening using an antibody specific to the protein produced by the corresponding cDNA, the technique of plaque or colony hybridization using probes selectively binding to the desired DNA sequence, or a combination of these. As regards the probe to be used here, a DNA sequence chemically synthesized based on the information about the DNA sequence of the present invention is generally used. It is of course possible to use the gene of the present invention or fragments thereof as the proble.

Furthermore, a sense primer and an antisense primer designed based on the information about the partial amino acid sequence of a natural extract isolated and purified from cells or a tissue can be used as probes for screening.

For obtaining the gene of the present invention, the technique of DNA/RNA amplification by the PCR method [Science, 230, 1350–1354 (1984)] can suitably be employed. Particularly when the full-length cDNA can hardly be obtained from the library, the RACE method (rapid amplification of cDNA ends; Jikken Igaku (Experimental Medicine), 12 (6), 35–38 (1994)], in particular the 5'RACE method [Frohman, M. A., et al., Proc. Natl. Acad. Sci. USA, 85, 8998–9002 (1988)] is preferably employed. The primers to be used in such PCR method can be appropriately designed based on the sequence information of the gene of the present invention as disclosed herein and can be synthesized by a conventional method.

The amplified DNA/RNA fragment can be isolated and purified by a conventional method as mentioned above, for example by gel electrophoresis.

The nucleotide sequence of the thus-obtained gene of the present invention or any of various DNA fragments can be determined by a conventional method, for example the dideoxy method [Proc. Natl. Acad. Sci. USA, 74, 5463–5467 (1977)] or the Maxam-Gilbert method [Methods in Enzymology, 65, 499 (1980)]. Such nucleotide sequence determination can be readily performed using a commercially available sequence kit as well.

When the gene of the present invention is used and conventional techniques of recombinant DNA technology [see e.g. Science, 224, p. 1431 (1984); Biochem. Biophys. Res. Comm., 130, p. 692 (1985); Proc. Natl. Acad. Sci. USA, 80, p. 5990 (1983) and the references cited above] are followed, a recombinant protein can be obtained. More detailedly, said protein can be produced by constructing a recombinant DNA enabling the gene of the present invention to be expressed in host cells, introducing it into host cells for transformation thereof and cultivating the resulting transformant.

In that case, the host cells may be eukaryotic or prokaryotic. The eukaryotic cells include vertebrate cells, yeast cells and so on, and the vertebrate cells include, but are not limited to, simian cells named COS cells [Cell, 23, 175–182 (1981)], Chinese hamster ovary cells and a dihydrofolate reductase-deficient cell line derived therefrom [Proc. Natl. Acad. Sci. USA, 77, 4216–4220 (1980)] and the like, which are frequently used.

As regards the expression vector to be used with vertebrate cells, an expression vector having a promoter located upstream of the gene to be expressed, RNA splicing sites, a polyadenylation site and a transcription termination sequence can be generally used. This may further have an origin of replication as necessary. As an example of said expression vector, there may be mentioned pSV2dhfr [Mol. Cell. Biol., 1, 854 (1981)], which has the SV40 early promoter. As for the eukaryotic microorganisms, yeasts are generally and frequently used and, among them, yeasts of the genus Saccharomyces can be used with advantage. As regards the expression vector for use with said yeasts and other eukaryotic microorganisms, pAM82 [Proc. Natl. Acad. Sci. USA, 80, 1–5 (1983)], which has the acid phosphatase gene promoter, for instance, can be used.

Furthermore, a prokaryotic gene fused vector can be preferably used as the expression vector for the gene of the present invention. As specific examples of said vector, there may be mentioned pGEX-2TK and pGEX-4T-2 which have a GST domain (derived from *S. japonicum*) with a molecular weight of 26,000.

*Escherichia coli* and *Bacillus subtilis* are generally and preferably used as prokaryotic hosts. When these are used as hosts in the practice of the present invention, an expression plasmid derived from a plasmid vector capable of replicating in said host organisms and provided in this vector with a promoter and the SD (Shine and Dalgarno) sequence upstream of said gene for enabling the expression of the gene of the present invention and further provided with an initiation codon (e.g. ATG) necessary for the initiation of protein synthesis is preferably used. The *Escherichia coli* strain K12, among others, is preferably used as the host *Escherichia coli,* and pBR322 and modified vectors derived therefrom are generally and preferably used as the vector, while various known strains and vectors can also be used. Examples of the promoter which can be used are the tryptophan (trp) promoter, lpp promoter, lac promoter and PL/PR promoter.

The thus-obtained desired recombinant DNA can be introduced into host cells for transformation by using various general methods. The transformant obtained can be cultured by a conventional method and the culture leads to expression and production of the desired protein encoded by the gene of the present invention. The medium to be used in said culture can suitably be selected from among various media in conventional use according to the host cells employed. The host cells can be cultured under conditions suited for the growth thereof.

In the above manner, the desired recombinant protein is expressed and produced and accumulated or secreted within the transformant cells or extracellularly or on the cell membrane.

The recombinant protein can be separated and purified as desired by various separation procedures utilizing the physical, chemical and other properties thereof [cf. e.g. "Seikagaku (Biochemistry) Data Book II", pages 1175–1259, 1st Edition, 1st Printing, published Jun. 23, 1980 by Tokyo Kagaku Dojin; Biochemistry, 25 (25), 8274–8277 (1986); Eur. J. Biochem., 163, 313–321 (1987)]. Specifically, said procedures include, among others, ordinary reconstitution treatment, treatment with a protein precipitating agent (salting out), centrifugation, osmotic shock treatment, sonication, ultrafiltration, various liquid chromatography techniques such as molecular sieve chromatography (gel filtration), adsorption chromatography, ion exchange chromatography, affinity chromatography and high-performance liquid chromatography (HPLC), dialysis and combinations thereof. Among them, affinity chromatography utilizing a column with the desired protein bound thereto is particularly preferred.

Furthermore, on the basis of the sequence information about the gene of the present invention as revealed by the present invention, for example by utilizing part or the whole of said gene, it is possible to detect the expression of the gene of the present invention in various human tissues. This can be performed by a conventional method, for example by RNA amplification by RT-PCR (reverse transcribed-polymerase chain reaction) [Kawasaki, E. S., et al., Amplification of RNA, in PCR Protocol, A guide to methods and applications, Academic Press, Inc., San Diego, 21–27 (1991)], or by northern blotting analysis [Molecular Cloning, Cold Spring Harbor Laboratory (1989)], with good results.

The primers to be used in employing the above-mentioned PCR method are not limited to any particular ones provided that they are specific to the gene of the present invention and enable the gene of the present invention alone to be specifically amplified. They can be designed or selected apropriately based on the gene information provided by the present invention. They can have a partial sequence comprising about 20 to 30 nucleotides according to the established practice. Suitable examples are as shown in Examples 1 to 11.

Thus, the present invention also provides primers and/or probes useful in specifically detecting such novel gene.

By using the novel gene provided by the present invention, it is possible to detect the expression of said gene in various tissues, analyze the structure and function thereof and, further, produce the human protein encoded by said gene in the manner of genetic enginnering. These make it possible to analyze the expression product, reveal the pathology of a disease associated therewith, for example a genopathy or cancer, and diagnose and treat the disease.

BRIEF DESCRIPTION OF THE DRAWINGS

The following drawings are referred to in the examples.

FIG. 1 shows the result obtained by testing the PI4 kinase activity of NPIK in Example 9.

FIG. 2 shows the effect of Triton X-100 and adenosine on NPIK activity.

EXAMPLES

The following examples illustrate the present invention in further detail.

Example 1
GDP dissociation stimulator gene
(1) Cloning and DNA sequencing of GDP dissociation stimulator gene
mRNAs extracted from the tissues of human fetal brain, adult blood vessels and placenta were purchased from Clontech and used as starting materials.

cDNA was synthesized from each mRNA and inserted into the vector λZAPII (Stratagene) to thereby construct a cDNA library (Otsuka GEN Research Institute, Otsuka Pharmaceutical Co., Ltd.)

Human gene-containing *Escherichia coli* colonies were allowed to form on agar medium by the in vivo excision technique [Short, J. M., et al., Nucleic Acids Res., 16, 7583–7600 (1988)]. Colonies were picked up at random and human gene-containing *Escherichia coli* clones were registered on 96-well micro plates. The clones registered were stored at −80° C.

Each of the clones registered was cultured overnight in 1.5 ml of LB medium, and DNA was extracted and purified using a model PI-100 automatic plasmid extractor (Kurabo). Contaminant *Escherichia coli* RNA was decomposed and removed by RNase treatment. The DNA was dissolved to a final volume of 30 $\mu$l. A 2-$\mu$l portion was used for roughly checking the DNA size and quantity using a minigel, 7 $\mu$l was used for sequencing reactions and the remaining portion (21 $\mu$l) was stored as plasmid DNA at 4° C.

This method, after slight changes in the program, enables extraction of the cosmid, which is useful also as a probe for FISH (fluorescence in situ hybridization) shown later in the examples.

Then, the dideoxy terminator method of Sanger et al. [Sanger, F., et al., Proc. Natl. Acad. Sci. USA, 74, 5463–5467 (1977)] using T3, T7 or a synthetic oligonucleotide primer or the cycle suquence method [Carothers, A. M., et al., Bio. Techniques, 7, 494–499 (1989)] comprising the dideoxy chain terminator method plus PCR method was carried out. These are methods of terminating the extension reaction specifically to the four bases using a small amount of plasmid DNA (about 0.1 to 0.5 $\mu$g) as a template.

The sequence primers used were FITC (fluorescein isothiocyanate)-labeled ones. Generally, about 25 cycles of reaction were performed using Taq polymerase. The PCR products were separated on a polyacrylamide urea gel and the fluorescence-labeled DNA fragments were submitted to an automatic DNA sequencer (ALF™ DNA Sequencer; Pharmacia) for determining the sequence of about 400 bases from the 5' terminus side of cDNA.

Since the 3' nontranslational region is high in heterogeneity for each gene and therefore suited for discriminating individual genes from one another, sequencing was performed on the 3' side as well depending on the situation.

The vast sum of nucleotide sequence information obtained from the DNA sequencer was transferred to a 64-bit DEC 3400 computer for homology analysis by the computer. In the homology analysis, a data base (GenBank, EMBL) was used for searching according to the UWGCG FASTA program [Pearson, W. R. and Lipman, D. J., Proc. Natl. Acad. Sci. USA, 85, 2444–2448 (1988)].

As a result of arbitrary selection by the above method and of cDNA sequence analysis, a clone designated as GEN-501D08 and having a 0.8 kilobase insert was found to show a high level of homology to the C terminal region of the human Ral guanine nucleotide dissociation stimulator (RalGDS) gene. Since RalGDS is considered to play a certain role in signal transmission pathways, the whole nucleotide sequence of the cDNA insert portion providing the human homolog was further determined.

Low-molecular GTPases play an important role in transmitting signals for a number of cell functions including cell proliferation, differentiation and transformation [Bourne, H. R. et al., Nature, 348, 125– 132 (1990); Bourne et al., Nature, 349, 117–127 (1991)].

It is well known that, among them, those proteins encoded by the ras gene family function as molecular switches or, in other words, the functions of the ras gene family are regulated by different conditions of binding proteins such as biologically inactive GDP-binding proteins or active GDP-binding proteins, and that these two conditions are induced by GTPase activating proteins (GAPs) or GDS. The former enzymes induce GDP binding by stimulating the hydrolysis of bound GTP and the latter enzyme induces the regular GTP binding by releasing bound GDP [Bogusuki, M. S. and McCormick, F., Nature, 366, 643–654 (1993)].

RalGDS was first discovered as a member of the ras gene family lacking in transforming activity and as a GDP dissociation stimulator specific to RAS [Chardin, P. and Tavitian, A., EMBO J., 5, 2203–2208 (1986); Albright, C. F., et al., EMBO J., 12, 339–347 (1993)].

In addition to Ral, RalGDS was found to function, through interaction with these proteins, as an effector molecule for N-ras, H-ras, K-ras and Rap [Spaargaren, M. and Bischoff, J. R., Proc. Natl. Acad. Sci. USA, 91, 12609–12613 (1994)].

The nucleotide sequence of the cDNA clone designated as GEN-501D08 is shown under SEQ ID NO:3, the nucleotide sequence of the coding region of said clone under SEQ ID NO:2, and the amino acid sequence encoded by said nucleotide sequence under SEQ ID NO:1.

This cDNA comprises 842 nucleotides, including an open reading frame comprising 366 nucleotides and coding for 122 amino acids. The translation initiation codon was found to be located at the 28th nucleotide residue.

Comparison between the RalGDS protein known among conventional databases and the amino acid sequence deduced from said cDNA revealed that the protein encoded by this cDNA is homologous to the C terminal domain of human RalGDS. The amino acid sequence encoded by this novel gene was found to be 39.5% identical with the C terminal domain of RalGDS which is thought to be necessary for binding to ras.

Therefore, it is presumable, as mentioned above, that this gene product might interact with the ras family proteins or have influence on the ras-mediated signal transduction pathways. However, this novel gene is lacking in the region coding for the GDS activity domain and the corresponding protein seems to be different in function from the GDS protein. This gene was named human RalGDS by the present inventors.

(2) Northern blot analysis

The expression of the RalGDS protein mRNA in normal human tissues was evaluated by Northern blotting using, as a probe, the human cDNA clone labeled by the random oligonucleotide priming method.

The Northern blot analysis was carried out with a human MTN blot (Human Multiple Tissue Northern blot; Clontech, Palo Alto, Calif., USA) according to the manufacturer's protocol.

Thus, the PCR amplification product from the above GEN-501D08 clone was labeled with [$^{32}$P]-dCTP (random-primed DNA labeling kit, Boehringer-Mannheim) for use as a probe.

For blotting, hybridization was performed overnight at 42° C. in a solution comprising 50% formamide/5×SSC/50× Denhardt's solution/0.1% SDS (containing 100 $\mu$g/ml denatured salmon sperm DNA). After washing with two portions of 2×SSC/0.01% SDS at room temperature, the membrane filter was further washed three times with 0.1×SSC/0.05% SDS at 50° C. for 40 minutes. An X-ray film (Kodak) was exposed to the filter at −70° C. for 18 hours.

As a result, it was revealed that a 900-bp transcript had been expressed in all the human tissues tested. In addition, a 3.2-kb transcript was observed specifically in the heart and skeletal muscle. The expression of these transcripts differing in size may be due either to alternative splicing or to cross hybridization with homologous genes.

(3) Cosmid clone and chromosome localization by FISH

FISH was performed by screening a library of human chromosomes cloned in the cosmid vector pWE15 using, as a probe, the 0.8-kb insert of the cDNA clone [Sambrook, J., et al., Molecular Cloning, 2nd Ed., pp. 3.1–3.58, Cold Spring Harbor Laboratory Press, Cold Spring Harbor, New York (1989)].

FISH for chromosome assignment was carried out by the method of Inazawa et al. which comprises G-banding pattern comparison for confirmation [Inazawa, J., et al., Genomics, 17, 153–162 (1993)].

For use as a probe, the cosmid DNA (0.5 $\mu$g) obtained from chromosome screening and corresponding to GEN-501D08 was labeled with biotin-16-dUTP by nick translation.

To eliminate the background noise due to repetitive sequences, 0.5 $\mu$l of sonicated human placenta DNA (10 mg/ml) was added to 9.5 $\mu$l of the probe solution. The mixture was denatured at 80° C. for 5 minutes and admixed with an equal volume of 4×SSC containing 20% dextran-sulfate. Then, a denatured slide was sown with the hybridization mixture and, after covering with paraffin, incubated in a wet chamber at 37° C. for 16 to 18 hours. After washing with 50% formamide/2×SSC at 37° C. for 15 minutes, the slide was washed with 2×SSC for 15 minutes and further with 1×SSC for 15 minutes.

The slide was then incubated in 4×SSC supplemented with "1% Block Ace" (trademark; Dainippon Pharmaceutical) containing avidin-FITC (5 $\mu$g/ml) at 37° C. for 40 minutes. Then, the slide was washed with 4×SSC for 10 minutes and with 4×SSC containing 0.05% Triton X-100 for 10 minutes and immersed in an antifading PPD solution [prepared by adjusting 100 mg of PPD (Wako Catalog No. 164-015321) and 10 ml of PBS(-) (pH 7.4) to pH 8.0 with 0.5M $Na_2CO_3$/0.5M $NaHCO_3$ (9:1, v/v) buffer (pH 9.0) and adding glycerol to make a total volume of 100 ml] containing 1% DABCO [1% DABCO (Sigma) in PBS(-):glycerol 1:9 (v:v)], followed by counter staining with DAPI (4,6-diamino-2-phenylindole; Sigma).

With more than 100 tested cells in the metaphase, a specific hybridization signal was observed on the chromosome band at 6p21.3, without any signal on other chromosomes. It was thus confirmed that the RalGDS gene is located on the chromosome 6p21.3.

By using the novel human RalGDS-associated gene of the present invention as obtained in this example, the expression of said gene in various tissues can be detected and the human RalGDS protein can be produced in the manner of genetic engineering. These are expected to enable studies on the roles of the expression product protein and ras-mediated signals in transduction pathways as well as pathological investigations of diseases in which these are involved, for example cancer, and the diagnosis and treatment of such diseases. Furthermore, it becomes possible to study the development and progress of diseases involving the same chromosomal translocation of the RalGDS protein gene of the present invention, for example tonic spondylitis, atrial septal defect, pigmentary retinopathy, aphasia and the like.

Example 2

Cytoskeleton-associated protein 2 gene (CKAP2 gene)

(1) Cytoskeleton-associated protein 2 gene cloning and DNA sequencing cDNA clones were arbitrarily chosen from a human fetal brain cDNA library in the same manner as in Example 1 were subjected to sequence analysis and, as a result, a clone having a base sequence containing the CAP-glycine domain of the human cytoskeleton-associated protein (CAP) gene and highly homologous to several CAP family genes was found and named GEN-080G01.

Meanwhile, the cytoskeleton occurs in the cytoplasm and just inside the cell membrane of eukaryotic cells and is a network structure comprising complicatedly entangled filaments. Said cytoskeleton is constituted of microtubules composed of tubulin, microfilaments composed of actin, intermediate filaments composed of desmin and vimentin, and so on. The cytoskeleton not only acts as supportive cellular elements but also isokinetically functions to induce morphological changes of cells by polymerization and depolymerization in the fibrous system. The cytoskeleton binds to intracellular organelles, cell membrane receptors and ion channels and thus plays an important role in intracellular movement and locality maintenance thereof and, in addition, is said to have functions in activity regulation and mutual information transmission. Thus it supposedly occupies a very important position in physiological activity regulation of the whole cell. In particular, the relation between canceration of cells and qualitative changes of the cytoskeleton attracts attention since cancer cells differ in morphology and recognition response from normal cells.

The activity of this cytoskeleton is modulated by a number of cytoskeleton-associated proteins (CAPs). One group of CAPs is characterized by a glycine motif highly conserved and supposedly contributing to association with microtubules [CAP-GLY domain; Riehemann, K. and Song, C., Trends Biochem. Sci., 18, 82–83 (1993)].

Among the members of this group of CAPs, there are CLIP-170, 150 kDa DAP (dynein-associated protein, or dynactin), *D. melanogaster* GLUED, *S. cerevisiae* BIK1, restin [Bilbe, G., et al., EMBO J., 11, 2103–2113 (1992)]; Hilliker, C., et al., Cytogenet. Cell Genet., 65, 172–176 (1994)] and *C. elegans* 13.5 kDa protein [Wilson, R., et al., Nature, 368, 32–38 (1994)]. Except for the last two proteins, direct or indirect evidences have suggested that they could interact with microtublues.

The above-mentioned CLIP-170 is essential for the in vitro binding of endocytic vesicles to microtubules and colocalizes with endocytic organelles [Rickard, J. E. and Kreis, T. E., J. Biol. Chem., 18, 82–83 (1990); Pierre, P., et al., Cell, 70, 887–900 (1992)].

The above-mentioned dynactin is one of the factors constituting the cytoplasmic dynein motor, which functions in retrograde vesicle transport [Schroer, T. A. and Sheetz, M. P., J. Cell Biol., 115, 1309–1318 (1991)] or probably in the movement of chromosomes during mitosis [Pfarr, C. M., et al., Nature, 345, 263–265 (1990); Steuer, E. R., et al., Nature, 345, 266–268 (1990); Wordeman, L., et al., J. Cell Biol., 114, 285–294 (1991)].

GLUED, the Drosophila homolog of mammalian dynactin, is essential for the viability of almost all cells and for the proper organization of some neurons [Swaroop, A., et al., Proc. Natl. Acad. Sci. USA, 84, 6501–6505 (1987); Holzbaur, E. L. P., et al., Nature, 351, 579–583 (1991)].

BIK1 interacts with microtubules and plays an important role in spindle formation during mitosis in yeasts [Trueheart, J., et al., Mol. Cell. Biol., 7, 2316–2326 (1987); Berlin, V., et al., J. Cell Biol., 111, 2573–2586 (1990)].

At present, these genes are classified under the term CAP family (CAPs).

As a result of database searching, the above-mentioned cDNA clone of 463-bp (excluding the poly-A signal) showed significant homology in nucleotide sequence with the restin and CLIP-170 encoding genes. However, said clone was lacking in the 5' region as compared with the restin gene and, therefore, the technique of 5' RACE

[Frohman, M. A., et al., Proc. Natl. Acad. Sci. USA, 85, 8998–9002 (1988)] was used to isolate this missing segment.

(2) 5' RACE (5' rapid amplification of cDNA ends)

A cDNA clone containing the 5' portion of the gene of the present invention was isolated for analysis by the 5' RACE technique using a commercial kit (5'-Rapid AmpliFinder RACE kit, Clontech) according to the manufacturer's protocol with minor modifications, as follows.

The gene-specific primer P1 and primer P2 used here were synthesized by the conventional method and their nucleotide sequences are as shown below in Table 1. The anchor primer used was the one attached to the commercial kit.

TABLE 1

| Primer | Nucleotide sequence |
|---|---|
| Primer P1 | 5'-ACACCAATCCAGTAGCCAGGCTTG-3' |
| Primer P2 | 5'-CACTCGAGAATCTGTGAGACCTACATACATGACG-3' |

cDNA was obtained by reverse transcription of 0.1 $\mu$g of human fetal brain poly(A)+RNA by the random hexamer technique using reverse transcriptase (Superscript ™ II, Life Technologies) and the cDNA was amplified by the first PCR using the P1 primer and anchor primer according to Watanabe et al. [Watanabe, T., et al., Cell Genet., in press).

Thus, to 0.1 $\mu$g of the above-mentioned cDNA were added 2.5 mM dNTP/1×Taq buffer (Takara Shuzo)/0.2 $\mu$M P1 primer, 0.2 $\mu$M adaptor primer/0.25 unit ExTaq enzyme (Takara Shuzo) to make a total volume of 50 $\mu$l, followed by addition of the anchor primer. The mixture was subjected to PCR. Thus, 35 cycles of amplification were performed under the conditions: 94° C. for 45 seconds, 60° C. for 45 seconds, and 72° C. for 2 minutes. Finally, the mixture was heated at 72° C. for 5 minutes.

Then, 1 $\mu$l of the 50-$\mu$l first PCR product was subjected to amplification by the second PCR using the specific nested P2 primer and anchor primer. The second PCR product was analyzed by 1.5% agarose gel electrophoresis.

Upon agarose gel electrophoresis, a single band, about 650 nucleotides in size, was detected. The product from this band was inserted into a vector (pT7Blue(R)T-Vector, Novagen) and a plurality of clones with an insert having an appropriate size were selected.

Six of the 5' RACE clones obtained from the PCR product had the same sequence but had different lengths. By sequencing two overlapping cDNA clones, GEN-080G01 and GEN-080G0149, the protein-encoding sequence and 5' and 3' flanking sequences, 1015 nucleotides in total length, were determined. Said gene was named cytoskeleton-associated protein 2 gene (CKAP2 gene).

The nucleotide sequence obtained from the above-mentioned two overlapping cDNA clones GEN-080G01 and GEN-080G0149 is shown under SEQ ID NO:6, the nucleotide sequence of the coding region of said clone under SEQ ID NO:5, and the amino acid sequence encoded by said nucleotide sequence under SEQ ID NO:4.

As shown under SEQ ID NO:6, the CKAP2 gene had a relatively GC-rich 5' noncoding region, with incomplete triplet repeats, (CAG)4(CGG)4(CTG)(CGG), occurring at nucleotides 40–69.

ATG located at nucleotides 274–276 is the presumable start codon. A stop codon (TGA) was situated at nucleotides 853–855. A polyadenylation signal (ATTAAA) was followed by 16 nucleotides before the poly(A) start. The estimated open reading frame comprises 579 nucleotides coding for 193 amino acid residues with a calculated molecular weight of 21,800 daltons.

The coding region was further amplified by RT-PCR, to eliminate the possibility of the synthetic sequence obtained being a cDNA chimera.

(2) Similarity of CKAP2 to other CAPs

While sequencing of CKAP2 revealed homology with the sequences of restin and CLIP-170, the homologous region was limited to a short sequence corresponding to the CAP-GLY domain. On the amino acid level, the deduced CKAP2 was highly homologous to five other CAPs in this domain.

CKAP2 was lacking in such other motif characteristics of some CAPs as the alpha helical rod and zinc finger motif. The alpha helical rod is thought to contribute to dimerization and to increase the microtubule binding capacity [Pierre, P., et al., Cell, 70, 887–900 (1992)]. The lack of the alpha helical domain might mean that CKAP2 be incapable of homo or hetero dimer formation.

Paralleling of the CAP-GLY domains of these proteins revealed that other conserved residues other than glycine residues are also found in CKAP2. CAPs having a CAP-GLY domain are thought to be associated with the activities of cellular organelles and the interactions thereof with microtubules. Since it contains a CAP-GLY domain, as mentioned above, CKAP2 is placed in the family of CAPs.

Studies with mutants of Glued have revealed that the Glued product plays an important role in almost all cells [Swaroop, A., et al., Proc. Natl. Acad. Sci. USA, 84, 6501–6505 (1987)] and that it has other neuron-specific functions in neuronal cells [Meyerowitz, E. M. and Kankel, D. R., Dev. Biol., 62, 112–142 (1978)]. These microtubule-associated proteins are thought to function in vesicle transport and mitosis. Because of the importance of the vesicle transport system in neuronal cells, defects in these components might lead to aberrant neuronal systems.

In view of the above, CKAP2 might be involved in specific neuronal functions as well as in fundamental cellular functions.

(3) Northern blot analysis

The expression of human CKAP2 mRNA in normal human tissues was examined by Northern blotting in the same manner as in Example 1 (2) using the GEN-080G01 clone (corresponding to nucleotides 553–1015) as a probe.

As a result, in all the eight tissues tested, namely human heart, brain, placenta, lung, liver, skeletal muscle, kidney and pancreas, a 1.0 kb transcript agreeing in size with the CKAP2 cDNA was detected. Said 1.0 kb transcript was expressed at significantly higher levels in heart and brain than in the other tissues examined. Two weak bands, 3.4 kb and 4.6 kb, were also detected in all the tissues examined.

According to the Northern blot analysis, the 3.4 kb and 4.6 kb transcripts might possibly be derived from the same gene coding for the 1.0 kb CKAP2 by alternative splicing or transcribed from other related genes. These characteristics of the transcripts may indicate that CKAP2 might also code for a protein having a CAP-GLY domain as well as an alpha helix.

(4) Cosmid cloning and chromosomal localization by direct R-banding FISH

Two cosmids corresponding to the CKAP2 cDNA were obtained. These two cosmid clones were subjected to direct R-banding FISH in the same manner as in Example 1 (3) for chromosomal locus mapping of CKAP2.

For suppressing the background due to repetitive sequences, a 20-fold excessive amount of human Cot-I DNA (BRL) was added as described by Lichter et al. [Lichter, P., et al., Proc. Natl. Acad. Sci. USA, 87, 6634–6638 (1990)].

A Provia 100 film (Fuji ISO 100; Fuji Photo Film) was used for photomicrography.

As a result, CKAP2 was mapped on chromosome bands 19q13.11-q13.12.

Two autosomal dominant neurological diseases have been localized to this region by linkage analysis: CADASIL (cerebral autosomal dominant arteriopathy with subcortical infarcts and leukoencephalopathy) between the DNA markers D19S221 and D19S222, and FHM (familial hemiplegic migraine) between D19S215 and D19S216. These two diseases may be allelic disorders in which the same gene is involved [Tournier-Lasserve, E., et al., Nature Genet., 3, 256–259 (1993); Joutel, A., et al., Nature Genet., 5, 40–45 (1993)].

Although no evidence is available to support CKAP2 as a candidate gene for FHM or CADASIL, it is conceivable that its mutation might lead to some or other neurological disease.

By using the novel human CKAP2 gene of the present invention as obtained in this example, it is possible to detect the expression of said gene in various tissues or produce the human CKAP2 gene in the manner of genetic engineering. Through these, it becomes possible to analyze the functions of the human CKAP2 system or human CKAP2, which is involved in diverse activities essential to cells, as mentioned above, to diagnose various neurological diseases in which said system or gene is involved, for example familial migraine, and to screen out and evaluate a therapeutic or prophylactic drug therefor.

Example 3

OTK27 gene (1) OTK27 gene cloning and DNA sequencing

As a result of sequence analysis of cDNA clones arbitrarily selected from a human fetal brain cDNA library in the same manner as in Example 1 (1) and database searching, a cDNA clone, GEN-025F07, coding for a protein highly homologous to NHP2, a yeast nucleoprotein [*Saccharomyces cerevisiae;* Kolodrubetz, D. and Burgum, A., YEAST, 7, 79–90 (1991)], was found and named OTK27.

Nucleoproteins are fundamental cellular constituents of chromosomes, ribosomes and so forth and are thought to play an essential role in cell multiplication and viability. The yeast nucleoprotein NHP2, a high-mobility group (HMG)-like protein, like HMG, has reportedly a function essential for cell viability [Kolodrubetz, D. and Burgum, A., YEAST, 7, 79–90 (1991)].

The novel human gene, OTK27 gene, of the present invention, which is highly homologous to the above-mentioned yeast NHP2 gene, is supposed to be similar in function.

The nucleotide sequence of said GEN-025F07 clone was found to comprise 1493 nucleotides, as shown under SEQ ID NO:9, and contain an open reading frame comprising 384 nucleotides, as shown under SEQ ID NO:8, coding for an amino acid sequence comprising 128 amino acid residues, as shown under SEQ ID NO:7. The initiation codon was located at nucleotides 95–97 of the sequence shown under SEQ ID NO:9, and the termination codon at nucleotides 479–481.

At the amino acid level, the OTK27 protein was highly homologous (38%) to NHP2. It was 83% identical with the protein deduced from the cDNA from *Arabidopsis thaliana;* Newman, T., unpublished; GENEMBL Accession No. T14197).

(2) Northern blot analysis

For examining the expression of human OTK27 mRNA in normal human tissues, the insert in the OTK27 cDNA was amplified by PCR, the PCR product was purified and labeled with [$^{32}$ P]-dCTP (random-primed DNA labeling kit, Boehringer Mannheim), and Northern blotting was performed using the labeled product as a probe in the same manner as in Example 1 (2).

As a result of the Northern blot analysis, two bands corresponding to possible transcripts from this gene were detected at approximately 1.6 kb and 0.7 kb. Both sizes of transcript were expressed in all normal adult tissues examined. However, the expression of the 0.7 kb transcript was significantly reduced in brain and was of higher levels in heart, skeletal muscle and testicle than in other tissues examined.

For further examination of these two transcripts, eleven cDNA clones were isolated from a testis cDNA library and their DNA sequences were determined in the same manner as in Example 1 (1).

As a result, in six clones, the sequences were found to be in agreement with that of the 0.7 kb transcript, with a poly(A) sequence starting at around the 600th nucleotide, namely at the 598th nucleotide in two of the six clones, at the 606th nucleotide in three clones, and at the 613th nucleotide in one clone.

In these six clones, the “TATAAA” sequence was recognized at nucleotides 583–588 as a probable poly(A) signal. The upstream poly(A) signal “TATAAA” of this gene was recognized as little influencing in brain and more effective in the three tissues mentioned above than in other tissues. The possibility was considered that the stability of each transcript vary from tissue to tissue.

Results of zoo blot analysis indicated that this gene is well conserved also in other vertebrates. Since this gene is expressed ubiquitously in normal adult tissues and conserved among a wide range of species, the gene product is likely to play an important physiological role. The evidence that yeasts lacking in NHP2 are nonviable suggests that the human homolog may also be essential to cell viability.

(3) Chromosomal localization of OTK27 by direct R-banding FISH

One cosmid clone corresponding to the cDNA OTK27 was isolated from a total human genomic cosmid library (5-genome equivalent) using the OTK27 cDNA insert as a probe and subjected to FISH in the same manner as in Example 1 (3) for chromosomal localization of OTK27.

As a result, two distinct spots were observed on the chromosome band 12q24.3.

The OTK27 gene of the present invention can be used in causing expression thereof and detecting the OTK27 protein, a human nucleoprotein, and thus can be utilized in the diagnosis and pathologic studies of various diseases in which said protein is involved and, because of its involvement in cell proliferation and differentiation, in screening out and evaluating therapeutic and preventive drugs for cancer.

Example 4

OTK18 gene (1) OTK18 gene cloning and DNA sequencing

Zinc finger proteins are defined as constituing a large family of transcription-regulating proteins in eukaryotes and carry evolutionally conserved structural motifs [Kadonaga, J. T., et al., Cell, 51, 1079–1090 (1987); Klung, A. and Rhodes, D., Trends Biol. Sci., 12, 464–469 (1987); Evans, R. M. and Hollenberg, S. M., Cell, 52, 1–3 (1988)].

The zinc finger, a loop-like motif formed by the interaction between the zinc ion and two residues, cysteine and histidine residues, is involved in the sequence-specific binding of a protein to RNA or DNA. The zinc finger motif was first identified within the amino acid sequence of the Xenopus transcription factor IIIA [Miller, J., et al., EMBO J., 4, 1609–1614 (1986)].

The $C_2H_2$ finger motif is in general tandemly repeated and contains an evolutionally conserved intervening sequence of 7 or 8 amino acids. This intervening stretch was first identified in the Kruppel segmentation gene of Drosophila [Rosenberg, U. B., et al., Nature, 319, 336–339 (1986)]. Since then, hundreds of $C_2H_2$ zinc finger protein-encoding genes have been found in vertebrate genomes.

As a result of sequence analysis of cDNA clones arbitrarily selected from a human fetal brain cDNA library in the same manner as in Example 1 (1) and database searching, several zinc finger structure-containing clones were identified and, further, a clone having a zinc finger structure of the Kruppel type was found.

Since this clone lacked the 5' portion of the transcript, plaque hybridization was performed with a fetal brain cDNA library using, as a probe, an approximately 1.8 kb insert in the cDNA clone, whereby three clones were isolated. The nucleotide sequences of these were determined in the same manner as in Example 1 (1).

Among the three clones, the one having the largest insert spans 3,754 nucleotides including an open reading frame of 2,133 nucleotides coding for 711 amino acids. It was found that said clone contains a novel human gene coding for a peptide highly homologous in the zinc finger domain to those encoded by human ZNF41 and the Drosophila Kruppel gene. This gene was named OTK18 gene (derived from the clone GEN-076C09).

The nucleotide sequence of the cDNA clone of the OTK18 gene is shown under SEQ ID NO:12, the coding region-containing nucleotide sequence under SEQ ID NO:11, and the predicted amino acid sequence encoded by said OTK18 gene under SEQ ID NO:10.

It was found that the amino acid sequence of OTK18 as deduced from SEQ ID NO:12 contains 13 finger motifs on its carboxy side.

(2) Comparison with other zinc finger motif-containing genes

Comparison among OTK18, human ZNF41 and the Drosophila Kruppel gene revealed that each finger motif is for the most part conserved in the consensus sequence $CXECGKAFXQKSXLX_2HQRXH$.

Comparison of the consensus sequence of the zinc finger motifs of OTK18 with those of human ZNF41 and the Drosophila Kruppel gene revealed that the Kruppel type motif is well conserved in the OTK18-encoded protein. However, the sequence similarities were limited to zinc finger domains and no significant homologies were found with regard to other regions.

The zinc finger domain interacts specifically with the target DNA, recognizing an about 5 bp sequence to thereby bind to the DNA helix [Rhodes, D. and Klug, A., Cell, 46, 123–132 (1986)].

Based on the idea that, in view of the above, the multiple module (tandem repetitions of zinc finger) can interact with long stretches of DNA, it is presumable that the target DNA of this gene product containing 13 repeated zinc finger units would be a DNA fragment with a length of approximately 65 bp.

(3) Northern blot analysis

Northern blot analysis was performed as described in Example 1 (2) for checking normal human tissues for expression of the human OTK18 mRNA therein by amplifying the insert of the OTK18 cDNA by PCR, purifying the PCR product, labeling the same with [$^{32}$P]-dCTP (random-primed DNA labeling kit, Boehringer Mannheim) and using an MTN blot with the labeled product as a probe.

The results of Northern blot analysis revealed that the transcript of OTK18 is approximately 4.3 kb long and is expressed ubiquitously in various normal adult tissues. However, the expression level in the liver and in peripheral blood lymphocytes seemed to be lower than in other organs tested.

(4) Cosmid cloning and chromosomal localization by direct R-banding FISH

Chromosomal localization of OTK18 was carried out as described in Example 1 (3).

As a result, complete twin spots were identified with 8 samples while 23 samples showed an incomplete signal or twin spots on either or both homologs. All signals appeared at the q13.4 band of chromosome 19. No twin spots were observed on any other chromosomes.

The results of FISH thus revealed that this gene is localized on chromosomal band 19q13.4. This region is known to contain many DNA segments that hybridize with oligonucleotides corresponding to zinc finger domains [Hoovers, J. M. N., et al., Genomics, 12, 254–263 (1992)]. In addition, at least one other gene coding for a zinc finger domain has been identified in this region [Marine, J.-C., et al., Genomics, 21, 285–286 (1994)].

Hence, the chromosome 19q13 is presumably a site of grouping of multiple genes coding for transcription-regulating proteins.

When the novel human OTK18 gene provided by this example is used, it becomes possible to detect expression of said gene in various tissues and produce the human OTK18 protein in the manner of genetic engineering. Through these, it is possible to analyze the functions of the human transcription regulating protein gene system or human transcription regulating proteins, which are deeply involved in diverse activities fundamental to cells, as mentioned above, to diagnose various diseases with which said gene is associated, for example malformation or cancer resulting from a developmental or differentiation anomaly, and mental or nervous disorder resulting from a developmental anomaly in the nervous system, and further to screen out and evaluate therapeutic or prophylactic drugs for these diseases.

Example 5

Genes encoding human 26S proteasome constituent P42 protein and P27 protein (1) Cloning and DNA sequencing of genes respectively encoding human 26S proteasome constituent P42 protein and P27 protein Proteasome, which is a multifunctional protease, is an enzyme occurring widely in eukaryotes from yeasts to humans and decomposing ubiquitin-binding proteins in cells in an energy-dependent manner. Structurally, said proteasome is constituted of 20S proteasome composed of various constituents with a molecular weight of 21 to 31 kilodaltons and a group of PA700 regulatory proteins composed of various constituents with a molecular weight of 30 to 112 kilodaltons and showing a sedimentation coefficient of 22S and, as a whole, occurs as a macromolecule with a molecular weight of about 2 million daltons and a sedimentation coefficient of 26S [Rechsteiner, M., et al., J. Biol. Chem., 268, 6065–6068 (1993); Yoshimura, T., et al., J. Struct. Biol., 111, 200–211 (1993); Tanaka, K., et al., New Biologist, 4, 173–187 (1992)].

Despite structural and mechanical analyses thereof, the whole picture of proteasome is not yet fully clear. However, according to studies using yeasts and mice in the main, it reportedly has the functions mentioned below and its functions are becoming more and more elucidated.

The mechanism of energy-dependent proteolysis in cells starts with selection of proteins by ubiquitin binding. It is not 20S proteasome but 26S proteasome that has ubiquitin-conjugated protein decomposing activity which is ATP-dependent [Chu-Ping et al., J. Biol. Chem., 269, 3539–3547 (1994)]. Hence, human 26S proteasome is considered to be useful in elucidating the mechanism of energy-dependent proteolysis.

Factors involved in the cell cycle regulation are generally short in half-life and in many cases they are subject to strict quantitative control. In fact, it has been made clear that the oncogene products Mos, Myc, Fos and so forth can be decomposed by 26S proteasome in an energy- and ubiquitin-dependent manner [Ishida, N., et al., FEBS Lett., 324, 345–348 (1993); Hershko, A. and Ciechanover, A., Annu. Rev. Biochem., 61, 761–807 (1992)] and the importance of proteasone in cell cycle control is being recognized.

Its importance in the immune system has also been pointed out. It is suggested that proteasome is positively involved in class I major histocompatible complex antigen presentation [Michalek, M. T., et al., Nature, 363, 552–554 (1993)] and it is further suggested that proteasome may be involved in Alzheimer disease, since the phenomena of abnormal accumulation of ubiquitin-conjugated proteins in the brain of patients with Alzheimer disease [Kitaguchi, N., et al., Nature, 361, 530–532 (1988)]. Because of its diverse functions such as those mentioned above, proteasome attracts attention from the viewpoint of its utility in the diagnosis and treatment of various diseases.

A main function of 26S proteasome is ubiquitin-conjugated protein decomposing activity. In particular, it is known that cell cycle-related gene products such as oncogene products and cyclins, typically c-Myc, are degraded via ubiquitin-dependent pathways. It has also been observed that the proteasome gene is expressed abnormally in liver cancer cells, renal cancer cells, leukemia cells and the like as compared with normal cells [Kanayama, H., et al., Cancer Res., 51, 6677–6685 (1991)] and that proteasome is abnormally accumulated in tumor cell nuclei. Hence, constituents of proteasome are expected to be useful in studying the mechanism of such canceration and in the diagnosis or treatment of cancer.

Also, it is known that the expression of proteasome is induced by interferon γ and so on and is deeply involved in antigen presentation in cells [Aki, M., et al., J. Biochem., 115, 257–269 (1994)]. Hence, constituents of human proteasome are expected to be useful in studying the mechanism of antigen presentation in the immune system and in developing immunoregulating drugs.

Furthermore, proteasome is considered to be deeply associated with ubiquitin abnormally accumulated in the brain of patients with Alzheimer disease. Hence, it is suggested that constituents of human proteasome should be useful in studying the cause of Alzheimer disease and in the treatment of said disease.

In addition to the utilization of expectedly multifunctional proteasome as such in the above manner, it is probably possible to produce antibodies using constituents of proteasome as antigens and use such antibodies in diagnosing various diseases by immunoassay. Its utility in this field of diagnosis is thus also a focus of interest.

Meanwhile, a protein having the characteristics of human 26S proteasome is disclosed, for example in Japanese Unexamined Patent Publication No. 292964/1993 and rat proteasome constituents are disclosed in Japanese Unexamined Patent Publication Nos. 268957/1993 and 317059/1993. However, no human 26S proteasome constituents are known. Therefore, the present inventors made a further search for human 26S proteasome constituents and successfully obtained two novel human 26S proteasome constituents, namely human 26S proteasome constituent P42 protein and human S26 proteasome constituent P27 protein, and performed cloning and DNA sequencing of the corresponding genes in the following manner.

(1) Purification of human 26S proteasome constituents P42 protein and P27 protein Human proteasome was purified using about 100 g of fresh human kidney and following the method of purifying human proteasome as described in Japanese Unexamined Patent Publication No. 292964/1993, namely by column chromatography using BioGel A-1.5 m (5×90 cm, Bio-Rad), hydroxyapatite (1.5×15 cm, Bio-Rad) and Q-Sepharose (1.5×15 cm, Pharmacia) and glycerol density gradient centrifugation.

The thus-obtained human proteasome was subjected to reversed phase high performance liquid chromatography (HPLC) using a Hitachi model L6200 HPLC system. A Shodex RS Pak D4-613 (0.6×15 cm, Showa Denko) was used and gradient elution was performed with the following two solutions:

First solution: 0.06% trifluoroacetic acid;

Second solution: 0.05% trifluoroacetic acid, 70% acetonitrile.

An aliquot of each eluate fraction was subjected to 8.5% SDS-polyacrylamide electrophoresis under conditions of reduction with dithiothreitol. The P42 protein and P27 protein thus detected were isolated and purified.

The purified P42 and P27 proteins were respectively digested with 1 μg of trypsin in 0.1M Tris buffer (pH 7.8) containing 2M urea at 37° C. for 8 hours and the partial peptide fragments obtained were separated by reversed phase HPLC and their sequences were determined by Edman degradation. The results obtained are as shown below in Table 2.

TABLE 2

| Partial protein | Amino acid sequence |
|---|---|
| P42 (1) | VLNISLW |
| (2) | TLMELLNQMDGFDTLHR |
| (3) | AVSDFVVSEYXMXA |
| (4) | EVDPLVYNX |
| (5) | HGEIDYEAIVK |
| (6) | LSXGFNGADLRNVXTEAGMFAIXAD |
| (7) | MIMATNRPDTLDPALLRPGXL |
| (8) | IHIDLPNEQARLDILK |
| (9) | ATNGPRYVVVG |
| (10) | EIDGRLK |
| (11) | ALQSVGQIVGEVLK |
| (12) | ILAGPITK |
| (13) | XXVIELPLTNPELFQG |
| (14) | VVSSSLVDK |
| (15) | ALQDYRK |
| (16) | EHREQLK |
| (17) | KLESKLDYKPVR |
| P27 (1) | LVPTR |
| (2) | AKEEEIEAQIK |
| (3) | ANYEVLESQK |
| (4) | VEDALHQLHAR |
| (5) | DVDLYQVR |
| (6) | QSQGLSPAQAFAK |
| (7) | AGSQSGGSPEASGVTVSDVQE |
| (8) | GLLGXNIIPLQR |

(2) cDNA library screening, clone isolation and cDNA nucleotide sequence determination As mentioned in Example 1 (1), the present inventors have a database comprising about 30,000 cDNA data as constructed based on large-scale DNA sequencing using human fetal brain, arterial blood vessel and placenta cDNA libraries.

Based on the amino acid sequences obtained as mentioned above in (1), computer searching was performed with the FASTA program (search for homology between said amino acid sequences and the amino acid sequences estimated from the database). As regards P42, a clone (GEN-331G07) showing identity with regard to two amino acid sequences [(2) and (7) shown in table 2] was screened out and, as regards P27, a clone (GEN-163D09) showing identity with regard to two amino acid sequences [(1) and (8) shown in Table 2] was found.

For each of these clones, the 5' side sequence was determined by 5' RACE and the whole sequence was determined, in the same manner as in Example 2 (2).

As a result, it was revealed that the above-mentioned P42 clone GEN-331G07 comprises a 1,566-nucleotide sequence as shown under SEQ ID NO:15, inclusive of a 1,167-nucleotide open reading frame as shown under SEQ ID NO:14, and that the amino acid sequence encoded thereby is the one shown under SEQ ID NO:13 and comprises 389 amino acid residues.

The results of computer homology search revealed that the P42 protein is significantly homologous to the AAA (ATPase associated with a variety of cellular activities) protein family (e.g. P45, TBP1, TBP7, S4, MSS1, etc.). It was thus suggested that it is a new member of the AAA protein family.

As for the P27 clone GEN-163D09, it was revealed that it comprises a 1,128-nucleotide sequence as shown under SEQ ID NO:18, including a 669-nucleotide open reading frame as shown under SEQ ID NO:17 and that the amino acid sequence encoded thereby is the one shown under SEQ ID NO:16 and comprises 223 amino acid residues.

As regards the P27 protein, homology search using a computer failed to reveal any homologous gene among public databases. Thus, the gene in question is presumably a novel gene having an unknown function.

Originally, the above-mentioned P42 and P27 gene products were both purified as regulatory subunit components of proteasome complex. Therefore, these are expected to play an important role in various biological functions through proteolysis, for example a role in energy supply through decomposition of ATP and, hence, they are presumably useful not only in studying the function of human 26S proteasome but also in the diagnosis and treatment of various diseases caused by lowering of said biological functions, among others.

Example 6

BNAP gene (1) BNAP gene cloning and DNA sequencing

The nucleosome composed of DNA and histone is a fundamental structure constituting chromosomes in eukaryotic cells and is well conserved over borders among species. This structure is closely associated with the processes of replication and transcription of DNA. However, the nucleosome formation is not fully understood as yet. Only certain specific factors involved in nucleosome assembly (NAPs) have been identified. Thus, two acidic proteins, nucleoplasmin and N1, are already known to facilitate nucleosome construction [Kleinschmidt, J. A., et al., J. Biol. Chem., 260, 1166–1176 (1985); Dilworth, S. M., et al., Cell, 51, 1009–1018 (1987)].

A yeast gene, NAP-I, was isolated using a mono-clonal antibody and recombinant proteins derived therefrom were tested as to whether they have nucleosome assembling activity in vivo.

More recently, a mouse NAP-I gene, which is a mammalian homolog of the yeast NAP-I gene was cloned (Okuda, A.; registered in database under the accession number D12618). Also cloned were a mouse gene, DN38 [Kato, K., Eur. J. Neurosci., 2, 704–711 (1990)] and a human nucleosome assembly protein (hNRP) [Simon, H. U., et al., Biochem. J., 297, 389–397 (1994)]. It was shown that the hNRP gene is expressed in many tissues and is associated with T lymphocyte proliferation.

The present inventors performed sequence analysis of cDNA clones arbitrarily chosen from a human fetal brain cDNA library in the same manner as in Example 1 (1), followed by searches among databases and, as a result, made it clear that a 1,125-nucleotide cDNA clone (free of poly (A)), GEN-078D05, is significantly homologous to the mouse NAP-I gene, which is a gene for a nucleosome assembly protein (NAP) involved in nucleosome construction, a mouse partial cDNA clone, DN38, and hNRP.

Since said clone GEN-078D05 was lacking in the 5' region, 5' RACE was performed in the same manner as in Example 2 (2) to obtain the whole coding region. For this 5' RACE, primers P1 and P2 respectively having the nucleotide sequences shown below in Table 3.

TABLE 3

| Primer | Nucleotide sequence |
|---|---|
| Primer P1 | 5'-TTGAAGAATGATGCATTAGGAACCAC-3' |
| Primer P2 | 5'-CACTCGAGTGGCTGGATTTCAATTTCTCCAGTAG-3' |

After the first 5' RACE, a single band corresponding to a sequence length of 1,300 nucleotides was obtained. This product was inserted into pT7Blue(R) T-Vector and several clones appropriate in insert size were selected.

Ten 5' RACE clones obtained from two independent PCR reactions were sequenced and the longest clone GEN-078D05TA13 (about 1,300 nucleotides long) was further analyzed.

Both strands of the two overlapping cDNA clones GEN-078D05 and GEN-078D05TA13 were sequenced, whereby it was confirmed that the two clones did not yet cover the whole coding region. Therefore, a further second 5' RACE was carried out. For the second 5' RACE, two primers, P3 and P4, respectively having the sequences shown below in Table 4 were used.

TABLE 4

| Primer | Nucleotide sequence |
|---|---|
| Primer P3 | 5'-GTCGAGCTAGCCATCTCCTCTTCG-3' |
| Primer P4 | 5'-CATGGGCGACAGGTTCCGAGACC-3' |

A clone, GEN-078D0508, obtained by the second 5' RACE was 300 nucleotides long. This clone contained an estimable initiation codon and three preceding in-frame termination codons. From these three overlapping clones, it became clear that the whole coding region comprises 2,636 nucleotides. This gene was named brain-specific nucleosome assembly protein (BNAP) gene.

The BNAP gene contains a 1,518-nucleotide open reading frame shown under SEQ ID NO:20. The amino acid encoded thereby comprises 506 amino acid residues, as shown under SEQ ID NO:19, and the nucleotide sequence of the whole cDNA clone of BNAP is as shown under SEQ ID NO:21.

As shown under SEQ ID NO:21, the 5' noncoding region of said gene was found to be generally rich in GC. Candidate initiation codon sequences were found at nucleotides Nos. 266–268, 287–289 and 329–331. These three sequences all had well conserved sequences in the vicinity of the initiation codons [Kozak, M., J. Biol. Chem., 266, 19867–19870 (1991)].

According to the scanning model, the first ATG (nucleotides Nos. 266–268) of the cDNA clone may be the initiation codon. The termination codon was located at nucleotides Nos. 1784–1786.

The 3' noncoding redion was generally rich in AT and two polyadenylation signals (AATAAA) were located at nucleotides Nos. 2606–2611 and 2610–2615, respectively.

The longest open reading frame comprised 1,518 nucleotides coding for 506 amino acid residues and the calculated molecular weight of the BNAP gene product was 57,600 daltons.

Hydrophilic plots indicated that BNAP is very hydrophilic, like other NAPs.

For recombinant BNAP expression and purification and for eliminating the possibility that the BNAP gene sequence might give three chimera clones in the step of 5' RACE, RT-PCR was performed using a sequence comprising nucleotides Nos. 326–356 as a sense primer and a sequence comprising nucleotides Nos. 1758–1786 as an antisenses primer.

As a result, a single product of about 1,500 bp was obtained and it was thus confirmed that said sequence is not a chimera but a single transcript.

(2) Comparison between BNAP and NAPs

The amino acid sequence deduced from BNAP showed 46% identity and 65% similarity to hNRP.

The deduced BNAP gene product had motifs characteristic of the NAPs already reported and of BNAP. In general, half of the C terminus was well conserved in humans and yeasts.

The first motif (domain I) is KGIPDYWLI (corresponding to amino acid residues Nos. 309–317). This was observed also in hNRP (KGIPSFWLT) and in yeast NAP-I (KGIPEFWLT).

The second motif (domain II) is ASFFNFFSPP (corresponding to amino acid residues Nos. 437–446) and this was expressed as DSFFNFFAPP in hNRP and as ESFFNFFSP in yeast NAP-I.

These two motifs were also conserved in the deduced mouse NAP-I and DN38 peptides. Both conserved motifs were each a hydrophilic cluster, and the Cys in position 402 was also found conserved.

Half of the N terminus had no motifs strictly conserved from yeasts to mammalian species, while motifs conserved among mammalian species were found.

For instance, HDLERKYA (corresponding to amino acid residues Nos. 130 to 137) and IINAEYEPTEEECEW (corresponding to amino acid residues Nos. 150–164), which may be associated with mammal-specific functions, were found strictly conserved.

NAPs had acidic stretches, which are believed to be readily capable of binding to histone or other basic proteins. All NAPs had three acidic stretches but the locations thereof were not conserved.

BNAP has no such three acidic stretches but, instead, three repeated sequences (corresponding to amino acid residues Nos. 194–207, 208–221 and 222–235) with a long acidic cluster, inclusive of 41 amino acid residues out of 98 amino acid residues, the consensus sequence being ExxKExPEVKxEEK (each x being a nonconserved, mostly hydrophobic, residue).

Furthermore, it was revealed that the BNAP sequence had several BNAP-specific motifs. Thus, an extremely serine-rich doamin (corresponding to amino acid residues Nos. 24–72) with 33 (67%) of 49 amino acid residues being serine residues was found in the N-terminus portion. On the nucleic acid level, they were reflected as incomplete repetitions of AGC.

Following this serine-rich region, there appeared a basic domain (corresponding to amino acid residues Nos. 71–89) comprising 10 basic amino acid residues among 19 residues.

BNAP is supposed to be localized in the nucleus. Two possible signals localized in the nucleus were observed (NLSs). The first signal was found in the basic domain of BNAP and its sequence YRKKR (corresponding to amino acid residues Nos. 75–79) was similar to NLS (GRKKR) of Tat of HIV-1. The second signal was located in the C terminus and its sequence KKYRK (corresponding to amino acid residues Nos. 502–506) was similar to NLS (KKKRK) of the large T antigen of SV40. The presence of these two presumable NLSs suggested the localization of BNAP in the nucleus. However the possibility that other basic clusters might act as NLSs could not be excluded.

BNAP has several phosphorylation sites and the activity of BNAP may be controlled through phosphorylation thereof.

(3) Northern blot analysis

Northern blot analysis was performed as described in Example 1 (2). Thus, the clone GEN-078D05TA13 (corresponding to nucleotides Nos. 323 to 1558 in the BNAP gene sequence) was amplified by PCR, the PCR product was purified and labeled with [$^{32}$P]-dCTP (random-primed DNA labeling kit, Boehringer Mannheim), and the expression of BNAP mRNA in normal human tissues was examined using an MTN blot with the labeled product as a probe.

As a result of Northern blot analysis, a 3.0 kb transcript of BNAP was detected (8-hour exposure) in the brain among eight human adult tissues tested, namely heart, brain, placenta, lung, liver, skeletal muscle, kidney and pancreas and, after longer exposure (24 hours), a dim band of the same size was detected in the heart.

BNAP was found equally expressed in several sites of brain tested whereas, in other tissues, no signal was detected at all even after 72 hours of exposure. hNRP mRNA was found expressed everywhere in the human tissues tested whereas the expression of BNAP mRNA was tissue-specific.

(4) Radiation hubrid mapping

Chromosomal mapping of the BNAP clone was performed by means of radiation hibrid mapping [Cox, D. R., et al., Science, 250, 245–250 (1990)].

Thus, a total human genome radiation hybrid clone (G3RH) panel was purchased from Research Genetics, Inc., AL, USA and PCR was carried out for chromosomal mapping analysis according to the product manual using two primers, A1 and A2, respectively having the nucleotide sequences shown in Table 5.

TABLE 5

| Primer | Nucleotide sequence |
|---|---|
| A1 primer | 5'-CCTAAAAAGTGTCTAAGTGCCAGTT-3' |
| A2 primer | 5'-TCAGTGAAAGGGAAGGTAGAACAC-3' |

The results obtained were analyzed utilizing softwares usable on the Internet [Boehnke, M., et al., Am. J. Hum. Genet., 46, 581–586 (1991)].

As a result, the BNAP gene was found strongly linked to the marker DXS990 (LOD=1000, cR8000=–0.00). Since DXS990 is a marker localized on the chromosome Xq21.3-q22, it was established that BNAP is localized to the chromosomal locus Xq21.3-q22 where genes involved in several signs or symptoms of X-chromosome-associated mental retardation are localized.

The nucleosome is not only a fundamental chromosomal structural unit characteristic of eukaryotes but also a gene expression regulating unit. Several results indicate that genes with high transcription activity are sensitive to nuclease treatment, suggesting that the chromosome structure changes with the transcription activity [Elgin, S. C. R., J. Biol. Chem., 263, 19259–19262 (1988)].

NAP-I has been cloned in yeast, mouse and human and is one of the factors capable of promoting nucleosome construction in vivo. In a study performed on their sequences, NAPs containing the epitope of the specific antibody 4A8 were detected in human, mouse, frog, Drosophila and yeast (*Saccharomyces cerevisiae*) [Ishimi, Y., et al., Eur. J. Biochem., 162, 19–24 (1987)].

In these experiments, NAPs, upon SDS-PAGE analysis, electrophoretically migrated to positions corresponding to a molecular weight between 50 and 60 kDa, whereas the recombinant BNAP slowly migrated to a position of about 80 kDa. The epitope of 4A8 was shown to be localized in the second, well-conserved, hydrophobic motif. And, it was simultaneously shown that the triplet FNF is important as a part of the epitope [Fujii-Nakata, T., et al., J. Biol. Chem., 267, 20980– 20986 (1992)].

BNAP also contained this consensus motif in domain II. The fact that domain II is markedly hydrophobic and the fact that domain II can be recognized by the immune system suggest that it is probably presented on the BNAP surface and is possibly involved in protein-protein interactions.

Domain I, too, may be involved in protein-protein interactions. Considering that these are conserved generally among NAPs, though to a relatively low extent, it is conceivable that they must be essential for nucleosome construction, although the functional meaning of the conserved domains is still unknown.

The hNRP gene is expressed in thyroid gland, stomach, kidney, intestine, leukemia, lung cancer, mammary cancer and so on [Simon, H. U., et al., Biochem. J., 297, 389–397 (1994)]. Like that, NAPs are expressed everywhere and are thought to be playing an important role in fundamental nucleosome formation.

BNAP may be involved in brain-specific nucleosome formation and an insufficiency thereof may cause neurological diseases or mental retardation as a result of deviated functions of neurons.

BNAP was found strongly linked to a marker on the X-chromosome q21.3-q22 where sequences involved in several symptoms of X-chromosome-associated mental retardation are localized. This center-surrounding region of X-chromosome was rich in genes responsible for α-thalassemia, mental retardation (ATR-X) or some other forms of mental retardation [Gibbons, R. J., et al., Cell, 80, 837–845 (1995)]. Like the analysis of the ATR-X gene which seems to regulate the nucleosome structure, the present inventors suppose that BNAP may be involved in a certain type of X-chromosome-linked mental retardation.

According to this example, the novel BNAP gene is provided and, when said gene is used, it is possible to detect the expression of said gene in various tissues and to produce the BNAP protein by the technology of genetic engineering. Through these, it is possible to study the brain nucleosome formation deeply involved, as mentioned above, in variegated activities essential to cells as well as the functions of cranial nerve cells and to diagnose various neurological diseases or mental retardation in which these are involved and screen out and evaluate drugs for the treatment or prevention of such diseases.

Example 7

Human skeletal muscle-specific ubiquitin-conjugating enzyme gene (UBE2G gene)

The ubiquitin system is a group of enzymes essential for cellular processes and is conserved from yeast to human. Said system is composed of ubiquitin-activating enzymes (UBAs), ubiquitin-conjugating enzymes (UBCs), ubiquitin protein ligases (UBRs) and 26S proteasome particles.

Ubiquitin is transferred from the above-mentioned UBAs to several UBCs, whereby it is activated. UBCs transfer ubiquitins to target proteins with or without the participation of UBRs. These ubiquitin-conjugated target proteins are said to induce a number of cellular responses, such as protein degradation, protein modification, protein translocation, DNA repair, cell cycle control, transcription control, stress responses, etc. and immunological responses [Jentsch, S., et al., Biochim. Biophys. Acta, 1089, 127–139 (1991); Hershko, A. and Ciechanover, A., Annu. Rev. Biochem., 61, 761–807 (1992); Jentsch, S., Annu. Rev. Genet., 26, 179–207 (1992); Ciechanover, A., Cell, 79, 13–21 (1994)].

UBCs are key components of this system and seem to have distinct substrate specificities and modulate different functions. For example, *Saccharomyces cerevisiae* UBC7 is induced by cadmium and involved in resistance to cadmium poisoning [Jungmann, J., et al., Nature, 361, 369–371 (1993) ]. Degradation of MAT-α2 is also executed by UBC7 and UBC6 [Chen, P., et al., Cell, 74, 357–369 (1993)].

The novel gene obtained in this example is UBC7-like gene strongly expressed in human skeletal muscle. In the following, cloning and and DNA sequencing thereof are described.

(1) Cloning and DNA sequencing of human skeletal muscle-specific ubiquitin-conjugating enzyme gene (UBE2G gene)

Following the same procedure as in Example 1 (1), cDNA clones were arbitrarily selected from a human fetal brain cDNA library and subjected to sequence analysis, and database searches were performed. As a result, a cDNA clone, GEN-423A12, was found to have a significantly high level of homology to the genes coding for ubiquitin-conjugating enzymes (UBCs) in various species.

Since said GEN-423A12 clone was lacking in the 5' side, 5' RACE was performed in the same manner as in Example 2 (2) to obtain an entire coding region.

For said 5' RACE, two primers, P1 and P2, respectively having the nucleotide sequences shown in Table 6 were used.

TABLE 6

| Primer | Nucleotide sequence |
|---|---|
| P1 primer | 5'-TAATGAATTTCATTTTAGGAGGTCGG-3' |
| P2 primer | 5'-ATCTTTTGGGAAAGTAAGATGAGCC-3' |

The 5' RACE product was inserted into pT7Blue(R) T-Vector and clones with an insert proper in size were selected.

Four of the 5' RACE clones obtained from two independent PCR reactions contained the same sequence but were different in length.

By sequencing the above clones, the coding sequence and adjacent 5'- and 3'-flanking sequences of the novel gene were determined.

As a result, it was revealed that the novel gene has a total length of 617 nucleotides. This gene was named human skeletal muscle-specific ubiquitin-conjugating enzyme gene (UBE2G gene).

To exclude the conceivable possibility that this sequence was a chimera clone, RT-PCR was performed in the same manner as in Example 6 (1) using the sense primer to amplify said sequence from the human fetal brain cDNA library. As a result, a single PCR product was obtained, whereby it was confirmed that said sequence is not a chimera one.

The UBE2G gene contains an open reading frame of 510 nucleotides, which is shown under SEQ ID NO:23, the amino acid sequence encoded thereby comprises 170 amino acid residues, as shown under SEQ ID NO:22, and the nucleotide sequence of the entire UBE2G cDNA is as shown under SEQ ID NO:24.

As shown under SEQ ID NO:24, the estimable initiation codon was located at nucleotides Nos. 19–21, corresponding to the first ATG triplet of the cDNA clone. Since no preceding in-frame termination codon was found, it was deduced that this clone contains the entire open reading frame on the following grounds.

Thus, (a) the amino acid sequence is highly homologous to S. cerevisiae UBC7 and said initiation codon agrees with that of yeast UBC7, supporting said ATG as such. (b) The sequence AGGATGA is similar to the consensus sequence (A/G)CCATGG around the initiation codon [Kozak, M., J. Biol. Chem., 266, 19867–19870 (1991)].

(2) Comparison in amino acid sequence between UBE2G and UBCs

Comparison in amino acid sequence between UBE2G and UBCs suggested that the active site cystein capable of binding to ubiquitin should be the 90th residue cystein. The peptides encoded by these genes seem to belong to the same family.

(3) Northern blot analysis

Northern blot analysis was carried out as described in Example 1 (2). Thus, the entire sequence of UBE2G was amplified by PCR, the PCR product was purified and labeled with [$^{32}$P]-dCTP (random-primed DNA labeling kit, Boehringer Mannheim) and the expression of UBE2G mRNA in normal human tissues using the labeled product as a probe. The membrane used was an MTN blot.

As a result of the Northern blot analysis, 4.4 kb, 2.4 kb and 1.6 kb transcripts could be detected in all 16 human adult tissues, namely heart, brain, placenta, lung, liver, skeletal muscle, kidney, pancreas, spleen, thyroid gland, urinary bladder, testis, ovary, small intestine, large intestine and peripheral blood leukocye, after 18 hours of exposure. Strong expression of these transcripts was observed in skeletal muscle.

(4) Radiation hybrid mapping

Chromosomal mapping of the UBE2G clone was performed by radiation hybrid mapping in the same manner as in Example 6 (4).

The primers C1 and C4 used in PCR for chromosomal mapping analysis respectively correspond to nucleotides Nos. 415–435 and nucleotides Nos. 509–528 in the sequence shown under SEQ ID NO:24 and their nucleotide sequences are as shown below in Table 7.

TABLE 7

| Primer | Nucleotide sequence |
|---|---|
| C1 primer | 5'-GGAGACTCACCTGCTAATGTT-3' |
| C4 primer | 5'-CTCAAAAGCAGTCTCTTGGC-3' |

As a result, the UBE2G gene was found linked to the markers D1S446 (LOD=12.52, cR8000=8.60) and D1S235 (LOD=9.14, cR8000=22.46). These markers are localized to the chromosome bands 1q42.13-q42.3.

UBE2G was expressed strongly in skeletal muscle and very weakly in all other tissues examined. All other UBCs are involved in essential cellular functions, such as cell cycle control, and those UBCs are expressed ubiquitously. However, the expression pattern of UBE2G might suggest a muscle-specific role thereof.

While the three transcripts differing in size were detected, attempts failed to identify which corresponds to the cDNA clone. The primary structure of the UBE2G product showed an extreme homology to yeast UBC7. On the other hand, nematode UBC7 showed strong homology to yeast UBC7. It is involved in degradation of the repressor and further confers resistance to cadmium in yeasts. The similarities among these proteins suggest that they belong to the same family.

It is speculated that UBE2G is involved in degradation of muscle-specific proteins and that a defect in said gene could lead to such diseases as muscular dystrophy. Recently, another proteolytic enzyme, calpain 3, was found to be responsible for limb-girdle muscular dystrophy type 2A [Richard, I., et al., Cell, 81, 27–40 (1995)]. At the present, the chromosomal location of UBE2G suggests no significant relationship with any hereditary muscular disease but it is likely that a relation to the gene will be unearthed by linkage analysis in future.

In accordance with this example, the novel UBE2G gene is provided and the use of said gene enables detection of its expression in various tissues and production of the UBE2G protein by the technology of genetic engineering. Through these, it becomes possible to study the degradation of muscle-specific proteins deeply involved in basic activities variegated and essential to cells, as mentioned above, and the functions of skeletal muscle, to diagnose various muscular diseases in which these are involved and further to screen out and evaluate drugs for the treatment and prevention of such diseases.

Example 8

TMP-2 gene (1) TMP-2 gene cloning and DNA sequencing

Following the procedure of Example 1 (1), cDNA clones were arbitrarily selected from a human fetal brain cDNA library and subjected to sequence analysis, and database searches were performed. As a result, a clone (GEN-092E10) having a cDNA sequence highly homologous to a transmembrane protein gene (accession No.: U19878) was found out.

Membrane protein genes have so far been cloned in frog (Xenopus laevis) and human. These are considered to be a gene for a transmembrane type protein having a follistatin module and an epidermal growth factor (EGF) domain (accession No.: U19878).

The sequence information of the above protein gene indicated that the GEN-092E10 clone was lacking in the 5' region, so that the λgt10 cDNA library (human fetal brain 5'-STRETCH PLUS cDNA; Clontech) was screened using the GEN-092E10 clone as a probe, whereby a cDNA clone containing a further 5' upstream region was isolated.

Both strands of this cDNA clone were sequenced, whereby the sequence covering the entire coding region became clear. This gene was named TMP-2 gene.

The TMP-2 gene was found to contain an open reading frame of 1,122 nucleotides, as shown under SEQ ID NO:26, encoding an amino acid sequence of 374 residues, as shown under SEQ ID NO:25. The nucleotide sequence of the entire TMP-2 cDNA clone comprises 1,721 nucleotides, as shown under SEQ ID NO:27.

As shown under SEQ ID NO:27, the 5' noncoding region was generally rich in GC. Several candidates for the initiation codon were found but, according to the scanning model, the 5th ATG of the cDNA clone (bases Nos. 368–370) was estimated as the initiation codon. The termination codon was located at nucleotides Nos. 1490–1492. The polyadenylation signal (AATAAA) was located at nucleotides Nos. 1703–1708. The calculated molecular weight of the TMP-2 gene product was 41,400 daltons.

As mentioned above, the transmembrane genes have a follistatin module and an EGF domain. These motifs were also found conserved in the novel human gene of the present invention.

The TMP-2 gene of the present invention presumably plays an important role in cell proliferation or intercellular communication, since, on the amino acid level, said gene shows homology, across the EGF domain, to TGF-$\alpha$ (transforming growth factor-$\alpha$; Derynck, R., et al., Cell, 38, 287–297 (1984)], beta-cellulin [Igarashi, K. and Folkman, J., Science, 259, 1604–1607 (1993)], heparin-binding EGF-like growth factor [Higashiyama, S., et al., Science, 251, 936–939 (1991)] and schwannoma-derived growth factor [Kimura, H., et al., Nature, 348, 257–260 (1990)].

(2) Northern blot analysis

Northern blot analysis was carried out as described in Example 1 (2). Thus, the clone GEN-092E10 was amplified by PCR, the PCR product was purified and labeled with [$^{32}$P]-dCTP (random-primed DNA labeling kit, Boehringer Mannheim), and the expression of TMP-2 mRNA in normal human tissues was examined using an MTN blot with the labeled product as a probe.

As a result, high levels of expression were detected in brain and prostate gland. Said TMP-2 gene mRNA was about 2 kb in size.

According to the present invention, the novel human TMP-2 gene is provided and the use of said gene makes it possible to detect the expression of said gene in various tissues or produce the human TMP-2 protein by the technology of genetic engineering and, through these, it becomes possible to study brain tumor and prostatic cancer, which are closely associated with cell proliferation or intercellular communication, as mentioned above, to diagnose these diseases and to screen out and evaluate drugs for the treatment and prevention of such diseases.

Example 9

Human NPIK gene (1) Human NPIK gene cloning and DNA sequencing

Following the procedures of Example 1 and Example 2, cDNA clones were arbitrarily selected from a human fetal brain cDNA library and subjected to sequence analysis, and database searches were performed. As a result, two cDNA clones highly homologous to the gene coding for an amino acid sequence conserved in phosphatidylinositol 3 and 4 kinases [Kunz, J., et al., Cell, 73, 585–596 (1993)] were obtained. These were named GEN-428B12c1 and GEN-428B12c2 and the entire sequences of these were determined as in the foregoing examples.

As a result, the GEN-428B12c1 cDNA clone and the GEN-428B12c2 clone were found to have coding sequences differing by 12 amino acid residues at the 5' terminus, the GEN-428B12c1 cDNA clone being longer by 12 amino acid residues.

The GEN-428B12c1 cDNA sequence of the human NPIK gene contained an open reading frame of 2,487 nucleotides, as shown under SEQ ID NO:32, encoding an amino acid sequence comprising 829 amino acid residues, as shown under SEQ ID NO:31. The nucleotide sequence of the full-length cDNA clone comprised 3,324 nucleotides as shown under SEQ ID NO:33.

The estimated initiation codon was located, as shown under SEQ ID NO:33, at nucleotides Nos. 115–117 corresponding to the second ATG triplet of the cDNA clone. The termination codon was located at nucleotides Nos. 2602–2604 and the polyadenylation signal (AATAAA) at Nos. 3305–3310.

On the other hand, the GEN-428B12c2 cDNA sequence of the human NPIK gene contained an open reading frame of 2,451 nucleotides, as shown under SEQ ID NO:29. The amino acid sequence encoded thereby comprised 817 amino acid residues, as shown under SEQ ID NO:28. The nucleotide sequence of the full-length cDNA clone comprised 3,602 nucleotides, as shown under SEQ ID NO:30.

The estimated initiation codon was located, as shown under SEQ ID NO:30, at nucleotides Nos. 429–431 corresponding to the 7th ATG triplet of the cDNA clone. The termination codon was located at nucleotides Nos. 2880–2882 and the polyadenylation signal (AATAAA) at Nos. 3583–3588.

(2) Northern blot analysis

Northern blot analysis was carried out as described in Example 1 (2). Thus, the entire sequence of human NPIK was amplified by PCR, the PCR product was purified and labeled with [$^{32}$P]-dCTP (random-primed DNA labeling kit, Boehringer Mannheim), and normal human tissues were examined for expression of the human NPIK mRNA using the MTN blot membrane with the labeled product as a probe.

As a result, the expression of the human NPIK gene was observed in 16 various human adult tissues examined and an about 3.8 kb transcript and an about 5 kb one could be detected.

Using primer A having the nucleotide sequence shown below in Table 8 and containing the initiation codon of the GEN-428B12c2 cDNA and primer B shown in table 8 and containing the termination codon, PCR was performed with Human Fetal Brain Marathon-Ready cDNA (Clontech) as a template, and the nucleotide sequence of the PCR product was determined.

TABLE 8

| Primer | Nucleotide sequence |
|---|---|
| Primer A | 5'-ATGGGAGATACAGTAGTGGAGC-3' |
| Primer B | 5'-TCACATGATGCCGTTGGTGAG-3' |

As a result, it was found that the human NPIK mRNA expressed included one lacking in nucleotides Nos. 1060–1104 of the GEN-428B12c1 cDNA sequence (SEQ ID NO:33) (amino acids Nos. 316–330 of the amino acid sequence under SEQ ID NO:31) and one lacking in nucleotides Nos. 1897–1911 of the GEN-428B12c1 cDNA sequence (SEQ ID NO:33) (amino acids Nos. 595–599 of the amino acid sequence under SEQ ID NO:31).

It was further revealed that polymorphism existed in this gene (428B12c1 .fasta), as shown below in Table 9, in the region of bases Nos. 1941–1966 of the GEN-428B12c1 cDNA sequence shown under SEQ ID NO:33, whereby a mutant protein was encoded which resulted from the mutation of IQDSCEITT (amino acid residues Nos. 610–618 in the amino acid sequence (SEQ ID NO:31) encoded by GEN-428B12c1 ) into YKILVISA.

TABLE 9

```
                                                 1930 1940 1950 1959
                                        TGGATCAAGCCAATACAAGATTCTTGTGAA
                                                        ||||||||||||||||||||||
TCCATTTGGGAACAGGAGCGAGTGCCCCTTTGGATCAAGCC—ATACAAGATTCTTGTG--
1900 1910 1920 1930 1940 1950
1960 1970 1980
ATTACGACTGATAGTGGCATG
||| || ||||||||||||
ATTTCGGCTGATAGTGGCATGATTGAACCAGTGGTCAATGCTGTGTCCATCCATCAGGTG
1960 1970 1980 1990 2000 2010
```

(3) Chromosomal mapping of human NPIK gene by FISH

Chromosomal mapping of the human NPIK gene was carried out by FISH as described in Example 1 (3).

As a result, it was found that the locus of the human NPIK gene is in the chromosomal position 1q21.1- q21.3.

The human NPIK gene, a novel human gene, of the present invention included two cDNAs differing in the 5' region and capable of encoding 829 and 817 amino acid residues, as mentioned above. In view of this and further in view of the findings that the mRNA corresponding to this gene includes two deletable sites and there occurs polymorphism in a specific region corresponding to amino acid residues Nos. 610–618 of the GEN-428B12c1 amino acid sequence (SEQ ID NO:31), whereby a mutant protein is encoded, it is conceivable that human NPIK includes species resulting from a certain number of combinations, namely human NPIK, deletion-containing human NPIK, human NPIK mutant and/or deletion-containing human NPIK mutant.

Recently, several proteins belonging to the family including the above-mentioned PI3 and 4 kinases have protein kinase activity [Dhand, R., et al., EMBO J., 13, 522–533 (1994); Stack, J. H. and Emr, S. D., J. Biol. Chem., 269, 31552–31562 (1994); Hartley, K. O., et al., Cell, 82, 848–856 (1995)].

It was also revealed that a protein belonging to this family is involved in DNA repair [Hartley, K. O., et al., Cell, 82, 849–856 (1995)] and is a causative gene of ataxia [Savitsky, K., et al., Science, 268, 1749–1753 (1995)].

It can be anticipated that the human NPIK gene-encoded protein highly homologous to the family of these PI kinases is a novel enzyme phosphorylating lipids or proteins.

According to this example, the novel human NPIK gene is provided. The use of said gene makes it possible to detect the expression of said gene in various tissues and manufacture the human NPIK protein by the technology of genetic engineering and, through these, it becomes possible to study lipid- or protein-phosphrylating enzymes such as mentioned above, study DNA repairing, study or diagnose diseases in which these are involved, for example cancer, and screen out and evaluate drugs for the treatment or prevention thereof.

(4) Construction of an expression vector for fusion protein

To subclone the coding region for a human NPIK gene (GEN-428B12c2), first of all, two primers, C1 and C2, having the sequences shown below in Table 10 were formed based on the information on the DNA sequences obtained above in (1).

TABLE 10

| Primer | Nucleotide sequence |
|---|---|
| Primer C1 | 5'-CTCAGATCTATGGGAGATACAGTAGTGGAGC-3' |
| Primer C2 | 5'-TCGAGATCTTCACATGATGCCGTTGGTGAG-3' |

Both of the primers C1 and C2 have a BglII site, and primer C2 is an antisense primer.

Using these two primers, cDNA derived from human fetal brain mRNA was amplified by PCR to provide a product having a length of about 2500 bases. The amplified cDNA was precipitated from ethanol and inserted into pT7BlueT-Vector (product of Novagen) and subcloning was completed. The entire sequence was determined in the same manner as above in Examples. As a result, it was revealed that this gene had polymorphism shown above in Table 9.

The above cDNA was cleaved by BglII and subjected to agarose gel electrophoresis. The cDNA was then excised from agarose gel and collected using GENECLEAN II KIT (product of Bio 101). The cDNA was inserted into pBlueBacHis2B-Vector (product of Invitrogen) at the BglII cleavage site and subcloning was completed.

The fusion vector thus obtained had a BglII cleavage site and was an expression vector for a fusion protein of the contemplated gene product (about 91 kd) and 38 amino acids derived from pBlueBacHis2B-Vector and containing a polyhistidine region and an epitope recognizing Anti-Xpress™ antibody (product of Invitrogen).

(5) Transfection into insect cell Sf-9

The human NPIK gene was expressed according to the Baculovirus expression system. Baculovirus is a cyclic double-stranded insect-pathogenic virus and can produce large amounts of inclusion bodies named polyhedrins in the cells of insects. Using Bac-N-Blue™ Transfection Kit utilizing this characteristic of Baculovirus and developed by Invitrogen, the Baculovirus expression was carried out.

Stated more specifically, 4 $\mu$g of pBlueBacHis2B containing the region of the human NPIK gene and 1 $\mu$g of Bac-N-Blue™ DNA (product of Invitrogen) were co-transfected into Sf-9 cells in the presence of Insectin™ liposomes (product of Invitrogen).

Prior to co-transfection, LacZ gene was incorporated into Bac-N-Blue™ DNA, so that LacZ would be expressed only when homologous recombination took place between the Bac-N-Blue™ DNA and pBlueBacHis2B. Thus when the co-transfected Sf-9 cells were incubated on agar medium, the plaques of the virus expressing the contemplated gene were easily detected as blue plaques.

The blue plaques were excised from each agar and suspended in 400 $\mu$l of medium to disperse the virus thereon. The suspension was subjected to centrifugation to give a supernatant containing the virus. Sf-9 cells were infected with the virus again to increase the titre and to obtain a large amount of infective virus solution.

(6) Preparation of human NPIK

The expression of the contemplated human NPIK gene was confirmed three days after infection with the virus as follows.

Sf-9 cells were collected and washed with PBS. The cells were boiled with a SDS-PAGE loading buffer for 5 minutes and SDS-PAGE was performed. According to the western blot technique using Anti-Xpress as an antibody, the contemplated protein was detected at the position of its presumed molecular weight. By contrast, in the case of control cells uninfected with the virus, no band corresponding to human NPIK was observed in the same test.

Stated more specifically, three days after the infection of 15 flasks (175-$cm^2$, FALCON) of semi-confluent Sf-9 cells, the cells were harvested and washed with PBS, followed by resuspension in a buffer (20 mM Tris/HCl (pH 7.5), 1 mM EDTA and 1 mM DTT). The suspended cells were lysed by 4 time-sonications for 30 seconds at 4° C. with 30 seconds intervals. The sonicated cells were subjected to centrifugation and the supernatant was collected. The protein in the supernatant was immunoprecipitated using an Anti-Xpress antibody and obtained as a slurry of protein A-Sepharose beads. The slurry was boiled with a SDS-PAGE loading buffer for 5 minutes. SDS-PAGE was performed for identification and quantification of NPIK. The slurry itself was subjected to the following assaying.

(7) Confirmation of PI4 Kinase activity

NPIK was expected to have the activity of incorporation phosphoric acid at the 4-position of the inositol ring of phosphatidylinositol (PI), namely, PI4 Kinase activity.

PI4 Kinase activity of NPIK was assayed according to the method of Takenawa, et al. (Yamakawa, A. and Takenawa, T., J. Biol. Chem., 263, 17555–17560 (1988)) as shown below.

First prepared was a mixture of 10 $\mu$l of a NPIK slurry (20 mM Tris/HCl (pH 7.5), 1 mM EDTA, 1 mM DTT and 50% protein A beads), 10 $\mu$l of a PI solution (prepared by drying 5 mg of a PI-containing commercial chloroform solution in a stream of nitrogen onto a glass tube wall, adding 1 ml of 20 mM Tris/HCl (pH 7.5) buffer and forming micelles by sonication), 10 $\mu$l of an applied buffer (210 mM Tris/HCl (pH 7.5), 5 mM EGTA and 100 mM $MgCl_2$) and 10 $\mu$l of distilled water. Thereto was added 10 $\mu$l of an ATP solution (5 $\mu$l of 500 $\mu$M ATP, 4.9 $\mu$l of distilled water and 0.1 $\mu$l of $\gamma$-$^{32}$P ATP (6000 Ci/mmol, product of NEN Co., Ltd.)). The reaction was started at 30° C. and continued for 2, 5, 10 and 20 minutes. The time 10 minutes was set as incubation time because a straight-line increase was observed around 10 minutes in incorporation of phosphoric acid into PI in the assaying process described below.

After completion of the reaction, PI was fractionated by the solvent extraction method and finally re-suspended in chloroform. The suspension was developed by thin layer chromatography (TLC) and the radioactivity of the reaction product at the PI4P-position was assayed using an analyzer (trade name: Bio-Image; product of Fuji Photo Film Co., Ltd.).

FIG. 1 shows the results. FIG. 1 is an analytical diagram of the results of assaying the radioactivity based on TLC as mentioned above. The right lane (2) is the fraction of Sf-9 cell cytoplasm infected with the NPIK-containing virus, whereas the left lane (1) is the fraction of uninfected Sf-9 cell cytoplasm.

Also, predetermined amounts of Triton X-100 and adenosine were added to the above reaction system to check how such addition would affect the PI4 Kinase activity. The PI4 Kinase activity was assayed in the same manner as above.

FIG. 2 shows the results. The results confirmed that NPIK had a typical PI4 Kinaze activity accelerated by Triton X-100 and inhibited by adenosine.

Example 10 nel-related protein type 1 (NRP1) gene and nel-related protein type 2 (NRP2) gene (1) Cloning and DNA sequencing of NRP1 gene and NRP2 gene EGF-like repeats have been found in many membrane proteins and in proteins related to growth regulation and differentiation. This motif seems to be involved in protein-protein interactions.

Recently, a gene encoding nel, a novel peptide containing five EGF-like repeats, was cloned from a chick embryonic cDNA library [Matsuhashi, S., et al., Dev. Dynamics, 203, 212–222 (1995)]. This product is considered to be a transmembrane molecule with its EGF-like repeats in the extracellular domain. A 4.5 kb transcript (nel mRNA) is expressed in various tissues at the embryonic stage and exclusively in brain and retina after hatching.

Following the procedure of Example 1 (1), cDNA clones were randomly selected from a human fetal brain cDNA library and subjected to sequence analysis, followed by database searching. As a result, two cDNA clones with significantly high homology to the above-mentioned nel were found and named GEN-073E07 and GEN-093E05, respectively.

Since both clones were lacking in the 5' portion, 5' RACE was performed in the same manner as in Example 2 (2) to obtain the entire coding regions.

As for the primers for 5' RACE, primers having an arbitrary sequence obtained from the cDNA sequences of the above clones were synthesized while the anchor primer attached to a commercial kit was used as such.

5' RACE clones obtained from the PCR were sequenced and the sequences seemingly covering the entire coding regions of both genes were obtained. These genes were respectively named nel-related protein type 1 (NRP1) gene and nel-related protein type 2 (NRP2) gene.

The NRP1 gene contains an open reading frame of 2,430 nucleotides, as shown under SEQ ID NO:35, the amino acid sequence deduced therefrom comprises 810 amino acid residues, as shown under SEQ ID NO:34, and the nucleotide sequence of the entire cDNA clone of said NRP1 gene comprises 2,977 nucleotides, as shown under SEQ ID NO:36.

On the other hand, the NRP2 gene contains an open reading frame of 2,448 nucleotides, as shown under SEQ ID NO:38, the amino acid sequence deduced therefrom comprises 816 amino acid residues, as shown under SEQ ID NO:37, and the nucleotide sequence of the entire cDNA clone of said NRP2 gene comprises 3,198 nucleotides, as shown under SEQ ID NO:39.

Furthermore, the coding regions were amplified by RT-PCR to exclude the possibility that either of the sequences obtained was a chimeric cDNA.

The deduced NRP1 and NRP2 gene products both showed highly hydrophobic N termini capable of functioning as signal peptides for membrane insertion. As compared with chick embryonic nel, they both appeared to have no hydrophobic transmembrane domain. Comparison among NRP1, NRP2 and nel with respect to the deduced peptide sequences revealed that NRP2 has 80% homology on the amino acid level and is more closely related to nel than NRP1 having 50% homology. The cysteine residues in cysteine-rich domains and EGF-like repeats were found completely conserved.

The most remarkable difference between the NRPs and the chick protein was that the human homologs lack the putative transmembrane domain of nel. However, even in this lacking region, the nucleotide sequences of NRPs were very similar to that of nel. Furthermore, the two NRPs each possessed six EGF-like repeats, whereas nel has only five.

Other unique motifs of nel as reported by Matsuhashi et al. [Matsuhashi, S., et al., Dev. Dynamics, 203, 212–222

(1995)] were also found in the NRPs at equivalent positions. Since as mentioned above, it was shown that the two deduced NRP peptides are not transmembrane proteins, the NRPs might be secretory proteins or proteins anchored to membranes as a result of posttranslational modification.

The present inventors speculate that NRPs might function as ligands by stimulating other molecules such as EGF receptors. The present inventors further found that an extra EGF-like repeat could be encoded in nel upon frame shifting of the membrane domain region of nel.

When paralleled and compared with NRP2 and nel, the frame-shifted amino acid sequence showed similarities over the whole range of NRP2 and of nel, suggesting that NRP2 might be a human counterpart of nel. In contrast, NRP1 is considered to be not a human counterpart of nel but a homologous gene.

(2) Northern blot analysis

Northern blot analysis was carried out as described in Example 1 (2). Thus, the entire sequences of both clones cDNAs were amplified by PCR, the PCR products were purified and labeled with [$^{32}$P]-dCTP (random-primed DNA labeling kit, Boehringer Mannheim) and human normal tissues were examined for NRP mRNA expression using an MTN blot with the labeled products as two probes.

Sixteen adult tissues and four human fetal tissues were examined for the expression pattern of two NRPs.

As a result of the Northern blot analysis, it was found that a 3.5 kb transcript of NRP1 was weakly expressed in fetal and adult brain and kidney. A 3.6 kb transcript of NRP2 was strongly expressed in adult and fetal brain alone, with weak expression thereof in fetal kidney as well.

This suggests that NRPs might play a brain-specific role, for example as signal molecules for growth regulation. In addition, these genes might have a particular function in kidney.

(3) Chromosomal mapping of NRP1 gene and NRP2 gene by FISH

Chromosomal mapping of the NRP1 gene and NRP2 gene was performed by FISH as described in Example 1 (3).

As a result, it was revealed that the chromosomal locus of the NRP1 gene is localized to 11p5.1-p15.2 and the chromosomal locus of the NRP2 gene to 12q13.11-q13.12.

According to the present invention, the novel human NRP1 gene and NRP2 gene are provided and the use of said genes makes it possible to detect the expression of said genes in various tissues and produce the human NRP1 and NRP2 proteins by the technology of genetic engineering. They can further be used in the study of the brain neurotransmission system, diagnosis of various diseases related to neurotransmission in the brain, and the screening and evaluation of drugs for the treatment and prevention of such diseases. Furthermore, the possibility is suggested that these EGF domain-containing NRPs act as growth factors in brain, hence they may be useful in the diagnosis and treatment of various kinds of intracerebral tumor and effective in nerve regeneration in cases of degenerative nervous diseases.

Example 11

GSPT1-related protein (GSPT1-TK) gene (1) GSPT1-TK gene cloning and DNA sequencing The human GSPT1 gene is one of the human homologous genes of the yeast GST1 gene that encodes the GTP-binding protein essential for the G1 to S phase transition in the cell cycle. The yeast GST1 gene, first identified as a protein capable of complementing a temperature-sensitive gst1 (G1 -to-S transition) mutant of *Saccharomyces cerevisiae*, was isolated from a yeast genomic library [Kikuchi, Y., Shimatake, H. and Kikuchi, A., EMBO J., 7, 1175–1182 (1988)] and encoded a protein with a target site of cAMP-dependent protein kinases and a GTPase domain.

The human GSPT1 gene was isolated from a KB cell cDNA library by hybridization using the yeast GST1 gene as a probe [Hoshino, S., Miyazawa, H., Enomoto, T., Hanaoka, F., Kikuchi, Y., Kikuchi, A. and Ui, M., EMBO J., 8, 3807–3814 (1989)]. The deduced protein of said GSPT1 gene, like yeast GST1, has a GTP-binding domain and a GTPase activity center, and plays an important role in cell proliferation.

Furthermore, a breakpoint for chromosome rearrangement has been observed in the GSPT1 gene located in the chromosomal locus 16p13.3 in patients with acute nonlymphocytic leukemia (ANLL) [Ozawa, K., Murakami, Y., Eki, T., Yokoyama, K. Soeda, E., Hoshino, S. Ui, M. and Hanaoka, F., Somatic Cell and Molecular Genet., 18, 189–194 (1992)].

cDNA clones were randomly selected from a human fetal brain cDNA library and subjected to sequence analysis as described in Example 1 (1) and database searching was performed and, as a result, a clone having a 0.3 kb cDNA sequence highly homologous to the above-mentioned GSPT1 gene was found and named GEN-077A09. The GEN-077A09 clone seemed to be lacking in the 5' region, so that 5' RACE was carried out in the same manner as in Example 2 (2) to obtain the entire coding region.

The primers used for the 5' RACE were P1 and P2 primers respectively having the nucleotide sequences shown in Table 11 as designed based on the known cDNA sequence of the above-mentioned cDNA, and the anchor primer used was the one attached to the commercial kit. Thirtyfive cycles of PCR were performed under the following conditions: 94° C. for 45 seconds, 58° C. for 45 seconds and 72° C. for 2 minutes. Finally, elongation reaction was carried out at 72° C. for 7 minutes.

TABLE 11

| Primer | Nucleotide sequence |
|---|---|
| P1 primer | 5'-GATTTGTGCTCAATAATCACTATCTGAA-3' |
| P2 primer | 5'-GGTTACTAGGATCACAAAGTATGAATTCTGGAA-3' |

Several of the 5' RACE clones obtained from the above PCR were sequenced and the base sequence of that cDNA clone showing overlapping between the 5' RACE clones and the GEN-077A09 clone was determined to thereby reveal the sequence regarded as covering the entire coding region. This was named GSPT1-related protein “GSPT1-TK gene”.

The GSPT1-TK gene was found to contain an open reading frame of 1,497 nucleotides, as shown under SEQ ID NO:41. The amino acid sequence deduced therefrom contained 499 amino acid residues, as shown under SEQ ID NO:40.

The nucleotide sequence of the whole cDNA clone of the GSPT1-TK gene was found to comprise 2,057 nucleotides, as shown under SEQ ID NO:42, and the molecular weight was calculated at 55,740 daltons.

The first methionine code (ATG) in the open reading frame had no in-frame termination codon but this ATG was surrounded by a sequence similar to the Kozak consensus sequence for translational initiation. Therefore, it was concluded that this ATG triplet occurring in positions 144–146 of the relevant sequence is the initiation codon.

Furthermore, a polyadenylation signal, AATAAA, was observed 13 nucleotides upstream from the polyadenylation site.

Human GSPT1-TK contains a glutamic acid rich region near the N terminus, and 18 of 20 glutamic acid residues occurring in this region of human GSPT1-TK are conserved and align perfectly with those of the human GSPT1 protein. Several regions (G1, G2, G3, G4 and G5) of GTP-binding proteins that are responsible for guanine nucleotide binding and hydrolysis were found conserved in the GSPT1-TK protein just as in the human GSPT1 protein.

Thus, the DNA sequence of human GSPT1-TK was found 89.4% identical, and the amino acid sequence deduced therefrom 92.4% identical, with the corresponding sequence of human GSPT1 which supposedly plays an important role in the G1 to S phase transition in the cell cycle. Said amino acid sequence showed 50.8% identity with that of yeast GST1.

(2) Northern blot analysis

Northern blot analysis was carried out as described in Example 1 (2). Thus, the GEN-077A09 cDNA clone was amplified by PCR, the PCR product was purified and labeled with [$^{32}$P]-dCTP (random-primed DNA labeling kit, Boehringer Mannheim), and normal human tissues were examined for the expression of GSPT1-TK mRNA therein using an MTN blot with the labeled product as a probe.

As a result of the Northern blot analysis, a 2.7 kb major transcript was detected in various tissues. The level of human GSPT1-TK expression seemed highest in brain and in testis.

(3) Chromosome mapping of GSPT1-TK gene by FISH

Chromosome mapping of the GSPT1-TK gene was performed by FISH as described in Example 1 (3).

As a result, it was found that the GSPT1-TK gene is localized at the chromosomal locus 19p13.3. In this chromosomal localization site, reciprocal location has been observed very frequently in cases of acute lymphocytic leukemia (ALL) and acute myeloid leukemia (AML). In addition, it is reported that acute non-lymphocytic leukemia (ALL) is associated with rearrangements involving the human GSPT1 region [Ozawa, K., Murakami, Y., Eki, T., Yokoyama, K., Soeda, E., Hoshino, S., Ui, M. and Hanaoka, F., Somatic Cell and Molecular Genet., 18, 189–194 (1992)].

In view of the above, it is suggested that this gene is the best candidate gene associated with ALL and AML.

In accordance with the present invention, the novel human GSPT1-TK gene is provided and the use of said gene makes it possible to detect the expression of said gene in various tissues and produce the human GSPT1-TK protein by the technology of genetic engineering. These can be used in the studies of cell proliferation, as mentioned above, and further make it possible to diagnose various diseases associated with the chromosomal locus of this gene, for example acute myelocytic leukemia. This is because translocation of this gene may result in decomposition of the GSPT1-TK gene and further some or other fused protein expressed upon said translocation may cause such diseases.

Furthermore, it is expected that diagnosis and treatment of said diseases can be made possible by producing antibodies to such fused protein, revealing the intracellular localization of said protein and examining its expression specific to said diseases. Therefore, it is also expected that the use of the gene of the present invention makes it possible to screen out and evaluate drugs for the treatment and prevention of said diseases.

We claim:

1. A GDP dissociation stimulating protein gene comprising a nucleotide sequence coding for the amino acid sequence shown under SEQ ID NO:1.

2. A GDP dissociation stimulating protein gene comprising the nucleotide sequence shown under SEQ ID NO:2.

3. A GDP dissociation stimulating protein gene as defined in claim 2 which has the nucleotide sequence shown under SEQ ID NO:3.

* * * * *